US007841537B2

(12) United States Patent
Starling et al.

(10) Patent No.: US 7,841,537 B2

(45) Date of Patent: Nov. 30, 2010

(54) SYSTEM FOR INTERACTING WITH ANALOG-PRINTED SUBSTRATE

(75) Inventors: Scott Matthew Starling, Balmain (AU); Simone Charlotte Vonwiller, Balmain (AU); Damon Donald Ridley, Balmain (AU); Kia Silverbrook, Balmain (AU)

(73) Assignee: Silverbrook Research Pty Ltd, Balmain, New South Wales (AU)

( * ) Notice: Subject to any disclaimer, the term of this patent is extended or adjusted under 35 U.S.C. 154(b) by 0 days.

(21) Appl. No.: 12/482,396

(22) Filed: Jun. 10, 2009

(65) Prior Publication Data

US 2009/0242642 A1 Oct. 1, 2009

Related U.S. Application Data

(63) Continuation of application No. 11/849,360, filed on Sep. 4, 2007, now Pat. No. 7,559,983.

(60) Provisional application No. 60/851,754, filed on Oct. 16, 2006.

(51) Int. Cl.
*G06K 19/06* (2006.01)

(52) U.S. Cl. .................. 235/491; 235/462.01; 235/488; 347/104

(58) Field of Classification Search ................. 235/491, 235/462.01, 488; 347/104

See application file for complete search history.

(56) References Cited

U.S. PATENT DOCUMENTS 4,864,618 A 9/1989 Wright et al.
5,051,736 A 9/1991 Bennett et al.
5,477,012 A 12/1995 Sekendur
5,652,412 A 7/1997 Lazzouni et al.
5,661,506 A 8/1997 Lazzouni et al.
5,692,073 A 11/1997 Cass
5,810,915 A 9/1998 Nagai et al.
5,852,434 A 12/1998 Sekendur
5,882,390 A 3/1999 Nagai et al.
6,076,734 A 6/2000 Dougherty et al.
6,939,399 B2 9/2005 Yabuki
6,964,374 B1 11/2005 Djuknic et al.
7,148,345 B2 12/2006 Vonwiller et al.
7,219,988 B2 5/2007 Hanaki et al.
2005/0203293 A1* 9/2005 Hirota et al. ................ 540/136
2008/0008945 A1 1/2008 Onaka et al.
2008/0064596 A1* 3/2008 Iino et al. ................... 503/201
2008/0119359 A1* 5/2008 Utagawa et al. ............. 503/201

(Continued)

FOREIGN PATENT DOCUMENTS

GB 2306669 A 5/1997

(Continued)

OTHER PUBLICATIONS

Dymetman, M., and Copperman, M., “Intelligent Paper in Electronic Publishing, Artist Imaging, and Digital Typography, Proceedings of EP ’98”, Mar./Apr. 1998, Springer Verlag LNCS 1375, pp. 392-406. * .

*Primary Examiner*—Allyson N Trail

(57) ABSTRACT

A system for interacting with a coded substrate. The system comprises a substrate having human-readable information and machine-readable coded data disposed thereon and a sensing device for reading the machine-readable coded data. The coded data comprises an IR-absorbing phthalocyanine dye having sulfonate groups. A counterion of each sulfonate group is a phosphonium cation.

16 Claims, 24 Drawing Sheets

U.S. PATENT DOCUMENTS

| | | | | |
|---|---|---|---|---|
| 2008/0241492 | A1* | 10/2008 | Demartin Maeder et al. | 428/211.1 |
| 2009/0076278 | A1* | 3/2009 | Dan-Oh et al. | 548/150 |
| 2009/0252901 | A1* | 10/2009 | Haas et al. | 428/29 |
| 2010/0020151 | A1* | 1/2010 | Jones et al. | 347/104 |

FOREIGN PATENT DOCUMENTS

| | | | |
|---|---|---|---|
| JP | 63-210175 | | 8/1988 |
| JP | 06-016982 | | 1/1994 |
| JP | 07-138511 | | 5/1995 |
| WO | WO 99/18487 | A2 | 4/1999 |
| WO | WO 99/50787 | A1 | 10/1999 |
| WO | WO 2006/015415 | | 2/2006 |

* cited by examiner

POWER MANAGER
PEN-DOWN DETECTOR
ANALOG-TO-DIGITAL CONV
FORCE SENSOR PHOTODIODE
PROCESSOR
X-Y ACCELERO-METERS
512KB DRAM
FORCE SENSOR IR LED
FLASH MEMORY
ILLUMINATION IR LED
PROCESSOR ADDRESS, DATA AND CONTROL BUS
PARALLEL I/F
BASEBAND CIRCUIT
TRI-COLOR STATUS LED
RF CIRCUIT
RF RESONATORS & INDUCTORS
TRANSCEIVER CONTROLLER
IMAGE SENSOR I/F
215×215 CCD IMAGE SENSOR
151
150
149
144
134
145
190
148
146
143
147
131
133
155
154
116
152
153
156
112
132

SYSTEM FOR INTERACTING WITH ANALOG-PRINTED SUBSTRATE

CROSS REFERENCE TO RELATED APPLICATION

This application is a continuation of U.S. application Ser. No. 11/849,360 filed Sep. 4, 2007, all of which are herein incorporated by reference.

FIELD OF THE INVENTION

The present application relates to phthalocyanine dyes, such as naphthalocyanines. It has been developed primarily for optimizing the absorption characteristics of IR-absorbing phthalocyanine dyes in oil-based inks suitable for analog printing.

CROSS-REFERENCES

Various methods, systems and apparatus relating to the present invention are disclosed in the following co-pending applications filed by the applicant or assignee of the present application:

| | | | | |
|---|---|---|---|---|
| 6,750,901 | 6,476,863 | 6,788,336 | 7,249,108 | 6,566,858 |
| 6,331,946 | 6,246,970 | 6,442,525 | 7,346,586 | 09/505,951 |
| 6,374,354 | 7,246,098 | 6,816,968 | 6,757,832 | 6,334,190 |
| 6,745,331 | 7,249,109 | 7,197,642 | 7,093,139 | 7,509,292 |
| 10/636,283 | 10/866,608 | 7,210,038 | 7,401,223 | 10/940,653 |
| 10/942,858 | 7,364,256 | 7,258,417 | 7,293,853 | 7,328,968 |
| 7,270,395 | 7,461,916 | 7,510,264 | 7,334,864 | 7,255,419 |
| 7,284,819 | 7,229,148 | 7,258,416 | 7,273,263 | 7,270,393 |
| 6,984,017 | 7,347,526 | 7,357,477 | 7,465,015 | 7,364,255 |
| 7,357,476 | 11/003,614 | 7,284,820 | 7,341,328 | 7,246,875 |
| 7,322,669 | 7,445,311 | 7,452,052 | 7,455,383 | 7,448,724 |
| 7,441,864 | 11/482,975 | 11/482,970 | 11/482,968 | 11/482,972 |
| 11/482,971 | 11/482,969 | 7,506,958 | 7,472,981 | 7,448,722 |
| 7,438,381 | 7,441,863 | 7,438,382 | 7,425,051 | 7,399,057 |
| 11/246,671 | 11/246,670 | 11/246,669 | 7,448,720 | 7,448,723 |
| 7,445,310 | 7,399,054 | 7,425,049 | 7,367,648 | 7,370,936 |
| 7,401,886 | 7,506,952 | 7,401,887 | 7,384,119 | 7,401,888 |
| 7,387,358 | 7,413,281 | 11/482,958 | 7,467,846 | 11/482,962 |
| 11/482,963 | 11/482,956 | 11/482,954 | 11/482,974 | 11/482,957 |
| 11/482,987 | 11/482,959 | 11/482,960 | 11/482,961 | 11/482,964 |
| 11/482,965 | 11/495,815 | 11/495,816 | 11/495,817 | 10/815,621 |
| 7,243,835 | 10/815,630 | 10/815,637 | 10/815,638 | 7,251,050 |
| 10/815,642 | 7,097,094 | 7,137,549 | 10/815,618 | 7,156,292 |
| 10/815,635 | 7,357,323 | 10/815,634 | 7,137,566 | 7,131,596 |
| 7,128,265 | 7,207,485 | 7,197,374 | 7,175,089 | 10/815,617 |
| 10/815,620 | 7,178,719 | 7,506,808 | 7,207,483 | 7,296,737 |
| 7,270,266 | 10/815,614 | 11/488,162 | 11/488,163 | 11/488,164 |
| 11/488,167 | 11/488,168 | 11/488,165 | 11/488,166 | 7,267,273 |
| 10/815,636 | 7,128,270 | 11/041,650 | 11/041,651 | 7,506,168 |
| 7,441,712 | 11/041,610 | 11/041,609 | 11/041,626 | 11/041,627 |
| 11/041,624 | 7,395,963 | 7,457,961 | 11/041,580 | 7,467,300 |
| 7,467,299 | 11/041,648 | 7,457,007 | 7,150,398 | 7,159,777 |
| 7,450,273 | 7,188,769 | 7,097,106 | 7,070,110 | 7,243,849 |
| 7,469,836 | 6,623,101 | 6,406,129 | 6,505,916 | 6,457,809 |
| 6,550,895 | 6,457,812 | 7,152,962 | 6,428,133 | 7,204,941 |
| 7,282,164 | 7,465,342 | 7,278,727 | 7,417,141 | 7,452,989 |
| 7,367,665 | 7,138,391 | 7,153,956 | 7,423,145 | 7,456,277 |
| 10/913,376 | 7,122,076 | 7,148,345 | 11/172,816 | 7,470,315 |
| 11/172,814 | 11/482,990 | 11/482,986 | 11/482,985 | 7,416,280 |
| 7,252,366 | 7,488,051 | 7,360,865 | 11/482,967 | 11/482,966 |
| 11/482,988 | 11/482,989 | 7,438,371 | 7,465,017 | 7,441,862 |
| 11/293,841 | 7,458,659 | 11/293,797 | 7,455,376 | 11/124,158 |
| 11/124,196 | 11/124,199 | 11/124,162 | 11/124,202 | 11/124,197 |
| 11/124,154 | 11/124,198 | 7,284,921 | 11/124,151 | 7,407,257 |
| 7,470,019 | 11/124,175 | 7,392,950 | 11/124,149 | 7,360,880 |
| 11/124,173 | 7,517,046 | 7,236,271 | 11/124,174 | 11/124,194 |
| 11/124,164 | 7,465,047 | 11/124,195 | 11/124,166 | 11/124,150 |
| 11/124,172 | 11/124,165 | 11/124,186 | 11/124,185 | 11/124,184 |
| 11/124,182 | 11/124,201 | 11/124,171 | 11/124,181 | 11/124,161 |

-continued

| | | | | |
|---|---|---|---|---|
| 11/124,156 | 11/124,191 | 11/124,159 | 7,370,932 | 7,404,616 |
| 11/124,187 | 11/124,189 | 11/124,190 | 7,500,268 | 11/124,193 |
| 7,447,908 | 11/124,178 | 11/124,177 | 7,456,994 | 7,431,449 |
| 7,466,444 | 11/124,179 | 11/124,169 | 11/187,976 | 11/188,011 |
| 11/188,014 | 7,530,446 | 11/228,540 | 11/228,500 | 11/228,501 |
| 11/228,530 | 11/228,490 | 11/228,531 | 11/228,504 | 11/228,533 |
| 11/228,502 | 11/228,507 | 11/228,482 | 11/228,505 | 11/228,497 |
| 11/228,487 | 11/228,529 | 11/228,484 | 7,499,765 | 11/228,518 |
| 11/228,536 | 11/228,496 | 11/228,488 | 11/228,506 | 11/228,516 |
| 11/228,526 | 11/228,539 | 11/228,538 | 11/228,524 | 11/228,523 |
| 7,506,802 | 11/228,528 | 11/228,527 | 7,403,797 | 11/228,520 |
| 11/228,498 | 11/228,511 | 11/228,522 | 11/228,537 | 11/228,534 |
| 11/228,491 | 11/228,499 | 11/228,509 | 11/228,492 | 11/228,493 |
| 11/228,510 | 11/228,508 | 11/228,512 | 11/228,514 | 11/228,494 |
| 7,438,215 | 11/228,486 | 11/228,481 | 11/228,477 | 7,357,311 |
| 7,380,709 | 7,428,986 | 7,403,796 | 7,407,092 | 11/228,513 |
| 11/228,503 | 7,469,829 | 11/228,535 | 11/228,478 | 11/228,479 |
| 6,238,115 | 6,386,535 | 6,398,344 | 6,612,240 | 6,752,549 |
| 6,805,049 | 6,971,313 | 6,899,480 | 6,860,664 | 6,925,935 |
| 6,966,636 | 7,024,995 | 7,284,852 | 6,926,455 | 7,056,038 |
| 6,869,172 | 7,021,843 | 6,988,845 | 6,964,533 | 6,981,809 |
| 7,284,822 | 7,258,067 | 7,322,757 | 7,222,941 | 7,284,925 |
| 7,278,795 | 7,249,904 | 7,152,972 | 6,746,105 | 11/246,687 |
| 11/246,718 | 7,322,681 | 11/246,686 | 11/246,703 | 11/246,691 |
| 7,510,267 | 7465041 | 11/246,712 | 7,465,032 | 7,401,890 |
| 7,401,910 | 7,470,010 | 11/246,702 | 7,431,432 | 7,465,037 |
| 7,445,317 | 11/246,699 | 11/246,675 | 11/246,674 | 11/246,667 |
| 7,156,508 | 7,159,972 | 7,083,271 | 7,165,834 | 7,080,894 |
| 7,201,469 | 7,090,336 | 7,156,489 | 7,413,283 | 7,438,385 |
| 7,083,257 | 7,258,422 | 7,255,423 | 7,219,980 | 10/760,253 |
| 7,416,274 | 7,367,649 | 7,118,192 | 10/760,194 | 7,322,672 |
| 7,077,505 | 7,198,354 | 7,077,5041 | 0/760,189 | 7,198,355 |
| 7,401,894 | 7,322,676 | 7,152,959 | 7,213,906 | 7,178,901 |
| 7,222,938 | 7,108,353 | 7,104,629 | 7,455,392 | 7,370,939 |
| 7,429,095 | 7,404,621 | 7,261,401 | 7,461,919 | 7,438,388 |
| 7,328,972 | 7,322,673 | 7,303,930 | 7,401,405 | 7,464,466 |
| 7,464,465 | 7,246,886 | 7,128,400 | 7,108,355 | 6,991,322 |
| 7,287,836 | 7,118,197 | 10/728,784 | 7,364,269 | 7,077,493 |
| 6,962,402 | 10/728,803 | 7,147,308 | 7,524,034 | 7,118,198 |
| 7,168,790 | 7,172,270 | 7,229,155 | 6,830,318 | 7,195,342 |
| 7,175,261 | 7,465,035 | 7,108,356 | 7,118,202 | 7,510,269 |
| 7,134,744 | 7,510,270 | 7,134,743 | 7,182,439 | 7,210,768 |
| 7,465,036 | 7,134,745 | 7,156,484 | 7,118,201 | 7,111,926 |
| 7,431,433 | 7,018,021 | 7,401,901 | 7,468,139 | 11/188,017 |
| 7,128,402 | 7,387,369 | 7,484,832 | 11/490,041 | 7,506,968 |
| 7,284,839 | 7,246,885 | 7,229,156 | 11/505,846 | 7,467,855 |
| 7,293,858 | 7,520,594 | 11/524,938 | 7,258,427 | 11/524,912 |
| 11/097,308 | 7,448,729 | 7,246,876 | 7,431,431 | 7,419,249 |
| 7,377,623 | 7,328,978 | 7,334,876 | 7,147,306 | 7,261,394 |
| 11/482,953 | 11/482,977 | 7,491,911 | 11/544,779 | 10/944,043 |
| 11/182,002 | 11/202,251 | 7,466,440 | 7,249,901 | 7,477,987 |
| 11/478,590 | 7,503,493 | 7,156,289 | 7,178,718 | 7,225,979 |
| 11/084,796 | 11/084,742 | 11/084,806 | 09/575,197 | 7,079,712 |
| 6,825,945 | 7,330,974 | 6,813,039 | 7,190,474 | 6,987,506 |
| 6,824,044 | 7,038,797 | 6,980,318 | 6,816,274 | 7,102,772 |
| 7,350,236 | 6,681,045 | 6,678,499 | 6,679,420 | 6,963,845 |
| 6,976,220 | 6,728,000 | 7,110,126 | 7,173,722 | 6,976,035 |
| 6,813,558 | 6,766,942 | 6,965,454 | 6,995,859 | 7,088,459 |
| 6,720,985 | 7,286,113 | 6,922,779 | 6,978,019 | 6,847,883 |
| 7,131,058 | 7,295,839 | 7,406,445 | 09/693,690 | 6,959,298 |
| 6,973,450 | 7,150,404 | 6,965,882 | 7,233,924 | 09/575,181 |
| 09/722,174 | 7,175,079 | 7,162,259 | 6,718,061 | 7,464,880 |
| 7,012,710 | 6,825,956 | 7,451,115 | 7,222,098 | 10/291,825 |
| 7,263,508 | 7,031,010 | 6,972,864 | 6,862,105 | 7,009,738 |
| 6,989,911 | 6,982,807 | 7,518,756 | 6,829,387 | 6,714,678 |
| 6,644,545 | 6,609,653 | 6,651,879 | 10/291,555 | 7,293,240 |
| 7,467,185 | 7,415,668 | 7,044,363 | 7,004,390 | 6,867,880 |
| 7,034,953 | 6,987,581 | 7,216,224 | 7,506,153 | 7,162,269 |
| 7,162,222 | 7,290,210 | 7,293,233 | 7,293,234 | 6,850,931 |
| 6,865,570 | 6,847,961 | 10/685,523 | 10/685,583 | 7,162,442 |
| 10/685,584 | 7,159,784 | 10/804,034 | 7,404,144 | 6,889,896 |
| 10/831,232 | 7,174,056 | 6,996,274 | 7,162,088 | 7,388,985 |
| 7,417,759 | 7,362,463 | 7,259,884 | 7,167,270 | 7,388,685 |
| 6,986,459 | 10/954,170 | 7,181,448 | 10/981,626 | 10/981,616 |
| 7,324,989 | 7,231,293 | 7,174,329 | 7,369,261 | 7,295,922 |
| 7,200,591 | 11/020,106 | 11/020,260 | 11/020,321 | 11/020,319 |
| 7,466,436 | 7,347,357 | 11/051,032 | 7,382,482 | 11/107,944 |
| 7,446,893 | 11/082,940 | 11/082,815 | 7,389,423 | 7,401,227 |
| 6,991,153 | 6,991,154 | 11/124,256 | 11/123,136 | 7,322,524 |

-continued

| | | | | |
|---|---|---|---|---|
| 11/202,252 | 7,408,670 | 7,466,439 | 11/206,778 | 11/203,242 |
| 11/222,977 | 7,327,485 | 7,428,070 | 7,225,402 | 11/349,143 |
| 11/442,428 | 7,271,931 | 11/520,170 | 7,068,382 | 7,007,851 |
| 6,957,921 | 6,457,883 | 7,044,381 | 11/203,205 | 7,094,910 |
| 7,091,344 | 7,122,685 | 7,038,066 | 7,099,019 | 7,062,651 |
| 6,789,194 | 6,789,191 | 10/900,129 | 7,278,018 | 7,360,089 |
| 7,526,647 | 7,467,416 | 11/331,109 | 6,644,642 | 6,502,614 |
| 6,622,999 | 6,669,385 | 6,827,116 | 7,011,128 | 7,416,009 |
| 6,549,935 | 6,987,573 | 6,727,996 | 6,591,884 | 6,439,706 |
| 6,760,119 | 7,295,332 | 7,064,851 | 6,826,547 | 6,290,349 |
| 6,428,155 | 6,785,016 | 6,831,682 | 6,741,871 | 6,927,871 |
| 6,980,306 | 6,965,439 | 6,840,606 | 7,036,918 | 6,977,746 |
| 6,970,264 | 7,068,389 | 7,093,991 | 7,190,491 | 7,511,847 |
| 10/932,044 | 10/962,412 | 7,177,054 | 7,364,282 | 10/965,733 |
| 10/965,933 | 10/974,742 | 7,468,809 | 7,180,609 | 10/986,375 |
| 7,466,438 | 7,292,363 | 7,515,292 | 7,414,741 | 7,202,959 |
| 6,982,798 | 6,870,966 | 6,822,639 | 6,474,888 | 6,627,870 |
| 6,724,374 | 6,788,982 | 7,263,270 | 6,788,293 | 6,946,672 |
| 6,737,591 | 7,091,960 | 7,369,265 | 6,792,165 | 7,105,753 |
| 6,795,593 | 6,980,704 | 6,768,821 | 7,132,612 | 7,041,916 |
| 6,797,895 | 7,015,901 | 7,289,882 | 7,148,644 | 10/778,056 |
| 10/778,058 | 10/778,060 | 7,515,186 | 10/778,063 | 10/778,062 |
| 10/778,061 | 10/778,057 | 7,096,199 | 7,286,887 | 7,400,937 |
| 7,474,930 | 7,324,859 | 7,218,978 | 7,245,294 | 7,277,085 |
| 7,187,370 | 10/917,436 | 10/943,856 | 10/919,379 | 7,019,319 |
| 10/943,878 | 10/943,849 | 7,043,096 | 7,148,499 | 7,463,250 |
| 11/155,556 | 11/155,557 | 11/193,481 | 11/193,435 | 11/193,482 |
| 11/193,479 | 7,336,267 | 7,388,221 | 11/298,474 | 11/488,832 |
| 11/495,814 | 11/495,823 | 11/495,822 | 7,523,672 | 11/495,820 |
| 7,055,739 | 7,233,320 | 6,830,196 | 6,832,717 | 7,182,247 |
| 7,120,853 | 7,082,562 | 6,843,420 | 10/291,718 | 6,789,731 |
| 7,057,608 | 6,766,944 | 6,766,945 | 7,289,103 | 7,412,651 |
| 7,299,969 | 7,264,173 | 10/409,864 | 7,108,192 | 10/537,159 |
| 7,111,791 | 7,077,333 | 6,983,878 | 10/786,631 | 7,134,598 |
| 7,431,219 | 6,929,186 | 6,994,264 | 7,017,826 | 7,014,123 |
| 7,134,601 | 7,150,396 | 7,469,830 | 7,017,823 | 7,025,276 |
| 7,284,701 | 7,080,780 | 7,376,884 | 7,334,739 | 10/492,169 |
| 7,469,062 | 7,359,551 | 7,444,021 | 7,308,148 | 10/502,575 |
| 10/531,229 | 10/531,733 | 10/683,040 | 10/510,391 | 10/510,392 |
| 7,526,128 | 6,957,768 | 7,456,820 | 7,170,499 | 7,106,888 |
| 7,123,239 | 6,982,701 | 6,982,703 | 7,227,527 | 6,786,397 |
| 6,947,027 | 6,975,299 | 7,139,431 | 7,048,178 | 7,118,025 |
| 6,839,053 | 7,015,900 | 7,010,147 | 7,133,557 | 6,914,593 |
| 7,437,671 | 6,938,826 | 7,278,566 | 7,123,245 | 6,992,662 |
| 7,190,346 | 7,417,629 | 7,468,724 | 7,382,354 | 11/075,917 |
| 7,221,781 | 11/102,843 | 7,263,225 | 7,287,688 | 10/727,181 |
| 10/727,162 | 7,377,608 | 7,399,043 | 7,121,639 | 7,165,824 |
| 7,152,942 | 10/727,157 | 7,181,572 | 7,096,137 | 7,302,592 |
| 7,278,034 | 7,188,282 | 10/727,159 | 10/727,180 | 10/727,179 |
| 10/727,192 | 10/727,274 | 10/727,164 | 7,523,111 | 10/727,198 |
| 10/727,158 | 10/754,536 | 10/754,938 | 10/727,227 | 10/727,160 |
| 10/934,720 | 7,171,323 | 7,278,697 | 7,360,131 | 7,519,772 |
| 7,328,115 | 7,369,270 | 6,795,215 | 7,070,098 | 7,154,638 |
| 6,805,419 | 6,859,289 | 6,977,751 | 6,398,332 | 6,394,573 |
| 6,622,923 | 6,747,760 | 6,921,144 | 10/884,881 | 7,092,112 |
| 7,192,106 | 7,457,001 | 7,173,739 | 6,986,560 | 7,008,033 |
| 11/148,237 | 7,222,780 | 7,270,391 | 7,525,677 | 7,388,689 |
| 11/482,981 | 7,195,328 | 7,182,422 | 7,374,266 | 7,427,117 |
| 7,448,707 | 7,281,330 | 10/854,503 | 7,328,956 | 10/854,509 |
| 7,188,928 | 7,093,989 | 7,377,609 | 10/854,495 | 10/854,498 |
| 10/854,511 | 7,390,071 | 10/854,525 | 10/854,526 | 10/854,516 |
| 7,252,353 | 10/854,515 | 7,267,417 | 10/854,505 | 7,517,036 |
| 7,275,805 | 7,314,261 | 10/854,490 | 7,281,777 | 7,290,852 |
| 7,484,831 | 10/854,523 | 10/854,527 | 10/854,524 | 10/854,520 |
| 10/854,514 | 10/854,519 | 10/854,513 | 10/854,499 | 10/854,501 |
| 7,266,661 | 7,243,193 | 10/854,518 | 10/934,628 | 7,163,345 |
| 7,322,666 | 11/544,764 | 11/544,765 | 11/544,772 | 11/544,773 |
| 11/544,774 | 11/544,775 | 7,425,048 | 11/544,766 | 11/544,767 |
| 7,384,128 | 11/544,770 | 11/544,769 | 11/544,777 | 7,425,047 |
| 7,413,288 | 7,465,033 | 7,452,055 | 7,470,002 | 11/293,833 |
| 7,475,963 | 7,448,735 | 7,465,042 | 7,448,739 | 7,438,399 |
| 11/293,794 | 7,467,853 | 7,461,922 | 7,465,020 | 11/293,830 |
| 7,461,910 | 11/293,828 | 7,270,494 | 11/293,823 | 7,475,961 |
| 11/293,831 | 11/293,815 | 11/293,819 | 11/293,818 | 11/293,817 |
| 11/293,816 | 11/482,978 | 7,448,734 | 7,425,050 | 7,364,263 |
| 7,201,468 | 7,360,868 | 7,234,802 | 7,303,255 | 7,287,846 |
| 7,156,511 | 10/760,264 | 7,258,432 | 7,097,291 | 10/760,222 |
| 10/760,248 | 7,083,273 | 7,367,647 | 7,374,355 | 7,441,880 |
| 10/760,205 | 10/760,206 | 7,513,598 | 10/760,270 | 7,198,352 |

-continued

| | | | | |
|---|---|---|---|---|
| 7,364,264 | 7,303,251 | 7,201,470 | 7,121,655 | 7,293,861 |
| 7,232,208 | 7,328,985 | 7,344,232 | 7,083,272 | 7,311,387 |
| 11/014,764 | 11/014,763 | 7,331,663 | 7,360,861 | 7,328,973 |
| 7,427,121 | 7,407,262 | 7,303,252 | 7,249,822 | 11/014,762 |
| 7,311,382 | 7,360,860 | 7,364,257 | 7,390,075 | 7,350,896 |
| 7,429,096 | 7,384,135 | 7,331,660 | 7,416,287 | 7,488,052 |
| 7,322,684 | 7,322,685 | 7,311,381 | 7,270,405 | 7,303,268 |
| 7,470,007 | 7,399,072 | 7,393,076 | 11/014,750 | 11/014,749 |
| 7,249,833 | 7,524,016 | 7,490,927 | 7,331,661 | 7,524,043 |
| 7,300,140 | 7,357,492 | 7,357,493 | 11/014,766 | 7,380,902 |
| 7,284,816 | 7,284,845 | 7,255,430 | 7,390,080 | 7,328,984 |
| 7,350,913 | 7,322,671 | 7,380,910 | 7,431,424 | 7,470,006 |
| 11/014,732 | 7,347,534 | 7,441,865 | 7,469,989 | 7,367,650 |
| 7,469,990 | 7,441,882 | 11/293,822 | 7,357,496 | 7,467,863 |
| 7,431,440 | 7,431,443 | 11/293,811 | 7,524,023 | 7,513,603 |
| 7,467,852 | 7,465,045 | 11/482,982 | 11/482,983 | 11/482,984 |
| 11/495,818 | 11/495,819 | 6,454,482 | 6,808,330 | 6,527,365 |
| 6,474,773 | 6,550,997 | 7,093,923 | 6,957,923 | 7,131,724 |
| 7,396,177 | 7,168,867 | 7,125,098 | 7,413,363 | 7,188,930 |

The disclosures of all of these co-pending patents/patent applications are incorporated herein by reference. Some patent applications are temporarily identified by their docket number.

BACKGROUND OF THE INVENTION

IR absorbing dyes have numerous applications, such as optical recording systems, thermal writing displays, laser filters, infrared photography, medical applications and printing. Typically, it is desirable for the dyes used in these applications to have strong absorption in the near-IR at the emission wavelengths of semiconductor lasers (e.g. between about 700 and 2000 nm, preferably between about 700 and 1000 nm). In optical recording technology, for example, gallium aluminium arsenide (GaAlAs) and indium phosphide (InP) diode lasers are widely used as light sources.

Another important application of IR dyes is in inks, such as printing inks. The storage and retrieval of digital information in printed form is particularly important. A familiar example of this technology is the use of printed, scannable bar codes. Bar codes are typically printed onto tags or labels associated with a particular product and contain information about the product, such as its identity, price etc. Bar codes are usually printed in lines of visible black ink, and detected using visible light from a scanner. The scanner typically comprises an LED or laser (e.g. a HeNe laser, which emits light at 633 nm) light source and a photocell for detecting reflected light. Black dyes suitable for use in barcode inks are described in, for example, WO03/074613.

However, in other applications of this technology (e.g. security tagging) it is desirable to have a barcode, or other intelligible marking, printed with an ink that is invisible to the unaided eye, but which can be detected under UV or IR light.

An especially important application of detectable invisible ink is in automatic identification systems, and especially "netpage" and "Hyperlabel™" systems. Netpage systems are described in the patents and patent applications the details of which are provided in the cross reference section above.

The disclosures of all of these co-pending patents/patent applications are incorporated herein by reference. Some patent applications are temporarily identified by their docket number. These will be replaced by the corresponding application number when available.

In general, the netpage system relies on the production of, and human interaction with, netpages. These are pages of text, graphics and images printed on ordinary paper, but which work like interactive web pages. Information is encoded on each page using ink which is substantially invisible to the unaided human eye. The ink, however, and thereby the coded data, can be sensed by an optically imaging pen and transmitted to the netpage system.

Active buttons and hyperlinks on each page may be clicked with the pen to request information from the network or to signal preferences to a network server. In some forms, text written by hand on a netpage may be automatically recognized and converted to computer text in the netpage system, allowing forms to be filled in. In other forms, signatures recorded on a netpage may be automatically verified, allowing e-commerce transactions to be securely authorized.

Netpages are the foundation on which a netpage network is built. They may provide a paper-based user interface to published information and interactive services.

A netpage consists of a printed page (or other surface region) invisibly tagged with references to an online description of the page. The online page description is maintained persistently by a netpage page server. The page description describes the visible layout and content of the page, including text, graphics and images. It also describes the input elements on the page, including buttons, hyperlinks, and input fields. A netpage allows markings made with a netpage pen on its surface to be simultaneously captured and processed by the netpage system.

Multiple netpages can share the same page description. However, to allow input through otherwise identical pages to be distinguished, each netpage is assigned a unique page identifier. This page ID has sufficient precision to distinguish between a very large number of netpages.

In a preferred form suitable for use with the Applicant's digital inkjet printers, each reference to the page description is encoded in a printed tag. The tag identifies the unique page on which it appears, and thereby indirectly identifies the page description. The tag also identifies its own position on the page.

Tags are printed in infrared-absorptive ink on any substrate which is infrared-reflective, such as ordinary paper. Near-infrared wavelengths are invisible to the human eye but are easily sensed by a solid-state image sensor with an appropriate filter.

A tag is sensed by an area image sensor in the netpage pen, and the tag data is transmitted to the netpage system via the nearest netpage printer. The pen is wireless and communicates with the netpage printer via a short-range radio link. Tags are sufficiently small and densely arranged that the pen can reliably image at least one tag even on a single click on the page. It is important that the pen recognize the page ID and position on every interaction with the page, since the interaction is stateless. Tags are error-correctably encoded to make them partially tolerant to surface damage.

The netpage page server maintains a unique page instance for each printed netpage, allowing it to maintain a distinct set of user-supplied values for input fields in the page description for each printed netpage.

Hyperlabel™ is a trade mark of Silverbrook Research Pty Ltd, Australia. In a preferred form of Hyperlabel™ which is suitable for use with the Applicant's digital inkjet printers, an invisible (e.g. infrared) tagging scheme uniquely identifies a product item. This has the significant advantage that it allows the entire surface of a product to be tagged, or a significant portion thereof, without impinging on the graphic design of the product's packaging or labeling. If the entire surface of a product is tagged ("omnitagged"), then the orientation of the product does not affect its ability to be scanned i.e. a significant part of the line-of-sight disadvantage of visible barcodes is eliminated. Furthermore, if the tags are compact and massively replicated ("omnitags"), then label damage no longer prevents scanning.

Thus, Hyperlabel tagging consists of covering a large portion of the surface of a product with optically-readable invisible tags. When the tags utilize reflection or absorption in the infrared spectrum, they are referred to as infrared identification (IRID) tags. Each Hyperlabel™ tag may uniquely identify the product on which it appears. Each tag also optionally identifies its own position on the surface of the product item, to provide the downstream consumer benefits of netpage interactivity.

Hyperlabels™ are typically applied during product manufacture and/or packaging using digital printers, preferably inkjet printers. These may be add-on infrared printers, which print the tags after the text and graphics have been printed by other means, or integrated colour and infrared printers which print the tags, text and graphics simultaneously.

Hyperlabels™ can be detected using similar technology to barcodes, except using a light source having an appropriate near-IR frequency. The light source may be a laser (e.g. a GaAlAs laser, which emits light at 830 nm) or it may be an LED.

In our copending U.S. application Ser. Nos. 11/488,162, 11/488,163, 11/488,164 and 11/488,167 all filed 18 Jul. 2006 (the contents of which are all incorporated herein by cross-reference), we described an alternative to printing Hyperlabel™ tags using a digital printer. In this alternative system, tags are printed by an analog (e.g. offset) printing process and the product item carries an independent identifier and/or a layout identifier encoded into the tags. This alternative system has the advantage that the tags are not required to uniquely identify each individual product item and can therefore be printed by an analog printing process, which prints multiple batches of identical tags onto a media web.

It would therefore be desirable to provide an IR-absorbing dye, suitable for formulation into an analog printing ink. Typically, offset printing inks are oil-based inks.

It would be further desirable for the dye to exhibit properties compatible with netpage and Hyperlabel™ systems, such as intense absorption in the near infra-red region (e.g. 700 to 1000 nm); zero or low intensity visible absorption; good lightfastness; good thermal stability; zero or low toxicity; and low-cost manufacture.

Some IR dyes are commercially available from various sources, such as Epolin Products, Fujifilm Imaging Colorants and H.W. Sands Corp.

In addition, the prior art describes various IR dyes. U.S. Pat. No. 5,460,646, for example, describes an infrared printing ink comprising a colorant, a vehicle and a solvent, wherein the dye is a silicon (IV) 2,3-naphthalocyanine bis-trialkylsilyloxide.

U.S. Pat. No. 5,282,894 describes a solvent-based printing ink comprising a metal-free phthalocyanine, a complexed phthalocyanine, a metal-free naphthalocyanine, a complexed naphthalocyanine, a nickel dithiolene, an aminium compound, a methine compound or an azulenesquaric acid.

However, prior art oil-based inks tend to be highly colored and unsuitable for netpage and Hyperlabel™ applications.

SUMMARY OF THE INVENTION

In a first aspect, there is provided an IR-absorbing phthalocyanine dye suitable for formulation in a solvent-based or oil-based ink vehicle, the phthalocyanine comprising one or more sulfonate groups, wherein a counterion of at least one sulfonate group is a phosphonium cation.

Optionally, the phthalocyanine comprises a plurality of sulfonate groups with a corresponding plurality of phosphonium cations.

Optionally, the phthalocyanine is a naphthalocyanine.

Optionally, each phosphonium cation is of formula: $P^+(R^m)(R^n)(R^s)(R^t)$, wherein each of $R^m$, $R^n$, $R^s$ and $R^t$ is independently selected from $C_{1-30}$ alkyl, $C_{5-12}$ aryl and $C_{5-30}$ arylalkyl.

Optionally, at least one of $R^m$, $R^n$, $R^s$ and $R^t$ contains more than 4 carbon atoms.

Optionally, the dye is of formula (I):

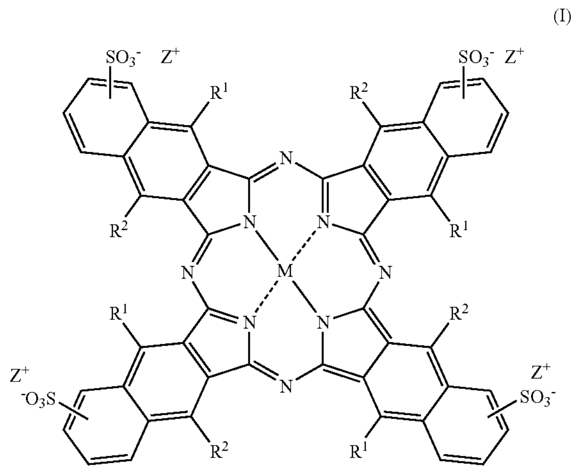

wherein

M is $Ga(A^1)$;

$A^1$ is an axial ligand selected from —OH, halogen, $—OR^3$, $—OC(O)R^4$ or $—O(CH_2CH_2O)_eR^e$ wherein e is an integer from 2 to 10 and $R^e$ is H, $C_{1-8}$ alkyl or $C(O)C_{1-8}$ alkyl;

$R^1$ and $R^2$ may be the same or different and are selected from hydrogen or $C_{1-12}$ alkoxy;

$R^3$ is selected from $C_{1-12}$ alkyl, $C_{5-12}$ aryl, $C_{5-12}$ arylalkyl or $Si(R^x)(R^y)(R^z)$;

$R^4$ is selected from $C_{1-12}$ alkyl, $C_{5-12}$ aryl or $C_{5-12}$ arylalkyl;

$R^x$, $R^y$ and $R^z$ may be the same or different and are selected from $C_{1-12}$ alkyl, $C_{5-12}$ aryl, $C_{5-12}$ arylalkyl, $C_{1-12}$ alkoxy, $C_{5-12}$ aryloxy or $C_{5-12}$ arylalkoxy; and $Z^+$ is a phosphonium cation.

Optionally, $Z^+$ is of formula: $P^+(R^m)(R^n)(R^5)(R^t)$, wherein each of $R^m$, $R^1$, $R^s$ and $R^t$ is independently selected from $C_{1-30}$ alkyl, $C_{5-12}$ aryl and $C_{5-30}$ arylalkyl.

Optionally, at least one of $R^m$, $R^n$, $R^s$ and $R^t$ contains more than 4 carbon atoms. Optionally, at least one of $R^m$, $R^n$, $R^s$ and $R^t$ contains 6 or more carbon atoms.

Optionally, at least three of $R^m$, $R^n$, $R^s$ and $R^t$ contain more than 4 carbon atoms. Optionally, at least three of $R^m$, $R^n$, $R^s$ and $R^t$ contain 6 or more carbon atoms.

Optionally, at least three of $R^m$, $R^n$, $R^s$ and $R^t$ are independently selected from a $C_{6-30}$ alkyl group. Optionally, at least one of $R^m$, $R^n$, $R^s$ and $R^t$ is independently selected from a $C_{10-30}$ alkyl group.

Optionally, $R^1$ and $R^2$ are both hydrogen.

Optionally, M is Ga(OH).

In a second aspect, there is provided a solvent-based or oil-based ink comprising a dye as defined above.

In a third aspect, there is provided an analog printer, or a module thereof, comprising an ink supply, a printing plate and means for disposing ink from the ink supply onto the plate, wherein the ink comprises a dye as defined above.

In a fourth aspect, there is provided a substrate having a dye as defined above disposed thereon or therein.

Optionally, the substrate is a label, packaging or surface of a product item.

In a fifth aspect, there is provided a system for interacting with a coded substrate, the system comprising:

a substrate having human-readable information and machine-readable coded data disposed thereon or therein; and a sensing device for reading the machine-readable coded data, wherein the coded data comprises a dye as defined above.

In a sixth aspect, there is provided a method of initiating a requested action in a computer system via a printed substrate, the substrate containing human-readable information and machine-readable coded data, the method including the steps of:

positioning a sensing device in an operative position relative to the substrate;

sensing at least some of the coded data;

generating indicating data in the sensing device using at least some of the sensed coded data, the indicating data enabling the computer to identify the requested action; and sending the indicating data to the computer system, wherein the coded data comprises a dye as defined above.

In a seventh aspect, there is provided a method of interacting with a product item, the product item having a printed surface containing human-readable information and machine-readable coded data, the method including the steps of:

positioning a sensing device in an operative position relative to the surface;

sensing at least some of the coded data;

generating indicating data in the sensing device using at least some of the sensed coded data, the indicating data enabling the computer to identify a parameter relating to the interaction; and sending the indicating data to the computer system, wherein the coded data comprises a dye as defined above.

DETAILED DESCRIPTION

IR-Absorbing Dye

Figure 1:
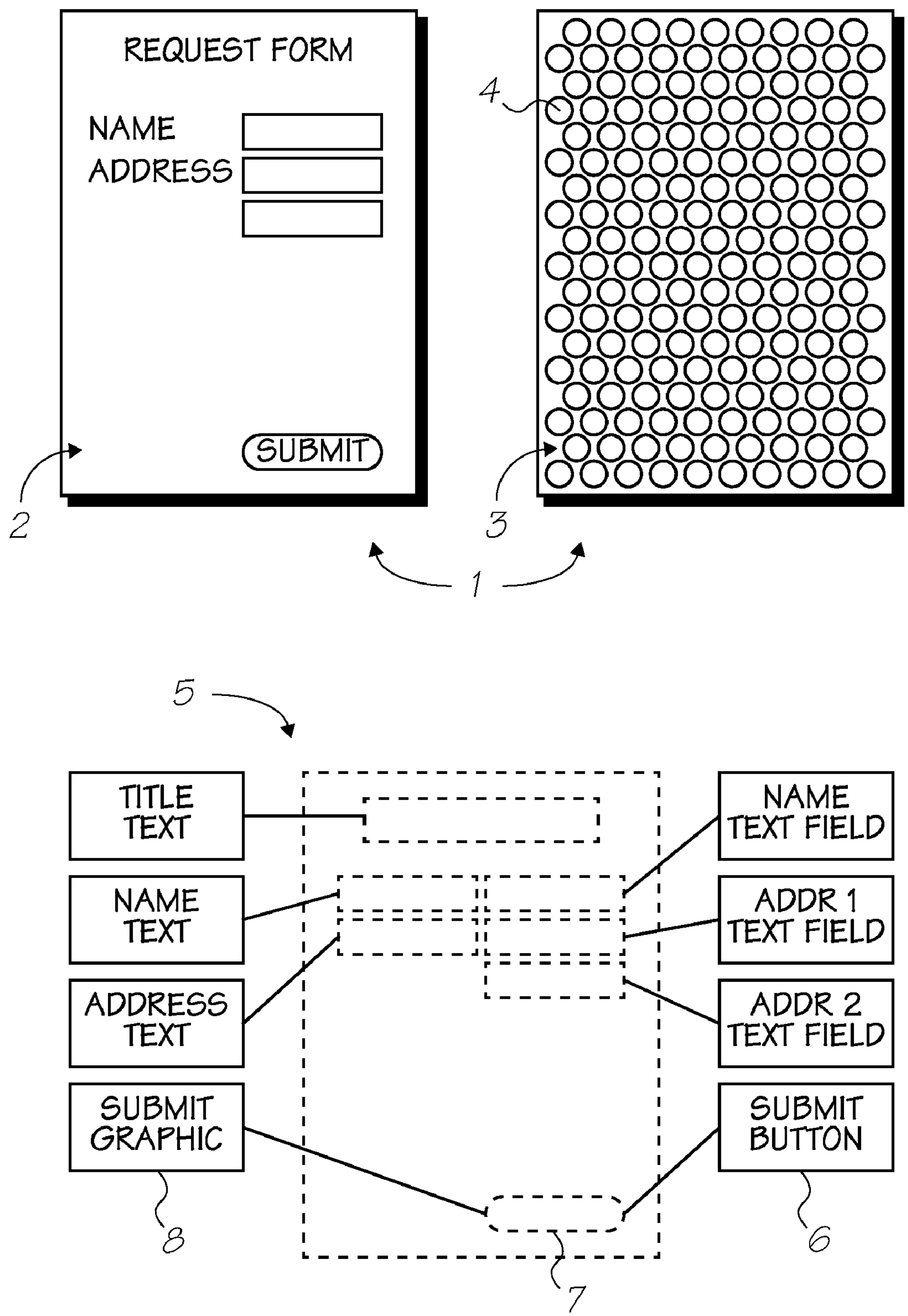
FIG. 1 is a schematic of a the relationship between a sample printed netpage and its online page description.

As used herein, the term "phthalocyanine" refers to any compound belonging to the general class of macrocyclic phthalocyanines, and includes naphthalocyanines, quinolinephthalocyanines etc, as well as substituted derivatives thereof.

As used herein, the term "IR-absorbing dye" means a substance, which absorbs infrared radiation and which is therefore suitable for detection by an infrared sensor. Preferably, the IR-absorbing dye absorbs in the near infrared region, and preferably has a $\lambda_{max}$ in the range of 700 to 1000 nm, more preferably 750 to 900 nm, more preferably 780 to 850 nm. Dyes having a $\lambda_{max}$ in this range are particularly suitable for detection by semiconductor lasers, such as a gallium aluminium arsenide diode laser.

Formulations according to the present invention have the advantageous features of: low visibility and suitability for formulation into solvent-based or oil-based inks. Accordingly, the dyes of the present invention may be suitable for use in netpage and Hyperlabel™ applications, where coded data is printed by an analog (e.g. offset) printing process, as described in our copending applications HYG019, HYG020, HYG021 and HYG022, the contents of which are herein incorporated by reference.

Hitherto, phosphonium salts of sulfonated phthalocyanines had not been proposed as IR-absorbing dyes suitable for formulation into solvent-based or oil-based inks. Traditionally, the inherent hydrophobicity of the phthalocyanine macrocycle had been exploited as a means for solubilizing phthalocyanines into solvents or oils. However, in the present invention, the phthalocyanine is sulfonated and the counterion provides the hydrophobicity necessary for solubilization in oils. One advantage of this approach is that complementary water-soluble and oil-soluble dyes may be manufactured from a common sulfonic acid intermediate.

A further advantage is that the complementary water-soluble and oil-soluble dyes have the same chromophore and therefore have similar $\lambda_{max}$. IR dyes are usually designed for use with a specific IR sensor which has maximum sensitivity to a particular wavelength. It is therefore desirable to produce a suite of complementary aqueous-based and oil-based dyes, printable by digital (e.g. inkjet) or analog (e.g. offset) processes, which have the same $\lambda_{max}$ and optimized for use with the same IR sensor. It will be readily appreciated that the oil- and solvent-soluble dyes described below in the Examples are complementary with the water-soluble dyes described in our earlier applications IRB011US and IRB017US, the contents of which are incorporated herein by reference. The dyes each share the same sulfonated gallium naphthalocyanine chromophore and therefore have similar absorption characteristics.

A significant advantage of IR dyes according to the present invention is their low visibility. This low visibility is believed to be a result of reduced π-π stacking between adjacent molecules. The phosphonium cation is believed to interrupt aggregation, thereby providing a greater monomer component with a sharper Q-band. A sharper Q-band in the IR region generally provides less absorption in the visible region, and therefore lower overall visibility when printed.

Whilst bulky phosphonium cations are generally preferred, it is understood by the present inventors that, given the large atomic size of phosphorus, any phosphonium cation would interrupt aggregation at least to some extent and produce less visible dyes. Hence, $R^m$, $R^n$, $R^s$ and $R^t$ may be selected from a range of alkyl and aryl groups. However, alkyl and aryl groups having more than 4 or more than 5 carbon atoms are generally preferred. Typically, at least one of $R^m$, $R^n$, $R^s$ or $R^t$ has more than 10 carbon atoms. Compared with other counterions (e.g. metal ions), the phosphonium cation provides dyes having a surprisingly low visible absorption as well as excellent solubility in standard offset ink vehicles.

In the most general form of the present invention, the phthalocyanine dye may be metal-free or may comprise a central metal atom moiety M. Optionally, M is selected from $Si(A^1)(A^2)$, $Ge(A^1)(A^2)$, $Ga(A^1)$, Mg, $Al(A^1)$, TiO, $Ti(A^1)(A^2)$, ZrO, $Zr(A^1)(A^2)$, VO, $V(A^1)(A^2)$, Mn, $Mn(A^1)$, Fe, $Fe(A^1)$, Co, Ni, Cu, Zn, Sn, $Sn(A^1)(A^2)$, Pb, $Pb(A^1)(A^2)$, Pd and Pt. Phthalocyanines having a range of central metal atom moieties are well known in the literature (see, for example, Aldrich Catalogue).

Optionally, M is selected from $Si(A^1)(A^2)$, $Ge(A^1)(A^2)$, $Ga(A^1)$, $Al(A^1)$, VO, Mn, $Mn(A^1)$, Cu, Zn, Sn, and $Sn(A^1)(A^2)$.

Optionally, M is $Ga(A^1)$.

$A^1$ and $A^2$ are axial ligands, which may be the same or different. Optionally, $A^1$ and $A^2$ and are selected from —OH, halogen or $—OR^3$. Optionally, $A^1$ and $A^2$ may be $—OC(O)R^4$ or $—O(CH_2CH_2O)_eR^e$ wherein e is an integer from 2 to 10 and $R^e$ is H, $C_{1-8}$ alkyl or $C(O)C_{1-8}$ alkyl.

$R^3$ may be $C_{1-12}$ alkyl, $C_{5-12}$ aryl, $C_{5-12}$ arylalkyl or $Si(R^x)(R^y)(R^z)$.

$R^4$ may be $C_{1-12}$ alkyl, $C_{5-12}$ aryl or $C_{5-12}$ arylalkyl.

$R^x$, $R^y$ and $R^z$ may be the same or different and are selected from $C_{1-12}$ alkyl, $C_{5-12}$ aryl, $C_{5-12}$ arylalkyl, $C_{1-12}$ alkoxy, $C_{5-12}$ aryloxy or $C_{5-12}$ arylalkoxy.

Typically $A^1$ is a hydroxyl group (—OH). Alternatively, $A^1$ may be selected or modified to impart specific properties onto the dye molecule. $A^1$ may be selected to add axial steric bulk to the dye molecule, thereby further reducing cofacial interactions between adjacent dye molecules.

The term "aryl" is used herein to refer to an aromatic group, such as phenyl, naphthyl or triptycenyl. $C_{6-12}$ aryl, for example, refers to an aromatic group having from 6 to 12 carbon atoms, excluding any substituents. The term "arylene", of course, refers to divalent groups corresponding to the monovalent aryl groups described above. Any reference to aryl implicitly includes arylene, where appropriate.

Unless specifically stated otherwise, aryl groups may be optionally substituted with 1, 2, 3, 4 or 5 of the substituents described below. The optional substituent(s) are independently selected from $C_{1-8}$ alkyl, $C_{1-8}$ alkoxy, $—(OCH_2CH_2)_dOR^d$ (wherein d is an integer from 2 to 5000 and $R^d$ is H, $C_{1-8}$ alkyl or $C(O)C_{1-8}$ alkyl), cyano, halogen, amino, hydroxyl, thiol, $—SR^v$, $—NR^uR^v$, nitro, phenyl, phenoxy, $—CO_2R^v$, $—C(O)R^v$, $—OCOR^v$, $—SO_2R^v$, $—OSO_2R^v$, $—SO_2OR^v$, $—NHC(O)R^v$, $—CONR^uR^v$, $—CONR^uR^v$, $—SO_2NR^uR^v$, wherein $R^s$ and $R^V$ are independently selected from hydrogen, $C_{1-12}$ alkyl, phenyl or phenyl-$C_{1-8}$ alkyl (e.g. benzyl). Where, for example, a group contains more than one substituent, different substituents can have different $R^u$ or $R^v$ groups. For example, a naphthyl group may be substituted with three substituents: $—SO_2NHPh$, $—CO_2Me$ group and $—NH_2$.

The term "alkyl" is used herein to refer to alkyl groups in both straight and branched forms, The alkyl group may be interrupted with 1, 2 or 3 heteroatoms selected from O, N or S. The alkyl group may also be interrupted with 1, 2 or 3 double and/or triple bonds. However, the term "alkyl" usually refers to alkyl groups having no heteroatom interruptions or double or triple bond interruptions. Where "alkenyl" groups are specifically mentioned, this is not intended to be construed as a limitation on the definition of "alkyl" above.

The term "alkyl" also includes halogenoalkyl groups. A $C_{1-12}$ alkyl group may, for example, have up to 5 hydrogen atoms replaced by halogen atoms. For example, the group $—OC(O)C_{1-12}$ alkyl specifically includes $—OC(O)CF_3$.

Where reference is made to, for example, $C_{1-30}$ alkyl, it is meant the alkyl group may contain any number of carbon atoms between 1 and 30. Unless specifically stated otherwise, any reference to "alkyl" means $C_{1-30}$ alkyl.

The term "alkyl" also includes cycloalkyl groups. As used herein, the term "cycloalkyl" includes cycloalkyl, polycycloalkyl, and cycloalkenyl groups, as well as combinations of these with linear alkyl groups, such as cycloalkylalkyl groups. The cycloalkyl group may be interrupted with 1, 2 or 3 heteroatoms selected from O, N or S. However, the term "cycloalkyl" usually refers to cycloalkyl groups having no heteroatom interruptions. Examples of cycloalkyl groups include cyclopentyl, cyclohexyl, cyclohexenyl, cyclohexylmethyl and adamantyl groups.

The term "arylalkyl" refers to groups such as benzyl, phenylethyl and naphthylmethyl.

The term "halogen" or "halo" is used herein to refer to any of fluorine, chlorine, bromine and iodine. Usually, however, halogen refers to chlorine or fluorine substituents.

Any chiral compounds described herein have not been given stereo-descriptors. However, when compounds may exist in stereoisomeric forms, then all possible stereoisomers and mixtures thereof are included (e.g. enantiomers, diastereomers and all combinations including racemic mixtures etc.).

Likewise, when compounds may exist in a number of regioisomeric forms, then all possible regioisomers and mixtures thereof are included.

For the avoidance of doubt, the term "a" (or "an"), in phrases such as "comprising a", means "at least one" and not "one and only one". Where the term "at least one" is specifically used, this should not be construed as having a limitation on the definition of "a".

Throughout the specification, the term "comprising", or variations such as "comprise" or "comprises", should be construed as including a stated element, integer or step, but not excluding any other element, integer or step.

Inks

The present invention also provides a solvent-based or an oil-based ink. Optionally, the ink is suitable for analog printing, such as offset printing. However, it will be appreciated that the ink may also be suitable for digital inkjet printheads, which do not require an aqueous-based ink for bubble generation. Examples of such printheads are piezoelectric printheads and the Applicant's thermal bend actuator printheads described in more detail below.

Solvent-based and oil-based ink formulations suitable for analog printing will be well known to the person skilled in the art. Such printing inks are typically comprised of four material categories, including: (a) dyes, which include pigments, toners and dyes; (b) vehicles, or varnishes, which act as carriers for the dyes during the printing operation, and bind the dyes to the substrate upon drying; (c) solvents, which primarily assist in the formation of the vehicle, and reduce ink viscosity; and (d) additives, which influence the printability, film characteristics, drying speed, and end-use properties.

Printers

Analog printers, such as offset printers, have been known in the art for decades and will be part of the skilled person's common general knowledge.

As already mentioned, solvent-based inks described herein may be used with the Applicant's thermal bend actuator inkjet printheads. In the thermal bend actuator, there is typically provided a nozzle arrangement having a nozzle chamber containing ink and a thermal bend actuator connected to a paddle positioned within the chamber. The thermal actuator device is actuated so as to eject ink from the nozzle chamber. The preferred embodiment includes a particular thermal bend actuator which includes a series of tapered portions for providing conductive heating of a conductive trace. The actuator is connected to the paddle via an arm received through a slotted wall of the nozzle chamber. The actuator arm has a mating shape so as to mate substantially with the surfaces of the slot in the nozzle chamber wall.

Figure 17A:
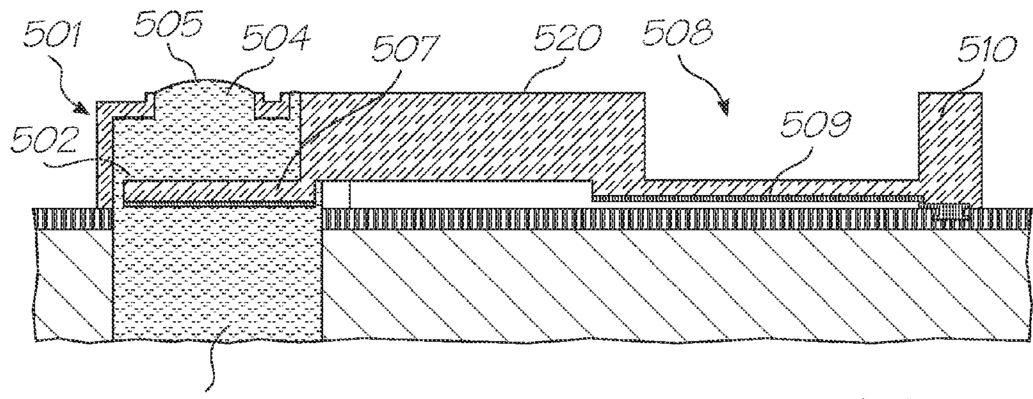
FIGS. 17(A) to 17(C) show the basic operational principles of a thermal bend actuator.
Figure 17B:
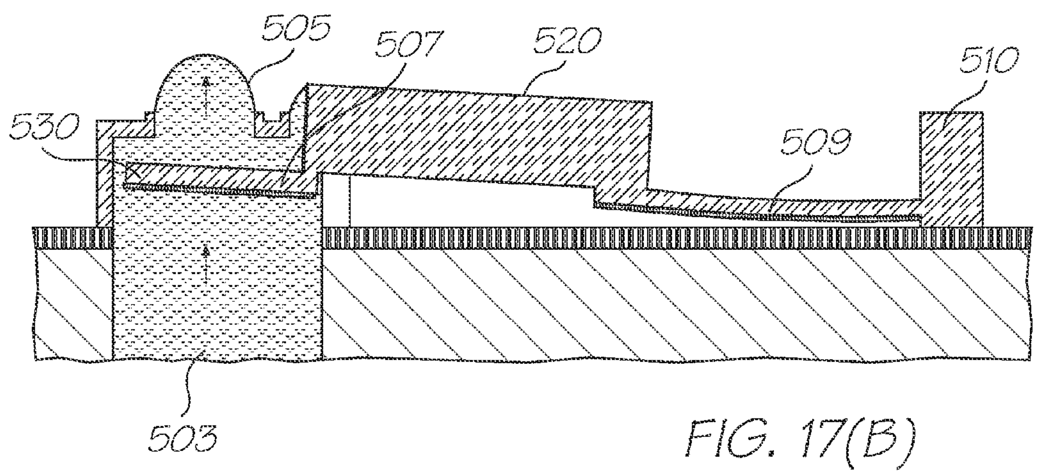
Figure 17C:
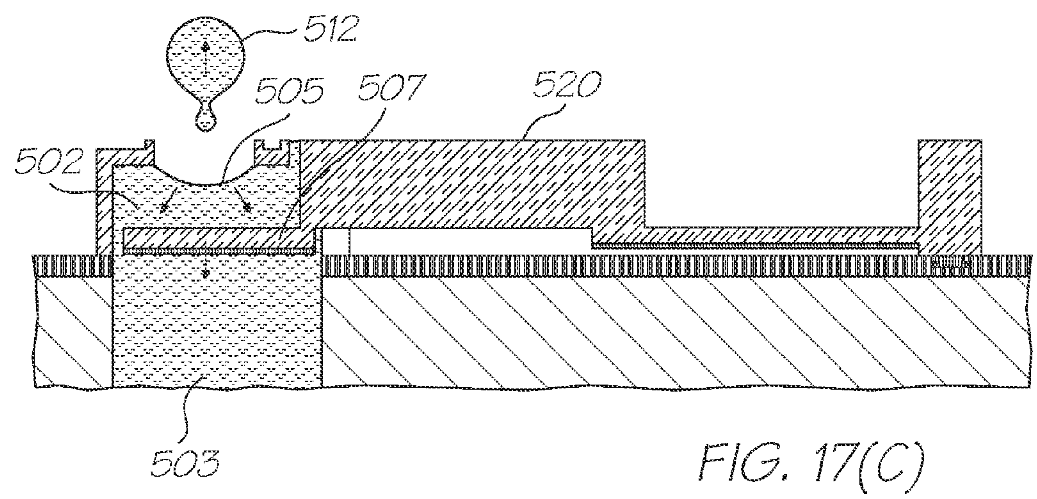

Turning initially to FIGS. 17(*a*)-(*c*), there is provided schematic illustrations of the basic operation of a nozzle arrangement of this embodiment. A nozzle chamber 501 is provided filled with ink 502 by means of an ink inlet channel 503 which can be etched through a wafer substrate on which the nozzle chamber 501 rests. The nozzle chamber 501 further includes an ink ejection port 504 around which an ink meniscus forms.

Inside the nozzle chamber 501 is a paddle type device 507 which is interconnected to an actuator 508 through a slot in the wall of the nozzle chamber 501. The actuator 508 includes a heater means e.g. 509 located adjacent to an end portion of a post 510. The post 510 is fixed to a substrate.

When it is desired to eject a drop from the nozzle chamber 501, as illustrated in FIG. 17(*b*), the heater means 509 is heated so as to undergo thermal expansion. Preferably, the heater means 509 itself or the other portions of the actuator 508 are built from materials having a high bend efficiency where the bend efficiency is defined as:

$$\text{bend efficiency} = \frac{\text{Young's Modulus} \times (\text{Coefficient of thermal Expansion})}{\text{Density} \times \text{Specific Heat Capacity}}$$

A suitable material for the heater elements is a copper nickel alloy which can be formed so as to bend a glass material.

The heater means 509 is ideally located adjacent the end portion of the post 510 such that the effects of activation are magnified at the paddle end 507 such that small thermal expansions near the post 510 result in large movements of the paddle end.

The heater means 509 and consequential paddle movement causes a general increase in pressure around the ink meniscus 505 which expands, as illustrated in FIG. 17(*b*), in a rapid manner. The heater current is pulsed and ink is ejected out of the port 504 in addition to flowing in from the ink channel 503.

Subsequently, the paddle 507 is deactivated to again return to its quiescent position. The deactivation causes a general reflow of the ink into the nozzle chamber. The forward momentum of the ink outside the nozzle rim and the corresponding backflow results in a general necking and breaking off of the drop 512 which proceeds to the print media. The collapsed meniscus 505 results in a general sucking of ink into the nozzle chamber 502 via the ink flow channel 503. In time, the nozzle chamber 501 is refilled such that the position in FIG. 17(*a*) is again reached and the nozzle chamber is subsequently ready for the ejection of another drop of ink.

Figure 18:
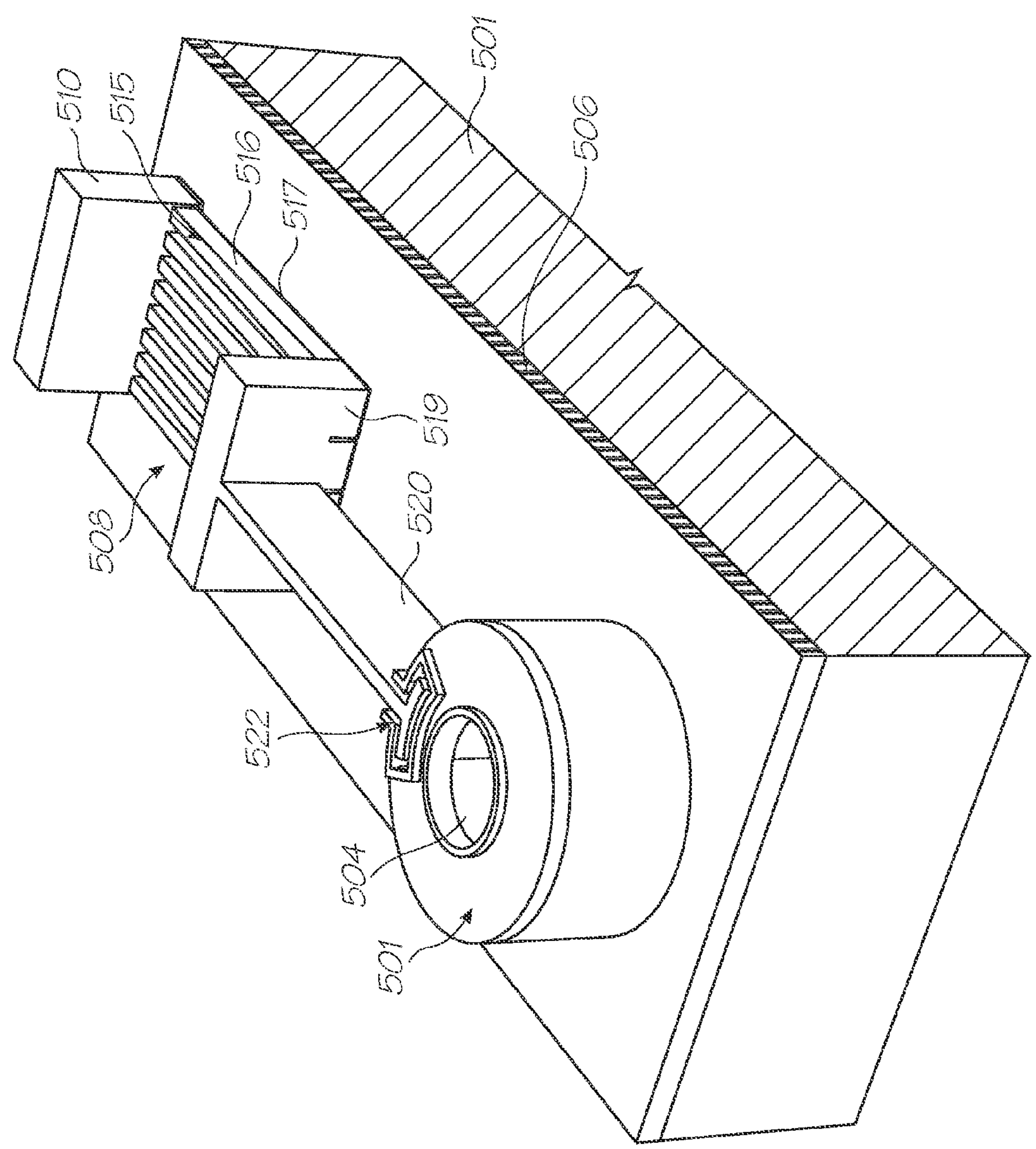
FIG. 18 shows a three dimensional view of a single ink jet nozzle arrangement constructed in accordance with FIG. 17.
Figure 19:
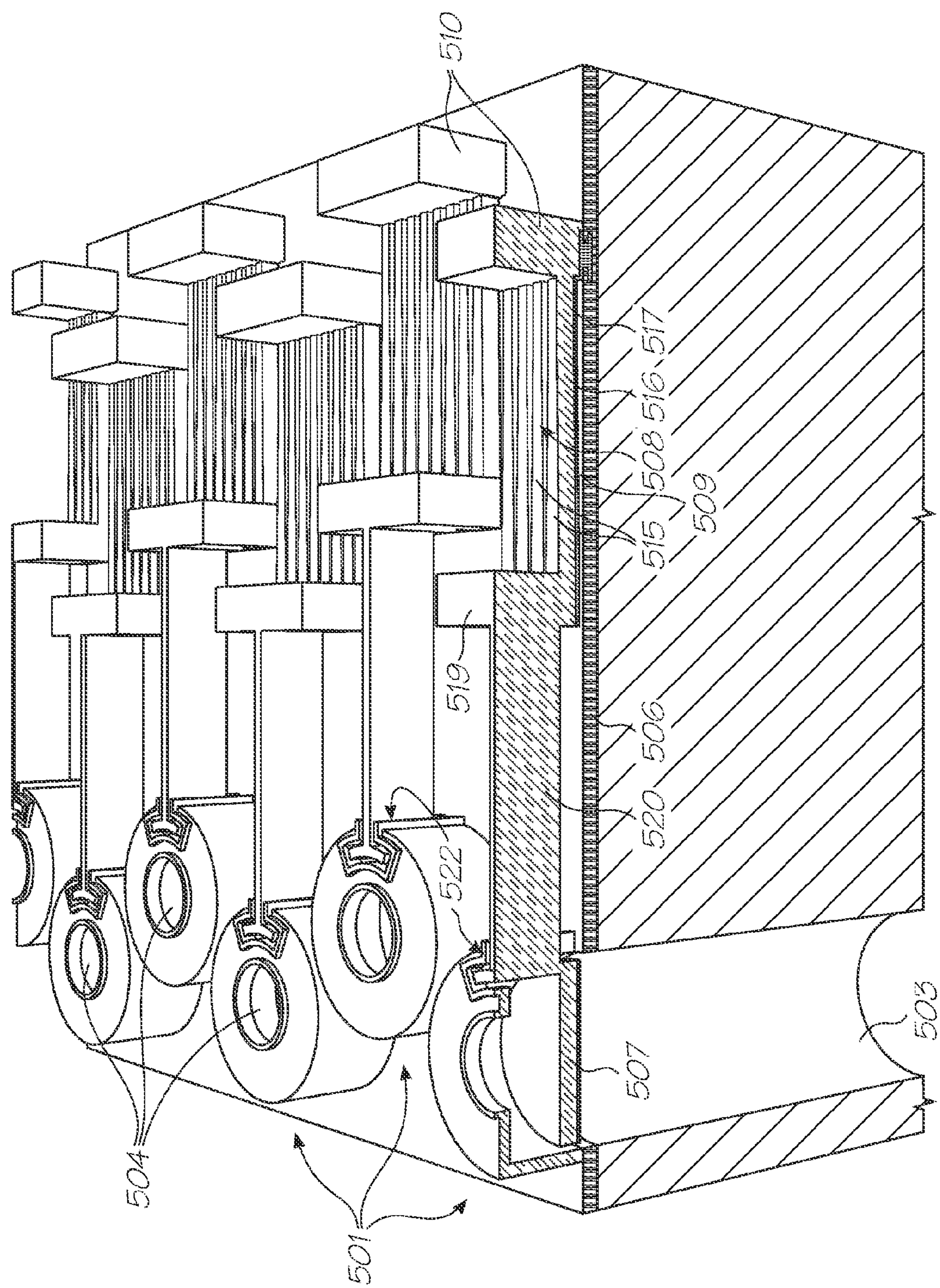
FIG. 19 shows an array of the nozzle arrangements shown in FIG. 18.

FIG. 18 illustrates a side perspective view of the nozzle arrangement. FIG. 19 illustrates sectional view through an array of nozzle arrangement of FIG. 18. In these figures, the numbering of elements previously introduced has been retained.

Firstly, the actuator 508 includes a series of tapered actuator units e.g. 515 which comprise an upper glass portion (amorphous silicon dioxide) 516 formed on top of a titanium nitride layer 517. Alternatively a copper nickel alloy layer (hereinafter called cupronickel) can be utilized which will have a higher bend efficiency.

The titanium nitride layer 517 is in a tapered form and, as such, resistive heating takes place near an end portion of the post 510. Adjacent titanium nitride/glass portions 515 are interconnected at a block portion 519 which also provides a mechanical structural support for the actuator 508.

The heater means 509 ideally includes a plurality of the tapered actuator unit 515 which are elongate and spaced apart such that, upon heating, the bending force exhibited along the axis of the actuator 508 is maximized. Slots are defined between adjacent tapered units 515 and allow for slight differential operation of each actuator 508 with respect to adjacent actuators 508.

The block portion 519 is interconnected to an arm 520. The arm 520 is in turn connected to the paddle 507 inside the nozzle chamber 501 by means of a slot e.g. 522 formed in the side of the nozzle chamber 501. The slot 522 is designed generally to mate with the surfaces of the arm 520 so as to minimize opportunities for the outflow of ink around the arm 520. The ink is held generally within the nozzle chamber 501 via surface tension effects around the slot 522.

When it is desired to actuate the arm 520, a conductive current is passed through the titanium nitride layer 517 via vias within the block portion 519 connecting to a lower CMOS layer 506 which provides the necessary power and control circuitry for the nozzle arrangement. The conductive current results in heating of the nitride layer 517 adjacent to the post 510 which results in a general upward bending of the arm 20 and consequential ejection of ink out of the nozzle 504. The ejected drop is printed on a page in the usual manner for an inkjet printer as previously described.

An array of nozzle arrangements can be formed so as to create a single printhead. For example, in FIG. 24 there is illustrated a partly sectioned various array view which comprises multiple ink ejection nozzle arrangements of FIG. 18 laid out in interleaved lines so as to form a printhead array. Of course, different types of arrays can be formulated including full color arrays etc.

The construction of the printhead system described can proceed utilizing standard MEMS techniques through suitable modification of the steps as set out in U.S. Pat. No. 6,243,113 entitled "Image Creation Method and Apparatus (IJ 41)" to the present applicant, the contents of which are fully incorporated by cross reference.

Substrates

As mentioned above, the dyes of the present invention are especially suitable for use in Hyperlabel™ and netpage systems. Such systems are described in more detail below and in the patent applications listed above, all of which are incorporated herein by reference in their entirety.

Hence, the present invention provides a substrate having an IR-absorbing dye as described above disposed thereon or therein. Preferably, the substrate comprises an interface surface. Preferably, the dye is disposed in the form of coded data suitable for use in netpage and/or Hyperlabel™ systems. For example, the coded data may be indicative of the a plurality of locations and/or an identity of a product item. Preferably, the coded data is disposed over a substantial portion of an interface surface of the substrate (e.g. greater than 20%, greater than 50% or greater than 90% of the surface).

Preferably, the substrate is IR reflective so that the dye disposed thereon may be detected by a sensing device. The substrate may be comprised of any suitable material such as plastics (e.g. polyolefins, polyesters, polyamides etc.), paper, metal or combinations thereof. The substrate may be laminated.

For netpage applications, the substrate is preferably a paper sheet. For Hyperlabel™ applications, the substrate is preferably a tag, a label, a packaging material or a surface of a product item. Typically, tags and labels are comprised of plastics, paper or combinations thereof.

Netpage and Hyperlabel™

There now follows a detailed overview of netpage and Hyperlabel™. (Note: Memjet™ and Hyperlabel™ are trade marks of Silverbrook Research Pty Ltd, Australia). It will be appreciated that not every implementation will necessarily embody all or even most of the specific details and extensions discussed below in relation to the basic system. However, the system is described in its most complete form to reduce the need for external reference when attempting to understand the context in which the preferred embodiments and aspects of the present invention operate.

In brief summary, the preferred form of the netpage system employs a computer interface in the form of a mapped surface, that is, a physical surface which contains references to a map of the surface maintained in a computer system. The map references can be queried by an appropriate sensing device. Depending upon the specific implementation, the map references may be encoded visibly or invisibly, and defined in such a way that a local query on the mapped surface yields an unambiguous map reference both within the map and among different maps. The computer system can contain information about features on the mapped surface, and such information can be retrieved based on map references supplied by a sensing device used with the mapped surface. The information thus retrieved can take the form of actions which are initiated by the computer system on behalf of the operator in response to the operator's interaction with the surface features.

In its preferred form, the netpage system relies on the production of, and human interaction with, netpages. These are pages of text, graphics and images printed on ordinary paper, but which work like interactive web pages. Information is encoded on each page using ink which is substantially invisible to the unaided human eye. The ink, however, and thereby the coded data, can be sensed by an optically imaging pen and transmitted to the netpage system.

In the preferred form, active buttons and hyperlinks on each page can be clicked with the pen to request information from the network or to signal preferences to a network server. In one embodiment, text written by hand on a netpage is automatically recognized and converted to computer text in the netpage system, allowing forms to be filled in. In other embodiments, signatures recorded on a netpage are automatically verified, allowing e-commerce transactions to be securely authorized.

As illustrated in FIG. 1, a printed netpage 1 can represent an interactive form which can be filled in by the user both physically, on the printed page, and "electronically", via communication between the pen and the netpage system. The example shows a "Request" form containing name and address fields and a submit button. The netpage consists of graphic data 2 printed using visible ink, and coded data 3 printed as a collection of tags 4 using invisible ink. The corresponding page description 5, stored on the netpage network, describes the individual elements of the netpage. In particular it describes the type and spatial extent (zone) of each interactive element (i.e. text field or button in the example), to allow the netpage system to correctly interpret input via the netpage. The submit button 6, for example, has a zone 7 which corresponds to the spatial extent of the corresponding graphic 8.

Figure 2:
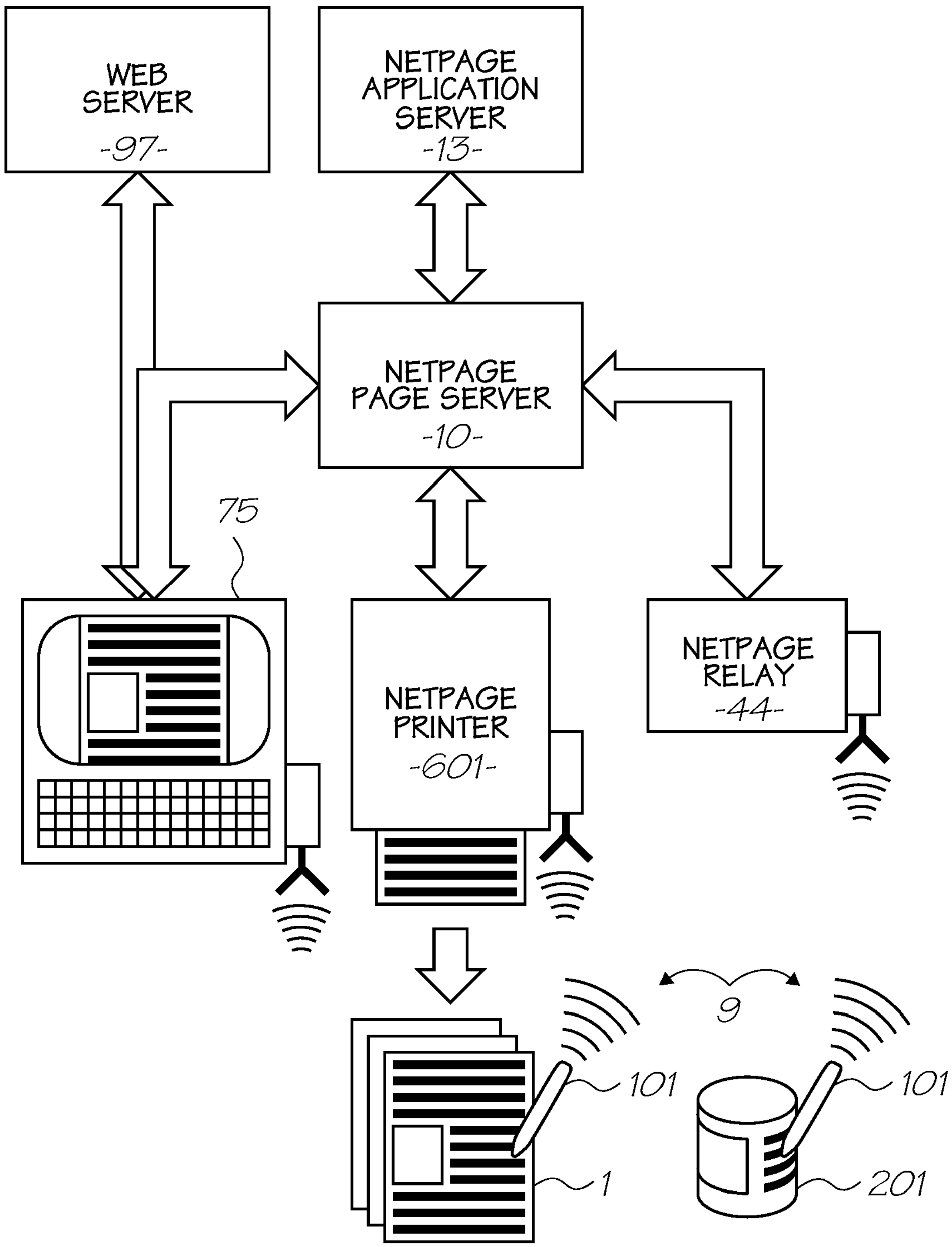
FIG. 2 is a schematic view of a interaction between a netpage pen, a Web terminal, a netpage printer, a netpage relay, a netpage page server, and a netpage application server, and a Web server.
Figure 6:
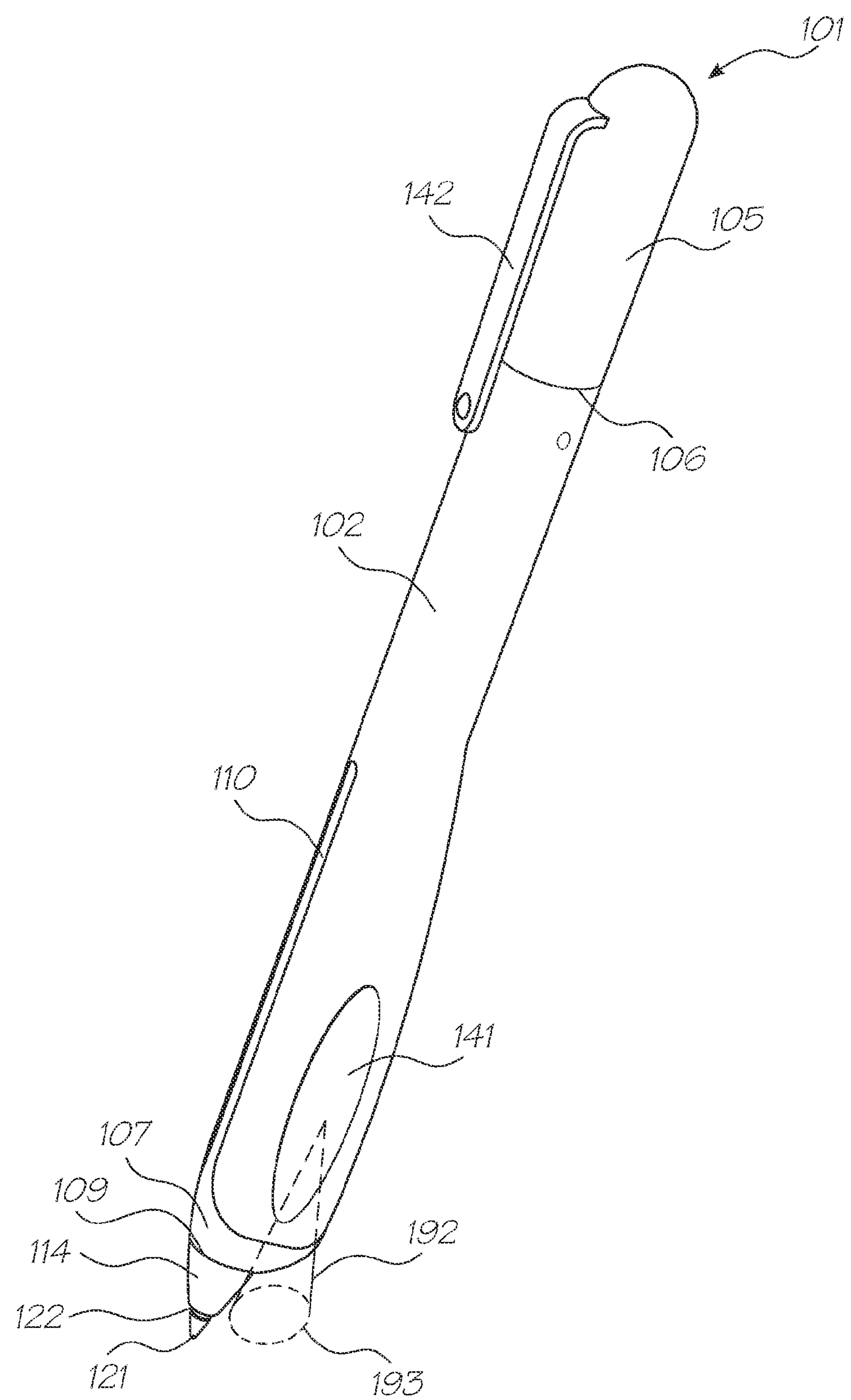
FIG. 6 is a perspective view of a netpage pen and its associated tag-sensing field-of-view cone.
Figure 7:
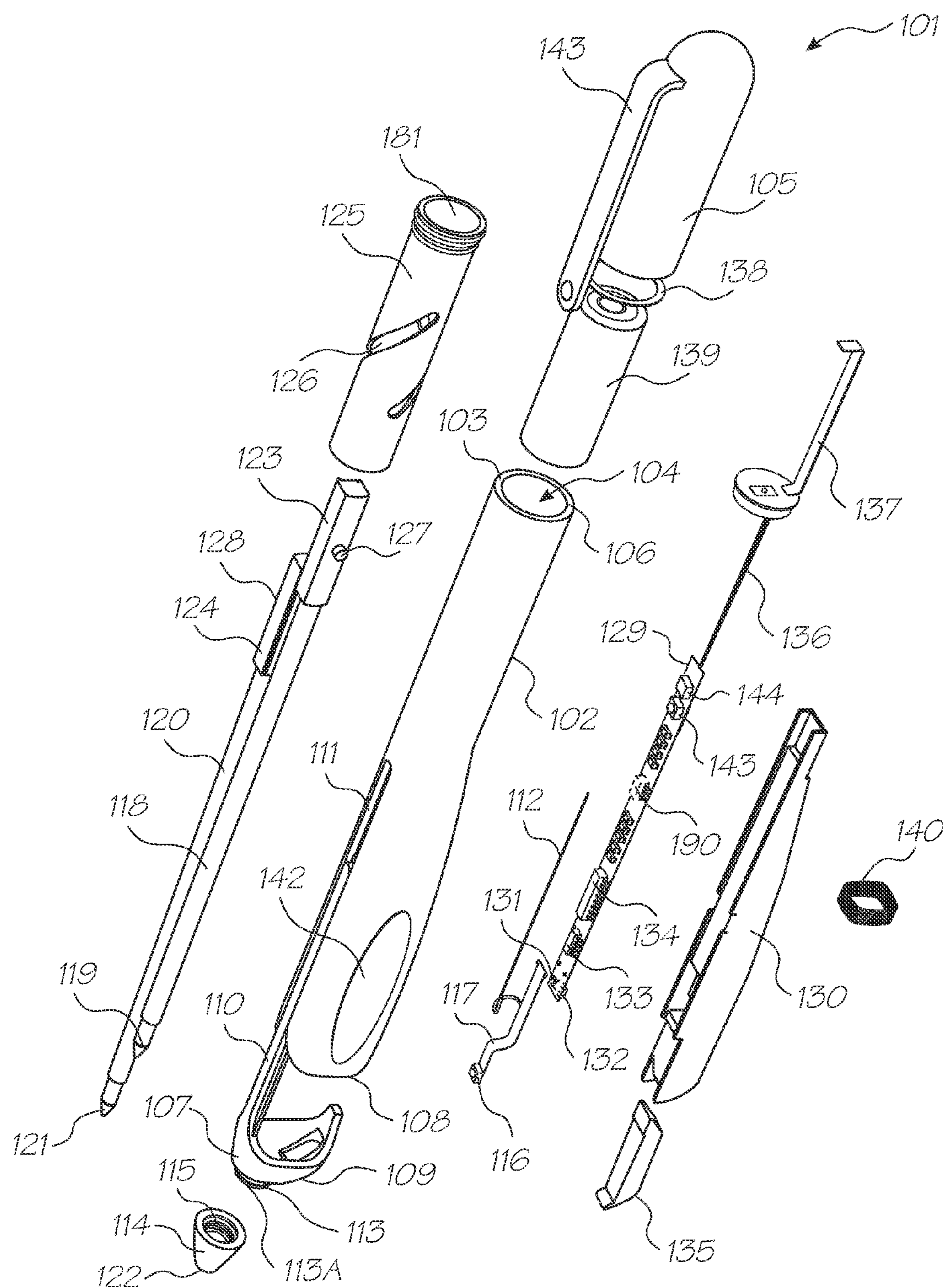
FIG. 7 is a perspective exploded view of the netpage pen shown in FIG. 6.

As illustrated in FIG. 2, the netpage pen 101, a preferred form of which is shown in FIGS. 6 and 7 and described in more detail below, works in conjunction with a personal computer (PC), Web terminal 75, or a netpage printer 601. The netpage printer is an Internet-connected printing appliance for home, office or mobile use. The pen is wireless and communicates securely with the netpage network via a short-range radio link 9. Short-range communication is relayed to the netpage network by a local relay function which is either embedded in the PC, Web terminal or netpage printer, or is provided by a separate relay device 44. The relay function can also be provided by a mobile phone or other device which incorporates both short-range and longer-range communications functions.

In an alternative embodiment, the netpage pen utilises a wired connection, such as a USB or other serial connection, to the PC, Web terminal, netpage printer or relay device.

Figure 9:
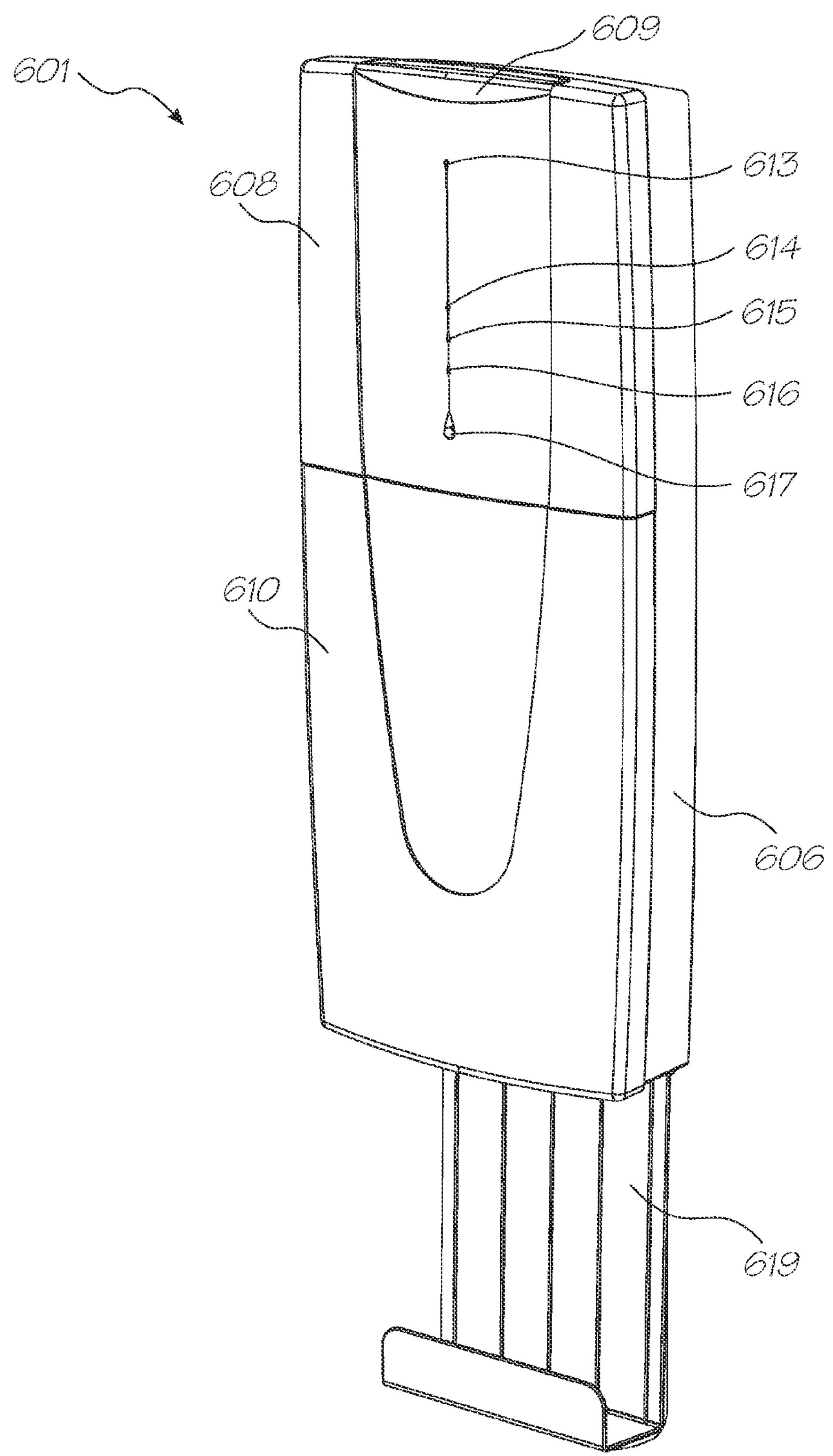
FIG. 9 is a perspective view of a wall-mounted netpage printer.
Figure 10:
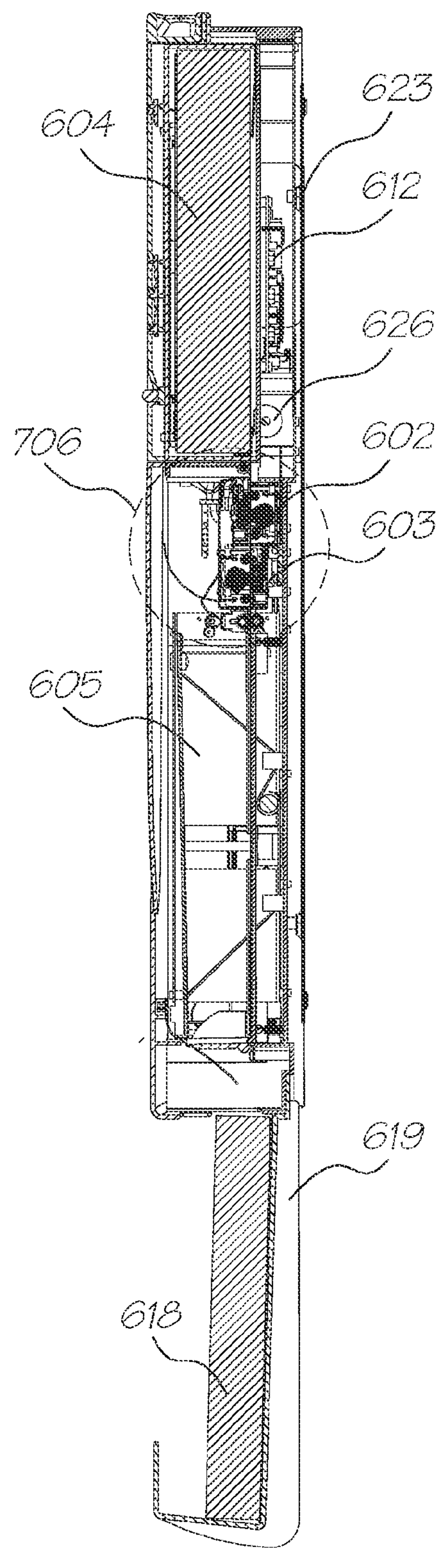
FIG. 10 is a section through the length of the netpage printer of FIG. 9.
Figure 11:
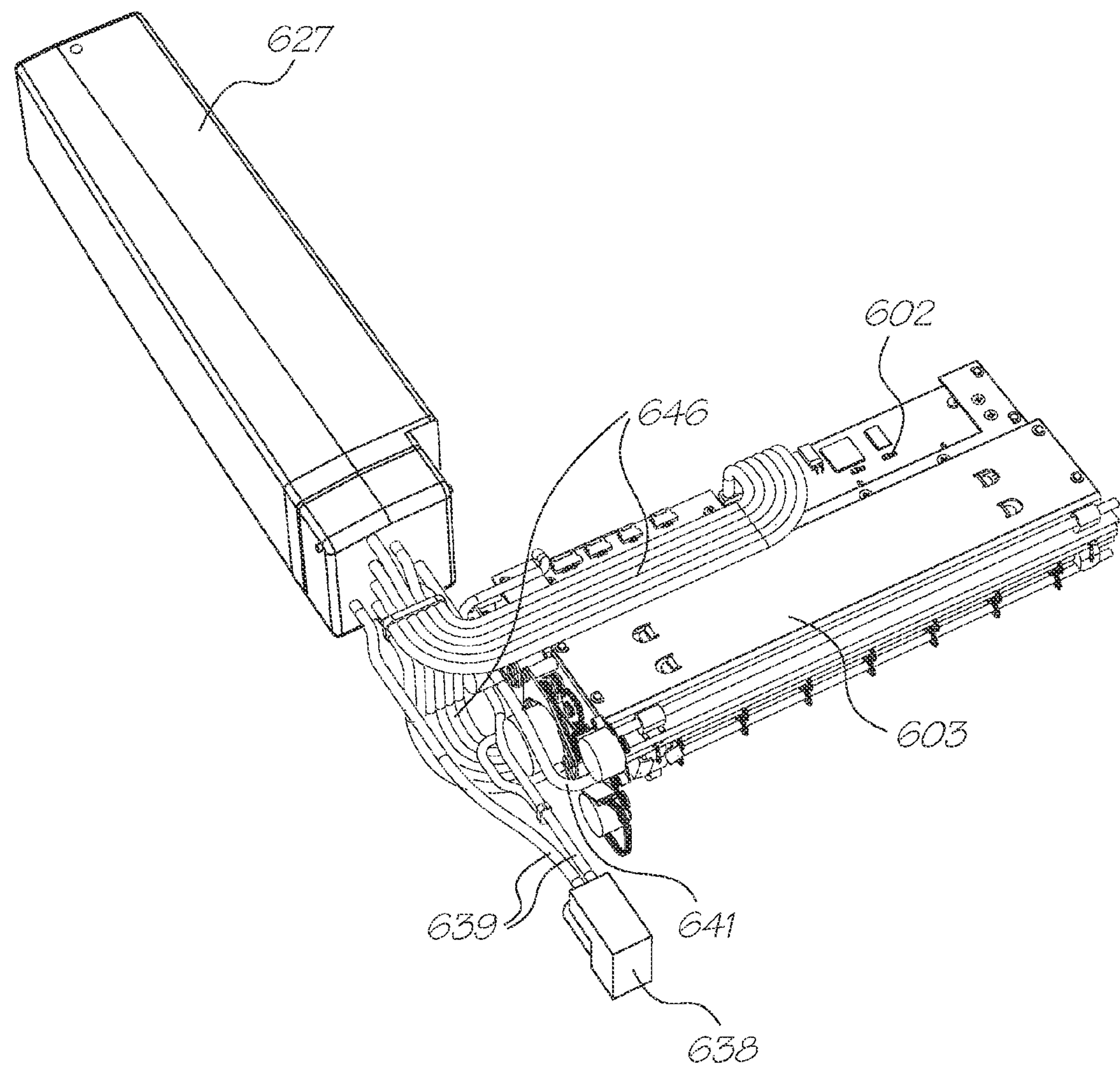
FIG. 11 is a detailed view of the ink cartridge, ink, air and glue paths, and print engines of the netpage printer of FIGS. 9 and 10.

The netpage printer 601, a preferred form of which is shown in FIGS. 9 to 11 and described in more detail below, is able to deliver, periodically or on demand, personalized newspapers, magazines, catalogs, brochures and other publications, all printed at high quality as interactive netpages. Unlike a personal computer, the netpage printer is an appliance which can be, for example, wall-mounted adjacent to an area where the morning news is first consumed, such as in a user's kitchen, near a breakfast table, or near the household's point of departure for the day. It also comes in tabletop, desktop, portable and miniature versions.

Netpages printed at their point of consumption combine the ease-of-use of paper with the timeliness and interactivity of an interactive medium.

As shown in FIG. 2, the netpage pen 101 interacts with the coded data on a printed netpage 1 (or product item 201) and communicates the interaction via a short-range radio link 9 to a relay. The relay sends the interaction to the relevant netpage page server 10 for interpretation. In appropriate circumstances, the page server sends a corresponding message to application computer software running on a netpage application server 13. The application server may in turn send a response which is printed on the originating printer.

In an alternative embodiment, the PC, Web terminal, netpage printer or relay device may communicate directly with local or remote application software, including a local or remote Web server. Relatedly, output is not limited to being printed by the netpage printer. It can also be displayed on the PC or Web terminal, and further interaction can be screen-based rather than paper-based, or a mixture of the two.

The netpage system is made considerably more convenient in the preferred embodiment by being used in conjunction with high-speed microelectromechanical system (MEMS) based inkjet (Memjet™) printers. In the preferred form of this technology, relatively high-speed and high-quality printing is made more affordable to consumers. In its preferred form, a netpage publication has the physical characteristics of a traditional newsmagazine, such as a set of letter-size glossy pages printed in full color on both sides, bound together for easy navigation and comfortable handling.

The netpage printer exploits the growing availability of broadband Internet access. Cable service is available to 95% of households in the United States, and cable modem service offering broadband Internet access is already available to 20% of these. The netpage printer can also operate with slower connections, but with longer delivery times and lower image quality. Indeed, the netpage system can be enabled using existing consumer inkjet and laser printers, although the system will operate more slowly and will therefore be less acceptable from a consumer's point of view. In other embodiments, the netpage system is hosted on a private intranet. In still other embodiments, the netpage system is hosted on a single computer or computer-enabled device, such as a printer.

Netpage publication servers 14 on the netpage network are configured to deliver print-quality publications to netpage printers. Periodical publications are delivered automatically to subscribing netpage printers via pointcasting and multicasting Internet protocols. Personalized publications are filtered and formatted according to individual user profiles.

A netpage printer can be configured to support any number of pens, and a pen can work with any number of netpage printers. In the preferred implementation, each netpage pen has a unique identifier. A household may have a collection of colored netpage pens, one assigned to each member of the family. This allows each user to maintain a distinct profile with respect to a netpage publication server or application server.

A netpage pen can also be registered with a netpage registration server 11 and linked to one or more payment card accounts. This allows e-commerce payments to be securely authorized using the netpage pen. The netpage registration server compares the signature captured by the netpage pen with a previously registered signature, allowing it to authenticate the user's identity to an e-commerce server. Other biometrics can also be used to verify identity. A version of the netpage pen includes fingerprint scanning, verified in a similar way by the netpage registration server.

Although a netpage printer may deliver periodicals such as the morning newspaper without user intervention, it can be configured never to deliver unsolicited junk mail. In its preferred form, it only delivers periodicals from subscribed or otherwise authorized sources. In this respect, the netpage printer is unlike a fax machine or e-mail account which is visible to any junk mailer who knows the telephone number or email address.

1 Netpage System Architecture

Each object model in the system is described using a Unified Modeling Language (UML) class diagram. A class diagram consists of a set of object classes connected by relationships, and two kinds of relationships are of interest here: associations and generalizations. An association represents some kind of relationship between objects, i.e. between instances of classes. A generalization relates actual classes, and can be understood in the following way: if a class is thought of as the set of all objects of that class, and class A is a generalization of class B, then B is simply a subset of A. The UML does not directly support second-order modelling—i.e. classes of classes.

Each class is drawn as a rectangle labelled with the name of the class. It contains a list of the attributes of the class, separated from the name by a horizontal line, and a list of the operations of the class, separated from the attribute list by a horizontal line. In the class diagrams which follow, however, operations are never modelled.

An association is drawn as a line joining two classes, optionally labelled at either end with the multiplicity of the association. The default multiplicity is one. An asterisk (*) indicates a multiplicity of "many", i.e. zero or more. Each association is optionally labelled with its name, and is also optionally labelled at either end with the role of the corresponding class. An open diamond indicates an aggregation association ("is-part-of"), and is drawn at the aggregator end of the association line.

A generalization relationship ("is-a") is drawn as a solid line joining two classes, with an arrow (in the form of an open triangle) at the generalization end.

When a class diagram is broken up into multiple diagrams, any class which is duplicated is shown with a dashed outline in all but the main diagram which defines it. It is shown with attributes only where it is defined.

1.1 Netpages

Netpages are the foundation on which a netpage network is built. They provide a paper-based user interface to published information and interactive services.

A netpage consists of a printed page (or other surface region) invisibly tagged with references to an online description of the page. The online page description is maintained persistently by a netpage page server. The page description describes the visible layout and content of the page, including text, graphics and images. It also describes the input elements on the page, including buttons, hyperlinks, and input fields. A netpage allows markings made with a netpage pen on its surface to be simultaneously captured and processed by the netpage system.

Multiple netpages can share the same page description. However, to allow input through otherwise identical pages to be distinguished, each netpage is assigned a unique page identifier. This page ID has sufficient precision to distinguish between a very large number of netpages.

Each reference to the page description is encoded in a printed tag. The tag identifies the unique page on which it appears, and thereby indirectly identifies the page description. The tag also identifies its own position on the page. Characteristics of the tags are described in more detail below.

Tags are printed in infrared-absorptive ink on any substrate which is infrared-reflective, such as ordinary paper. Near-infrared wavelengths are invisible to the human eye but are easily sensed by a solid-state image sensor with an appropriate filter.

A tag is sensed by an area image sensor in the netpage pen, and the tag data is transmitted to the netpage system via the nearest netpage printer. The pen is wireless and communicates with the netpage printer via a short-range radio link. Tags are sufficiently small and densely arranged that the pen can reliably image at least one tag even on a single click on the page. It is important that the pen recognize the page ID and position on every interaction with the page, since the interaction is stateless. Tags are error-correctably encoded to make them partially tolerant to surface damage.

The netpage page server maintains a unique page instance for each printed netpage, allowing it to maintain a distinct set of user-supplied values for input fields in the page description for each printed netpage.

Figure 4:
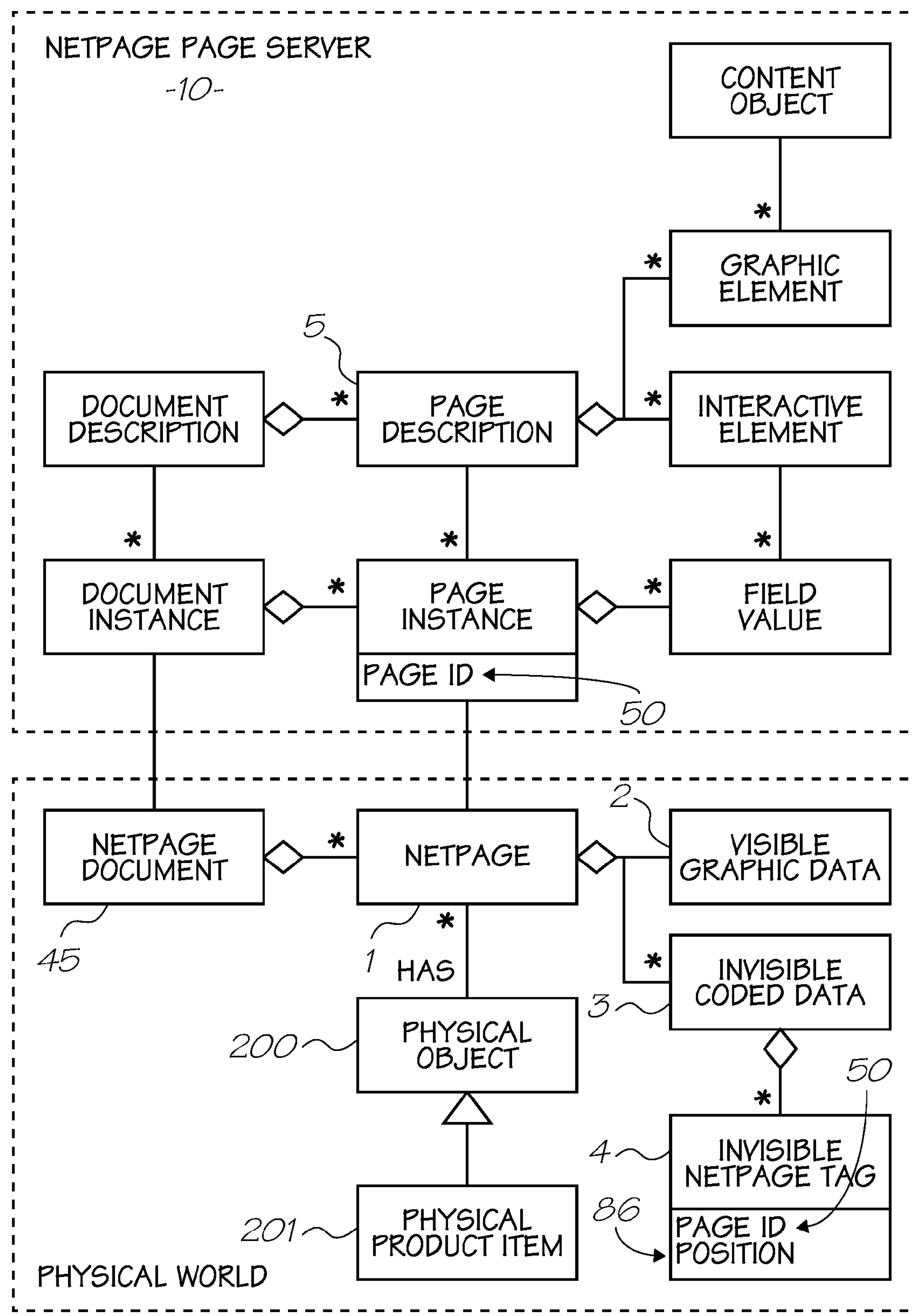
FIG. 4 is a schematic view of a high-level structure of a printed netpage and its online page description.

The relationship between the page description, the page instance, and the printed netpage is shown in FIG. 4. The printed netpage may be part of a printed netpage document 45. The page instance is associated with both the netpage printer which printed it and, if known, the netpage user who requested it.

As shown in FIG. 4, one or more netpages may also be associated with a physical object such as a product item, for example when printed onto the product item's label, packaging, or actual surface.

1.2 Netpage Tags

1.2.1 Tag Data Content

In a preferred form, each tag identifies the region in which it appears, and the location of that tag within the region. A tag may also contain flags which relate to the region as a whole or to the tag. One or more flag bits may, for example, signal a tag sensing device to provide feedback indicative of a function associated with the immediate area of the tag, without the sensing device having to refer to a description of the region. A netpage pen may, for example, illuminate an "active area" LED when in the zone of a hyperlink.

As will be more clearly explained below, in a preferred embodiment, each tag contains an easily recognized invariant structure which aids initial detection, and which assists in minimizing the effect of any warp induced by the surface or by the sensing process. The tags preferably tile the entire page, and are sufficiently small and densely arranged that the pen can reliably image at least one tag even on a single click on the page. It is important that the pen recognize the page ID and position on every interaction with the page, since the interaction is stateless.

In a preferred embodiment, the region to which a tag refers coincides with an entire page, and the region ID encoded in the tag is therefore synonymous with the page ID of the page on which the tag appears. In other embodiments, the region to which a tag refers can be an arbitrary subregion of a page or other surface. For example, it can coincide with the zone of an interactive element, in which case the region ID can directly identify the interactive element.

In the preferred form, each tag contains 120 bits of information. The region ID is typically allocated up to 100 bits, the tag ID at least 16 bits, and the remaining bits are allocated to flags etc. Assuming a tag density of 64 per square inch, a 16-bit tag ID supports a region size of up to 1024 square inches. Larger regions can be mapped continuously without increasing the tag ID precision simply by using abutting regions and maps. The 100-bit region ID allows $2^{100}$ (~$10^{30}$ or a million trillion trillion) different regions to be uniquely identified.

1.2.2 Tag Data Encoding

In one embodiment, the 120 bits of tag data are redundantly encoded using a (15, 5) Reed-Solomon code. This yields 360 encoded bits consisting of 6 codewords of 154-bit symbols each. The (15, 5) code allows up to 5 symbol errors to be corrected per codeword, i.e. it is tolerant of a symbol error rate of up to 33% per codeword.

Each 4-bit symbol is represented in a spatially coherent way in the tag, and the symbols of the six codewords are interleaved spatially within the tag. This ensures that a burst error (an error affecting multiple spatially adjacent bits) damages a minimum number of symbols overall and a minimum number of symbols in any one codeword, thus maximising the likelihood that the burst error can be fully corrected.

Any suitable error-correcting code code can be used in place of a (15, 5) Reed-Solomon code, for example: a Reed-Solomon code with more or less redundancy, with the same or different symbol and codeword sizes; another block code; or a different kind of code, such as a convolutional code (see, for example, Stephen B. Wicker, Error Control Systems for Digital Communication and Storage, Prentice-Hall 1995, the contents of which a herein incorporated by reference thereto).

In order to support "single-click" interaction with a tagged region via a sensing device, the sensing device must be able to see at least one entire tag in its field of view no matter where in the region or at what orientation it is positioned. The required diameter of the field of view of the sensing device is therefore a function of the size and spacing of the tags.

1.2.3 Tag Structure

Figure 5A:
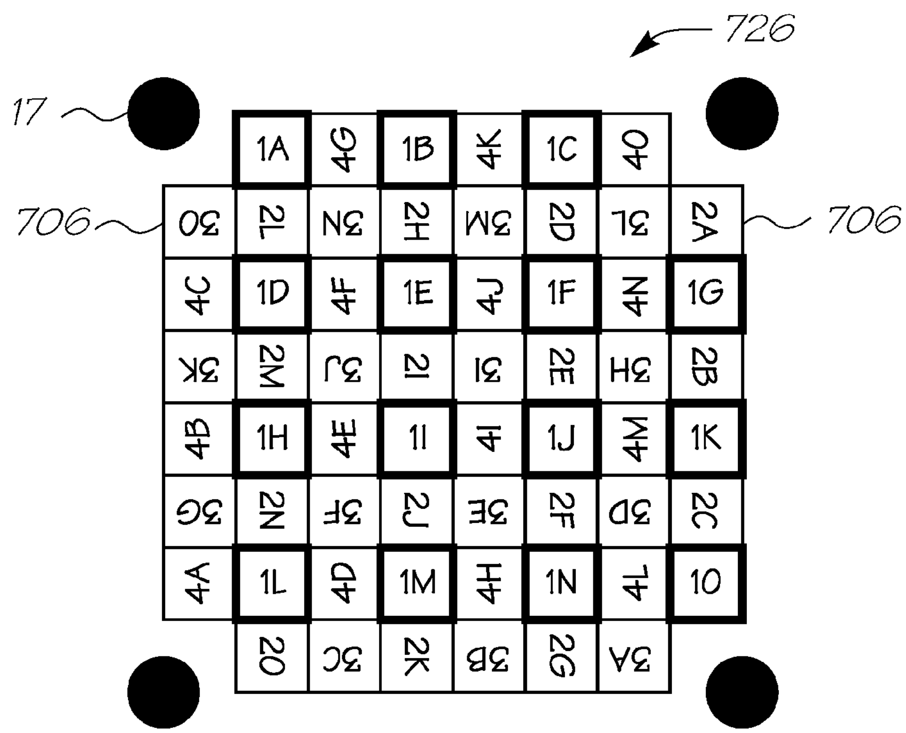
FIG. 5A is a plan view showing the interleaving and rotation of the symbols of four codewords of the tag.
Figure 5B:
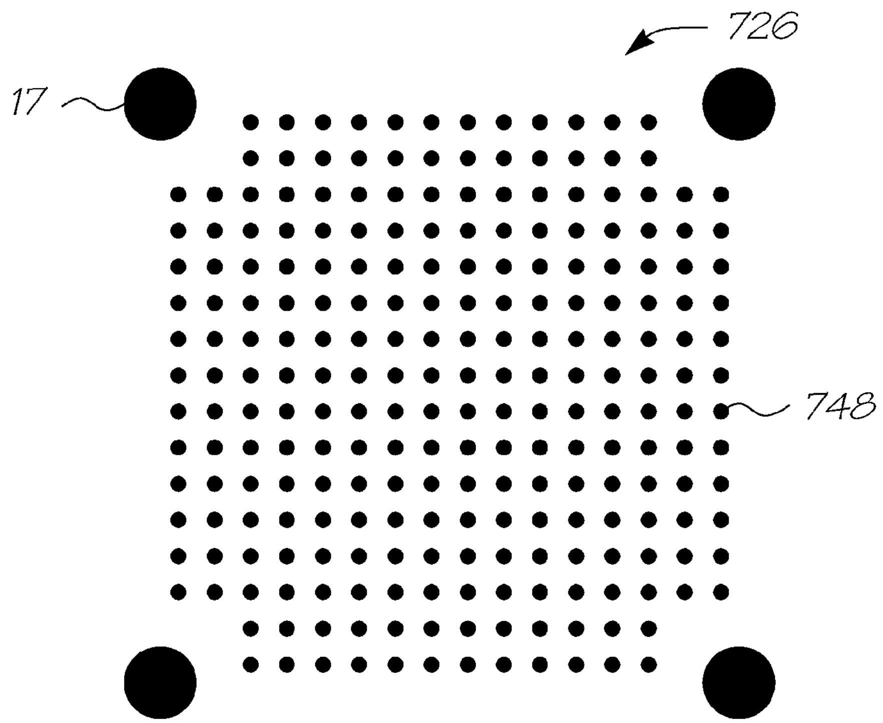
FIG. 5B is a plan view showing a macrodot layout for the tag shown in FIG. 5*a;*
Figure 5C:
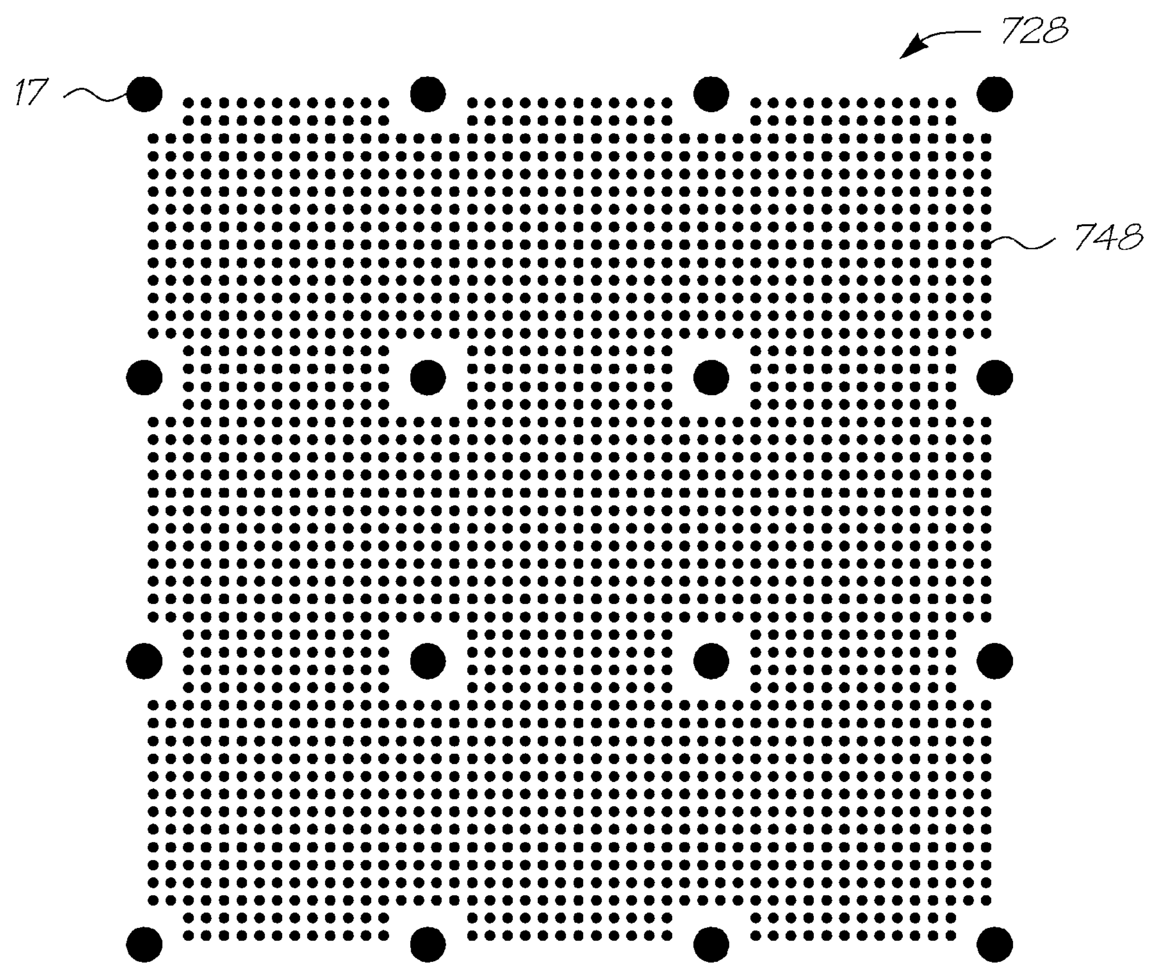
FIG. 5C is a plan view showing an arrangement of nine of the tags shown in FIGS. 5*a* and 5*b*, in which targets are shared between adjacent tags.
Figure 5D:
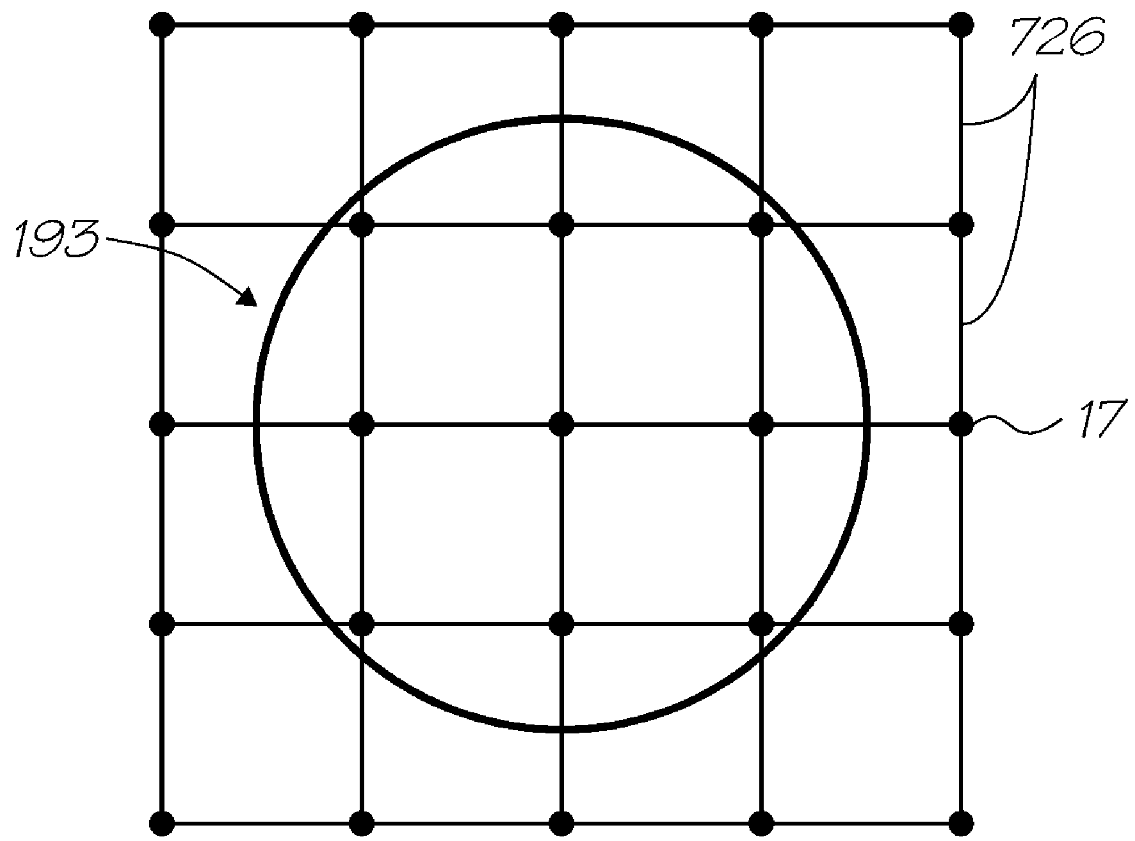
FIG. 5D is a plan view showing a relationship between a set of the tags shown in FIG. 5*a* and a field of view of a netpage sensing device in the form of a netpage pen.

FIG. 5*a* shows a tag 4, in the form of tag 726 with four perspective targets 17. The tag 726 represents sixty 4-bit Reed-Solomon symbols 747, for a total of 240 bits. The tag represents each "one" bit by the presence of a mark 748, referred to as a macrodot, and each "zero" bit by the absence of the corresponding macrodot. FIG. 5*c* shows a square tiling 728 of nine tags, containing all "one" bits for illustrative purposes. It will be noted that the perspective targets are designed to be shared between adjacent tags. FIG. 5*d* shows a square tiling of 16 tags and a corresponding minimum field of view 193, which spans the diagonals of two tags.

Using a (15, 7) Reed-Solomon code, 112 bits of tag data are redundantly encoded to produce 240 encoded bits. The four codewords are interleaved spatially within the tag to maximize resilience to burst errors. Assuming a 16-bit tag ID as before, this allows a region ID of up to 92 bits.

The data-bearing macrodots 748 of the tag are designed to not overlap their neighbors, so that groups of tags cannot produce structures that resemble targets. This also saves ink. The perspective targets allow detection of the tag, so further targets are not required.

Although the tag may contain an orientation feature to allow disambiguation of the four possible orientations of the tag relative to the sensor, the present invention is concerned with embedding orientation data in the tag data. For example, the four codewords can be arranged so that each tag orientation (in a rotational sense) contains one codeword placed at that orientation, as shown in FIG. 5*a*, where each symbol is labelled with the number of its codeword (1-4) and the position of the symbol within the codeword (A-O). Tag decoding then consists of decoding one codeword at each rotational orientation. Each codeword can either contain a single bit indicating whether it is the first codeword, or two bits indicating which codeword it is. The latter approach has the advantage that if, say, the data content of only one codeword is required, then at most two codewords need to be decoded to obtain the desired data. This may be the case if the region ID is not expected to change within a stroke and is thus only decoded at the start of a stroke. Within a stroke only the codeword containing the tag ID is then desired. Furthermore, since the rotation of the sensing device changes slowly and predictably within a stroke, only one codeword typically needs to be decoded per frame.

It is possible to dispense with perspective targets altogether and instead rely on the data representation being self-registering. In this case each bit value (or multi-bit value) is typically represented by an explicit glyph, i.e. no bit value is represented by the absence of a glyph. This ensures that the data grid is well-populated, and thus allows the grid to be reliably identified and its perspective distortion detected and subsequently corrected during data sampling. To allow tag boundaries to be detected, each tag data must contain a marker pattern, and these must be redundantly encoded to allow reliable detection. The overhead of such marker patterns is similar to the overhead of explicit perspective targets. Various such schemes are described in the present applicants' co-pending PCT application PCT/AU01/01274 filed 11 Oct. 2001.

The arrangement 728 of FIG. 5*c* shows that the square tag 726 can be used to fully tile or tesselate, i.e. without gaps or overlap, a plane of arbitrary size.

Although in preferred embodiments the tagging schemes described herein encode a single data bit using the presence or absence of a single undifferentiated macrodot, they can also use sets of differentiated glyphs to represent single-bit or multi-bit values, such as the sets of glyphs illustrated in the present applicants' co-pending PCT application PCT/AU01/01274 filed 11 Oct. 2001.

1.3 The Netpage Network

Figure 3:
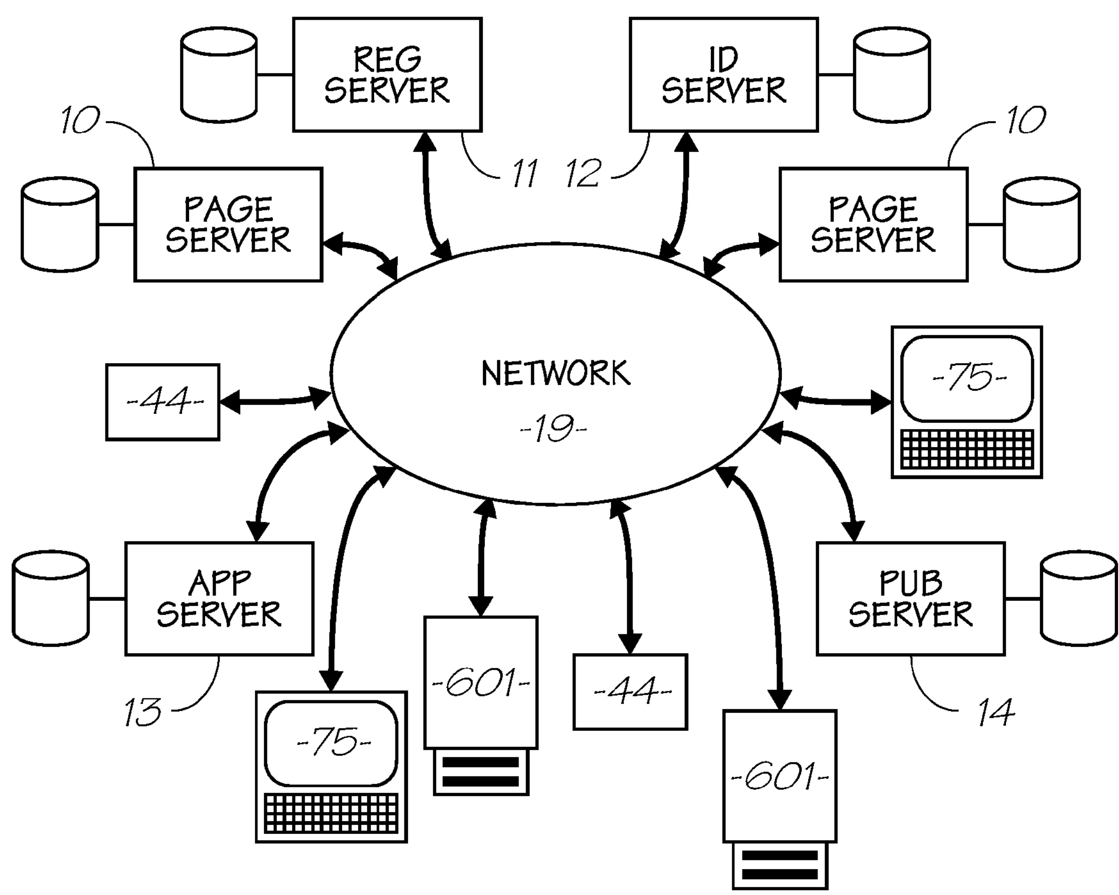
FIG. 3 illustrates a collection of netpage servers, Web terminals, printers and relays interconnected via a network.

In a preferred embodiment, a netpage network consists of a distributed set of netpage page servers 10, netpage registration servers 11, netpage ID servers 12, netpage application servers 13, netpage publication servers 14, Web terminals 75, netpage printers 601, and relay devices 44 connected via a network 19 such as the Internet, as shown in FIG. 3.

The netpage registration server 11 is a server which records relationships between users, pens, printers, applications and publications, and thereby authorizes various network activities. It authenticates users and acts as a signing proxy on behalf of authenticated users in application transactions. It also provides handwriting recognition services. As described above, a netpage page server 10 maintains persistent information about page descriptions and page instances. The netpage network includes any number of page servers, each handling a subset of page instances. Since a page server also maintains user input values for each page instance, clients such as netpage printers send netpage input directly to the appropriate page server. The page server interprets any such input relative to the description of the corresponding page.

A netpage ID server 12 allocates document IDs 51 on demand, and provides load-balancing of page servers via its ID allocation scheme.

A netpage printer uses the Internet Distributed Name System (DNS), or similar, to resolve a netpage page ID 50 into the network address of the netpage page server handling the corresponding page instance.

A netpage application server 13 is a server which hosts interactive netpage applications. A netpage publication server 14 is an application server which publishes netpage documents to netpage printers.

Netpage servers can be hosted on a variety of network server platforms from man-ufacturers such as IBM, Hewlett-Packard, and Sun. Multiple netpage servers can run concurrently on a single host, and a single server can be distributed over a number of hosts. Some or all of the functionality provided by netpage servers, and in particular the functionality provided by the ID server and the page server, can also be provided directly in a netpage appliance such as a netpage printer, in a computer workstation, or on a local network.

1.4 The Netpage Printer

The netpage printer 601 is an appliance which is registered with the netpage system and prints netpage documents on demand and via subscription. Each printer has a unique printer ID 62, and is connected to the netpage network via a network such as the Internet, ideally via a broadband connection.

Apart from identity and security settings in non-volatile memory, the netpage printer contains no persistent storage. As far as a user is concerned, "the network is the computer". Netpages function interactively across space and time with the help of the distributed netpage page servers 10, independently of particular netpage printers.

The netpage printer receives subscribed netpage documents from netpage publication servers 14. Each document is distributed in two parts: the page layouts, and the actual text and image objects which populate the pages. Because of personalization, page layouts are typically specific to a particular subscriber and so are pointcast to the subscriber's printer via the appropriate page server. Text and image objects, on the other hand, are typically shared with other subscribers, and so are multicast to all subscribers' printers and the appropriate page servers.

The netpage publication server optimizes the segmentation of document content into pointcasts and multicasts. After receiving the pointcast of a document's page layouts, the printer knows which multicasts, if any, to listen to.

Once the printer has received the complete page layouts and objects that define the document to be printed, it can print the document.

The printer rasterizes and prints odd and even pages simultaneously on both sides of the sheet. It contains duplexed print engine controllers 760 and print engines utilizing Memjet™ printheads 350 for this purpose.

The printing process consists of two decoupled stages: rasterization of page descriptions, and expansion and printing of page images. The raster image processor (RIP) consists of one or more standard DSPs 757 running in parallel. The duplexed print engine controllers consist of custom processors which expand, dither and print page images in real time, synchronized with the operation of the printheads in the print engines.

Printers not enabled for IR printing have the option to print tags using IR-absorptive black ink, although this restricts tags to otherwise empty areas of the page. Although such pages have more limited functionality than IR-printed pages, they are still classed as netpages.

A normal netpage printer prints netpages on sheets of paper. More specialised netpage printers may print onto more specialised surfaces, such as globes. Each printer supports at least one surface type, and supports at least one tag tiling scheme, and hence tag map, for each surface type. The tag map 811 which describes the tag tiling scheme actually used to print a document becomes associated with that document so that the document's tags can be correctly interpreted.

FIG. 2 shows the netpage printer class diagram, reflecting printer-related information maintained by a registration server 11 on the netpage network.

1.5 The Netpage Pen

The active sensing device of the netpage system is typically a pen 101, which, using its embedded controller 134, is able to capture and decode IR position tags from a page via an image sensor. The image sensor is a solid-state device provided with an appropriate filter to permit sensing at only near-infrared wavelengths. As described in more detail below, the system is able to sense when the nib is in contact with the surface, and the pen is able to sense tags at a sufficient rate to capture human handwriting (i.e. at 200 dpi or greater and 100 Hz or faster). Information captured by the pen is encrypted and wirelessly transmitted to the printer (or base station), the printer or base station interpreting the data with respect to the (known) page structure.

Figure 14:
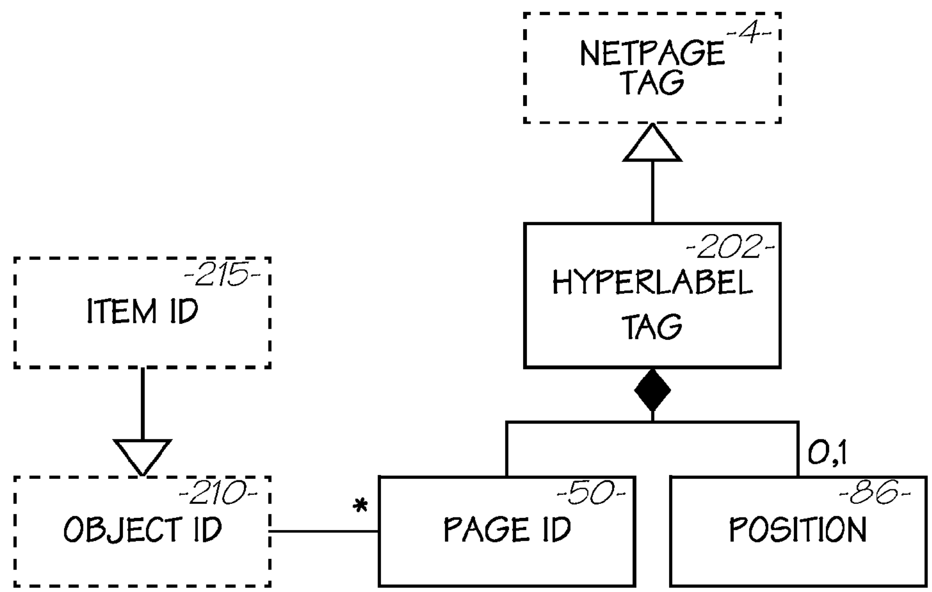
FIG. 14 is a schematic view of the structure of a Hyperlabel tag.
Figure 15:
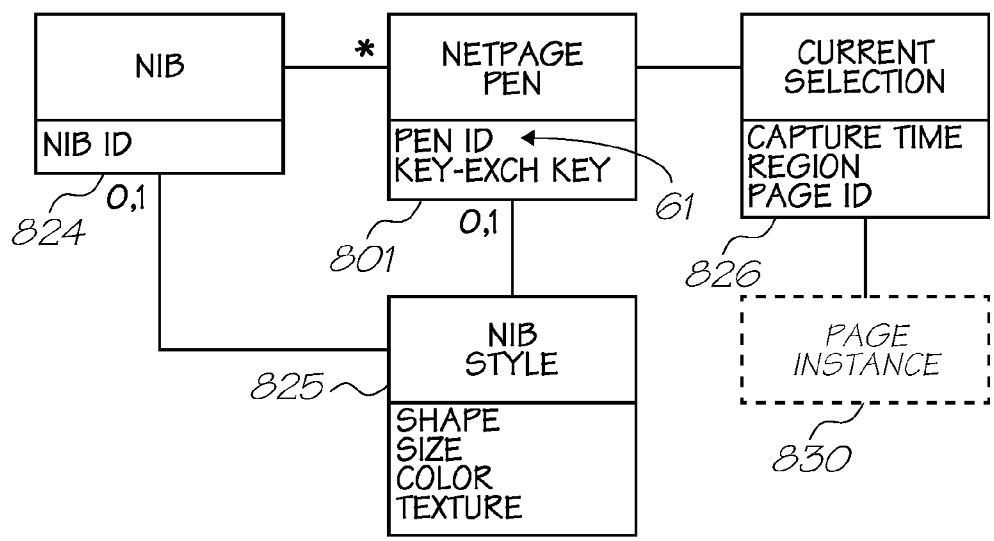
FIG. 15 is a schematic view of a pen class diagram.

The preferred embodiment of the netpage pen operates both as a normal marking ink pen and as a non-marking stylus. The marking aspect, however, is not necessary for using the netpage system as a browsing system, such as when it is used as an Internet interface. Each netpage pen is registered with the netpage system and has a unique pen ID 61. FIG. 14 shows the netpage pen class diagram, reflecting pen-related information maintained by a registration server 11 on the netpage network.

When either nib is in contact with a netpage, the pen determines its position and orientation relative to the page. The nib is attached to a force sensor, and the force on the nib is interpreted relative to a threshold to indicate whether the pen is "up" or "down". This allows a interactive element on the page to be 'clicked' by pressing with the pen nib, in order to request, say, information from a network. Furthermore, the force is captured as a continuous value to allow, say, the full dynamics of a signature to be verified.

The pen determines the position and orientation of its nib on the netpage by imaging, in the infrared spectrum, an area 193 of the page in the vicinity of the nib. It decodes the nearest tag and computes the position of the nib relative to the tag from the observed perspective distortion on the imaged tag and the known geometry of the pen optics. Although the position resolution of the tag may be low, because the tag density on the page is inversely proportional to the tag size, the adjusted position resolution is quite high, exceeding the minimum resolution required for accurate handwriting recognition.

Pen actions relative to a netpage are captured as a series of strokes. A stroke consists of a sequence of time-stamped pen positions on the page, initiated by a pen-down event and completed by the subsequent pen-up event. A stroke is also tagged with the page ID 50 of the netpage whenever the page ID changes, which, under normal circumstances, is at the commencement of the stroke.

Each netpage pen has a current selection 826 associated with it, allowing the user to perform copy and paste operations etc. The selection is timestamped to allow the system to discard it after a defined time period. The current selection describes a region of a page instance. It consists of the most recent digital ink stroke captured through the pen relative to the background area of the page. It is interpreted in an application-specific manner once it is submitted to an application via a selection hyperlink activation.

Each pen has a current nib 824. This is the nib last notified by the pen to the system. In the case of the default netpage pen described above, either the marking black ink nib or the non-marking stylus nib is current. Each pen also has a current nib style 825. This is the nib style last associated with the pen by an application, e.g. in response to the user selecting a color from a palette. The default nib style is the nib style associated with the current nib. Strokes captured through a pen are tagged with the current nib style. When the strokes are subsequently reproduced, they are reproduced in the nib style with which they are tagged.

Whenever the pen is within range of a printer with which it can communicate, the pen slowly flashes its "online" LED. When the pen fails to decode a stroke relative to the page, it momentarily activates its "error" LED. When the pen succeeds in decoding a stroke relative to the page, it momentarily activates its "ok" LED.

A sequence of captured strokes is referred to as digital ink. Digital ink forms the basis for the digital exchange of drawings and handwriting, for online recognition of handwriting, and for online verification of signatures.

The pen is wireless and transmits digital ink to the netpage printer via a short-range radio link. The transmitted digital ink is encrypted for privacy and security and packetized for efficient transmission, but is always flushed on a pen-up event to ensure timely handling in the printer.

When the pen is out-of-range of a printer it buffers digital ink in internal memory, which has a capacity of over ten minutes of continuous handwriting. When the pen is once again within range of a printer, it transfers any buffered digital ink.

A pen can be registered with any number of printers, but because all state data resides in netpages both on paper and on the network, it is largely immaterial which printer a pen is communicating with at any particular time.

Figure 8:
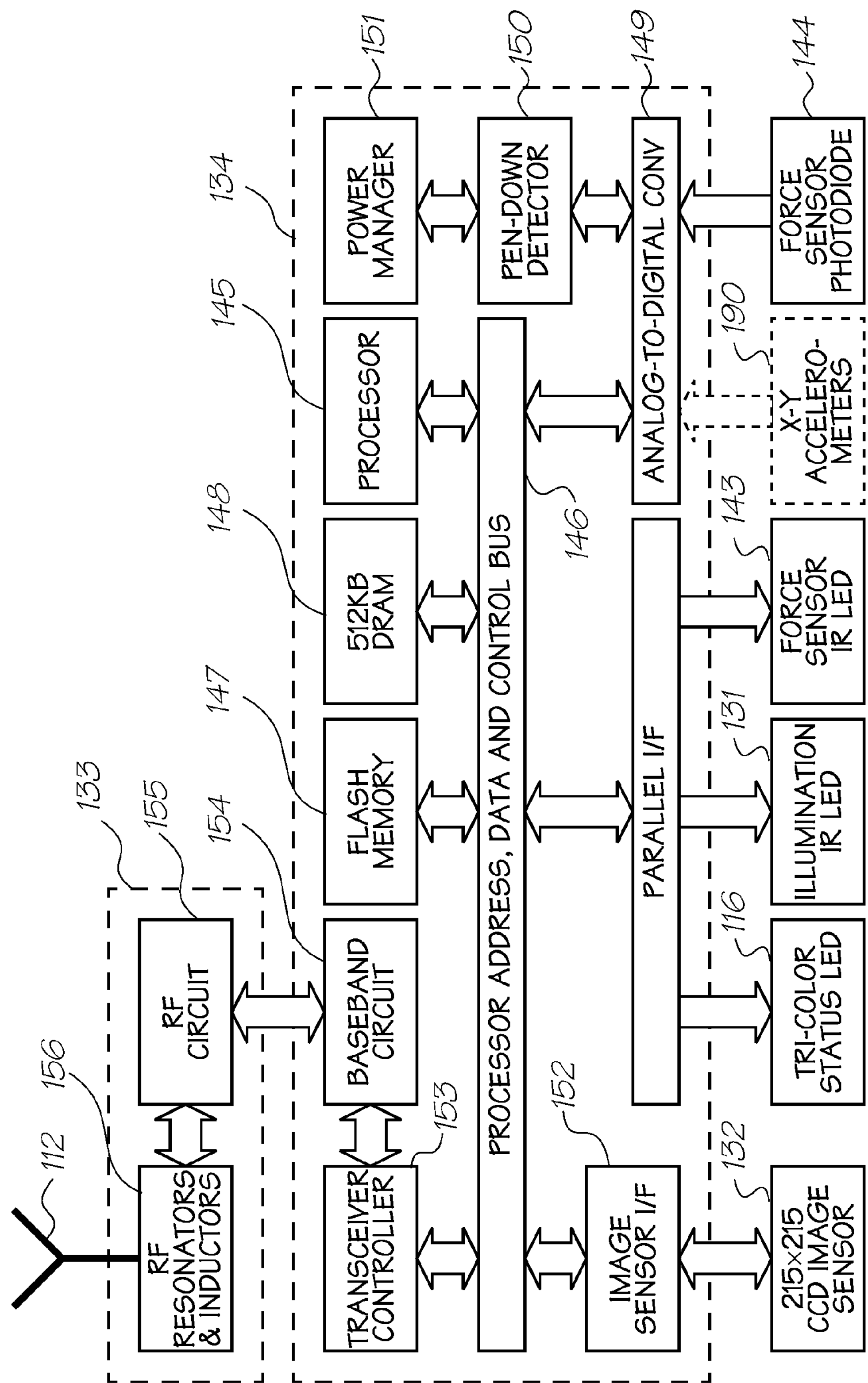
FIG. 8 is a schematic block diagram of a pen controller for the netpage pen shown in FIGS. 6 and 7.

A preferred embodiment of the pen is described in greater detail below, with reference to FIGS. 6 to 8.

1.6 Netpage Interaction

The netpage printer 601 receives data relating to a stroke from the pen 101 when the pen is used to interact with a netpage 1. The coded data 3 of the tags 4 is read by the pen when it is used to execute a movement, such as a stroke. The data allows the identity of the particular page and associated interactive element to be determined and an indication of the relative positioning of the pen relative to the page to be obtained. The indicating data is transmitted to the printer, where it resolves, via the DNS, the page ID 50 of the stroke into the network address of the netpage page server 10 which maintains the corresponding page instance 830. It then transmits the stroke to the page server. If the page was recently identified in an earlier stroke, then the printer may already have the address of the relevant page server in its cache. Each netpage consists of a compact page layout maintained persistently by a netpage page server (see below). The page layout refers to objects such as images, fonts and pieces of text, typically stored elsewhere on the netpage network.

When the page server receives the stroke from the pen, it retrieves the page description to which the stroke applies, and determines which element of the page description the stroke intersects. It is then able to interpret the stroke in the context of the type of the relevant element.

A "click" is a stroke where the distance and time between the pen down position and the subsequent pen up position are both less than some small maximum. An object which is activated by a click typically requires a click to be activated, and accordingly, a longer stroke is ignored. The failure of a pen action, such as a "sloppy" click, to register is indicated by the lack of response from the pen's "ok" LED.

There are two kinds of input elements in a netpage page description: hyperlinks and form fields. Input through a form field can also trigger the activation of an associated hyperlink.

2 Netpage Pen Description 2.1 Pen Mechanics

Referring to FIGS. 6 and 7, the pen, generally designated by reference numeral 101, includes a housing 102 in the form of a plastics moulding having walls 103 defining an interior space 104 for mounting the pen components. The pen top 105 is in operation rotatably mounted at one end 106 of the housing 102. A semi-transparent cover 107 is secured to the opposite end 108 of the housing 102. The cover 107 is also of moulded plastics, and is formed from semi-transparent material in order to enable the user to view the status of the LED mounted within the housing 102. The cover 107 includes a main part 109 which substantially surrounds the end 108 of the housing 102 and a projecting portion 110 which projects back from the main part 109 and fits within a corresponding slot 111 formed in the walls 103 of the housing 102. A radio antenna 112 is mounted behind the projecting portion 110, within the housing 102. Screw threads 113 surrounding an aperture 113A on the cover 107 are arranged to receive a metal end piece 114, including corresponding screw threads 115. The metal end piece 114 is removable to enable ink cartridge replacement.

Also mounted within the cover 107 is a tri-color status LED 116 on a flex PCB 117. The antenna 112 is also mounted on the flex PCB 117. The status LED 116 is mounted at the top of the pen 101 for good all-around visibility.

The pen can operate both as a normal marking ink pen and as a non-marking stylus. An ink pen cartridge 118 with nib 119 and a stylus 120 with stylus nib 121 are mounted side by side within the housing 102. Either the ink cartridge nib 119 or the stylus nib 121 can be brought forward through open end 122 of the metal end piece 114, by rotation of the pen top 105. Respective slider blocks 123 and 124 are mounted to the ink cartridge 118 and stylus 120, respectively. A rotatable cam barrel 125 is secured to the pen top 105 in operation and arranged to rotate therewith. The cam barrel 125 includes a cam 126 in the form of a slot within the walls 181 of the cam barrel. Cam followers 127 and 128 projecting from slider blocks 123 and 124 fit within the cam slot 126. On rotation of the cam barrel 125, the slider blocks 123 or 124 move relative to each other to project either the pen nib 119 or stylus nib 121 out through the hole 122 in the metal end piece 114. The pen 101 has three states of operation. By turning the top 105 through 90° steps, the three states are:

stylus 120 nib 121 out ink cartridge 118 nib 119 out, and neither ink cartridge 118 nib 119 out nor stylus 120 nib 121 out A second flex PCB 129, is mounted on an electronics chassis 130 which sits within the housing 102. The second flex PCB 129 mounts an infrared LED 131 for providing infrared radiation for projection onto the surface. An image sensor 132 is provided mounted on the second flex PCB 129 for receiving reflected radiation from the surface. The second flex PCB 129 also mounts a radio frequency chip 133, which includes an RF transmitter and RF receiver, and a controller chip 134 for controlling operation of the pen 101. An optics block 135 (formed from moulded clear plastics) sits within the cover 107 and projects an infrared beam onto the surface and receives images onto the image sensor 132. Power supply wires 136 connect the components on the second flex PCB 129 to battery contacts 137 which are mounted within the cam barrel 125. A terminal 138 connects to the battery contacts 137 and the cam barrel 125. A three volt rechargeable battery 139 sits within the cam barrel 125 in contact with the battery contacts. An induction charging coil 140 is mounted about the second flex PCB 129 to enable recharging of the battery 139 via induction. The second flex PCB 129 also mounts an infrared LED 143 and infrared photodiode 144 for detecting displacement in the cam barrel 125 when either the stylus 120 or the ink cartridge 118 is used for writing, in order to enable a determination of the force being applied to the surface by the pen nib 119 or stylus nib 121. The IR photodiode 144 detects light from the IR LED 143 via reflectors (not shown) mounted on the slider blocks 123 and 124.

Rubber grip pads 141 and 142 are provided towards the end 108 of the housing 102 to assist gripping the pen 101, and top 105 also includes a clip 142 for clipping the pen 101 to a pocket.

3.2 Pen Controller

The pen 101 is arranged to determine the position of its nib (stylus nib 121 or ink cartridge nib 119) by imaging, in the infrared spectrum, an area of the surface in the vicinity of the nib. It records the location data from the nearest location tag, and is arranged to calculate the distance of the nib 121 or 119 from the location tab utilising optics 135 and controller chip 134. The controller chip 134 calculates the orientation of the pen and the nib-to-tag distance from the perspective distortion observed on the imaged tag.

Utilising the RF chip 133 and antenna 112 the pen 101 can transmit the digital ink data (which is encrypted for security and packaged for efficient transmission) to the computing system.

When the pen is in range of a receiver, the digital ink data is transmitted as it is formed. When the pen 101 moves out of range, digital ink data is buffered within the pen 101 (the pen 101 circuitry includes a buffer arranged to store digital ink data for approximately 12 minutes of the pen motion on the surface) and can be transmitted later.

The controller chip 134 is mounted on the second flex PCB 129 in the pen 101. FIG. 8 is a block diagram illustrating in more detail the architecture of the controller chip 134. FIG. 8 also shows representations of the RF chip 133, the image sensor 132, the tri-color status LED 116, the IR illumination LED 131, the IR force sensor LED 143, and the force sensor photodiode 144.

The pen controller chip 134 includes a controlling processor 145. Bus 146 enables the exchange of data between components of the controller chip 134. Flash memory 147 and a 512 KB DRAM 148 are also included. An analog-to-digital converter 149 is arranged to convert the analog signal from the force sensor photodiode 144 to a digital signal.

An image sensor interface 152 interfaces with the image sensor 132. A transceiver controller 153 and base band circuit 154 are also included to interface with the RF chip 133 which includes an RF circuit 155 and RF resonators and inductors 156 connected to the antenna 112.

The controlling processor 145 captures and decodes location data from tags from the surface via the image sensor 132, monitors the force sensor photodiode 144, controls the LEDs 116, 131 and 143, and handles short-range radio communication via the radio transceiver 153. It is a medium-performance (~40 MHz) general-purpose RISC processor.

The processor 145, digital transceiver components (transceiver controller 153 and baseband circuit 154), image sensor interface 152, flash memory 147 and 512 KB DRAM 148 are integrated in a single controller ASIC. Analog RF components (RF circuit 155 and RF resonators and inductors 156) are provided in the separate RF chip.

The image sensor is a CCD or CMOS image sensor. Depending on tagging scheme, it has a size ranging from about 100×100 pixels to 200×200 pixels. Many miniature CMOS image sensors are commercially available, including the National Semiconductor LM9630.

The controller ASIC 134 enters a quiescent state after a period of inactivity when the pen 101 is not in contact with a surface. It incorporates a dedicated circuit 150 which monitors the force sensor photodiode 144 and wakes up the controller 134 via the power manager 151 on a pen-down event.

The radio transceiver communicates in the unlicensed 900 MHz band normally used by cordless telephones, or alternatively in the unlicensed 2.4 GHz industrial, scientific and medical (ISM) band, and uses frequency hopping and collision detection to provide interference-free communication.

In an alternative embodiment, the pen incorporates an Infrared Data Association (IrDA) interface for short-range communication with a base station or netpage printer.

In a further embodiment, the pen 101 includes a pair of orthogonal accelerometers mounted in the normal plane of the pen 101 axis. The accelerometers 190 are shown in FIGS. 7 and 8 in ghost outline.

The provision of the accelerometers enables this embodiment of the pen 101 to sense motion without reference to surface location tags, allowing the location tags to be sampled at a lower rate. Each location tag ID can then identify an object of interest rather than a position on the surface. For example, if the object is a user interface input element (e.g. a command button), then the tag ID of each location tag within the area of the input element can directly identify the input element.

The acceleration measured by the accelerometers in each of the x and y directions is integrated with respect to time to produce an instantaneous velocity and position.

Since the starting position of the stroke is not known, only relative positions within a stroke are calculated. Although position integration accumulates errors in the sensed acceleration, accelerometers typically have high resolution, and the time duration of a stroke, over which errors accumulate, is short.

3 Netpage Printer Description

3.1 Printer Mechanics

Figure 10A:
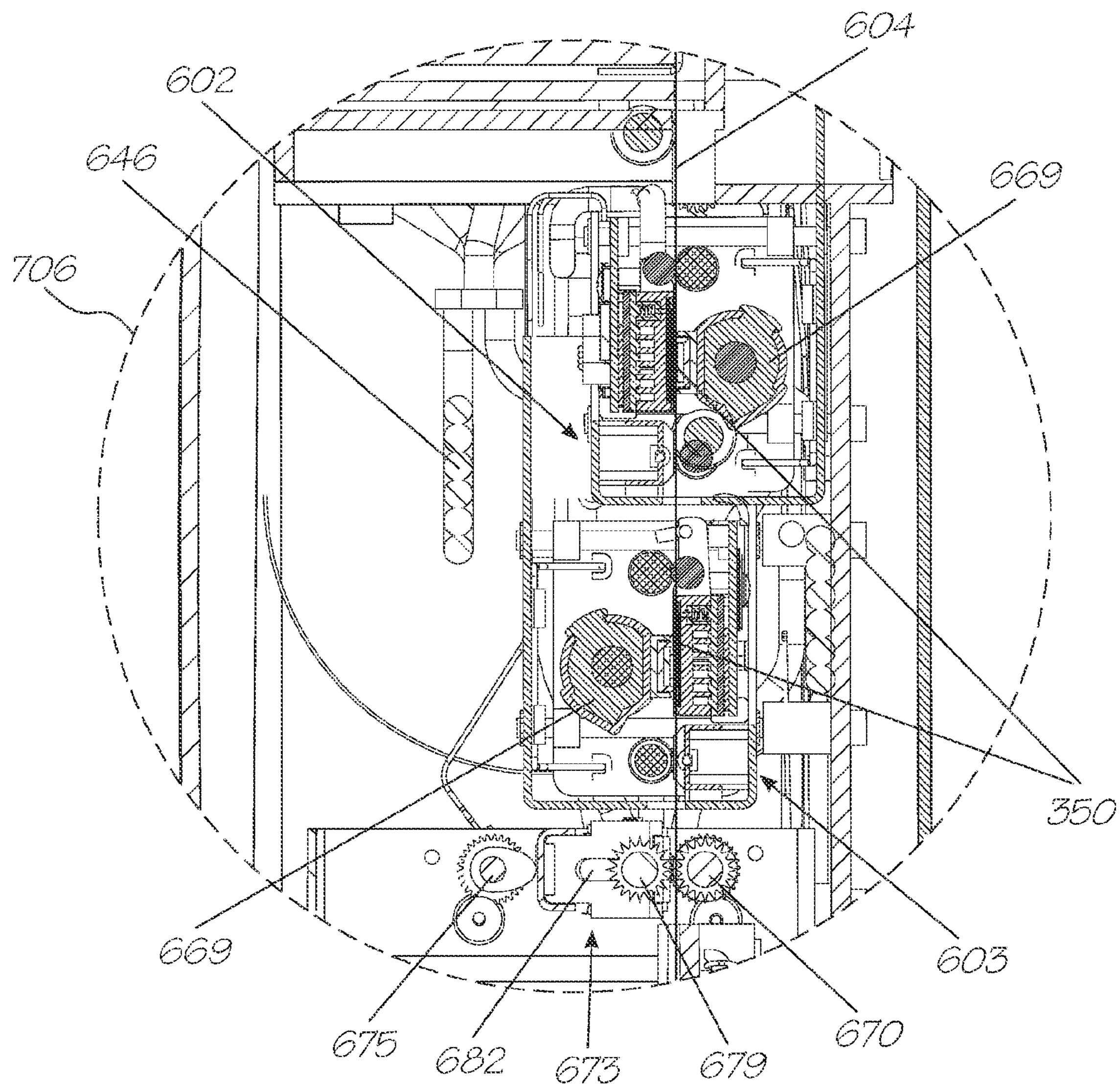
FIG. 10A is an enlarged portion of FIG. 10 showing a section of the duplexed print engines and glue wheel assembly.

The vertically-mounted netpage wallprinter 601 is shown fully assembled in FIG. 9. It prints netpages on Letter/A4 sized media using duplexed 8½" Memjet™ print engines 602 and 603, as shown in FIGS. 10 and 10*a*. It uses a straight paper path with the paper 604 passing through the duplexed print engines 602 and 603 which print both sides of a sheet simultaneously, in full color and with full bleed.

An integral binding assembly 605 applies a strip of glue along one edge of each printed sheet, allowing it to adhere to the previous sheet when pressed against it. This creates a final bound document 618 which can range in thickness from one sheet to several hundred sheets.

Figure 12:
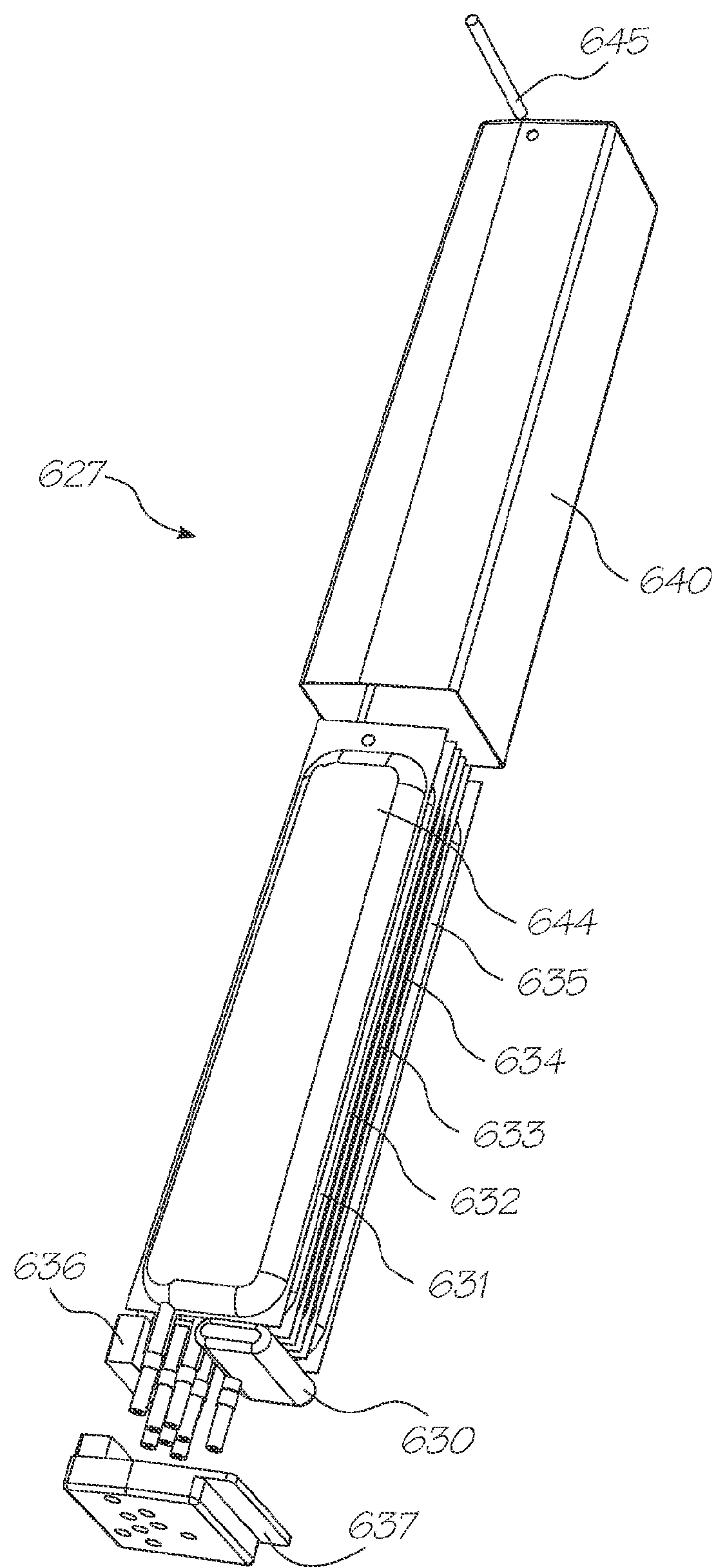
FIG. 12 is an exploded view of an ink cartridge.

The replaceable ink cartridge 627, shown in FIG. 12 coupled with the duplexed print engines, has bladders or chambers for storing fixative, adhesive, and cyan, magenta, yellow, black and infrared inks. The cartridge also contains a micro air filter in a base molding. The micro air filter interfaces with an air pump 638 inside the printer via a hose 639. This provides filtered air to the printheads to prevent ingress of micro particles into the Memjet™ printheads 350 which might otherwise clog the printhead nozzles. By incorporating the air filter within the cartridge, the operational life of the filter is effectively linked to the life of the cartridge. The ink cartridge is a fully recyclable product with a capacity for printing and gluing 3000 pages (1500 sheets).

Referring to FIG. 10, the motorized media pick-up roller assembly 626 pushes the top sheet directly from the media tray past a paper sensor on the first print engine 602 into the duplexed Memjet™ printhead assembly. The two Memjet™ print engines 602 and 603 are mounted in an opposing in-line sequential configuration along the straight paper path. The paper 604 is drawn into the first print engine 602 by integral, powered pick-up rollers 626. The position and size of the paper 604 is sensed and full bleed printing commences. Fixative is printed simultaneously to aid drying in the shortest possible time.

The paper exits the first Memjet™ print engine 602 through a set of powered exit spike wheels (aligned along the straight paper path), which act against a rubberized roller. These spike wheels contact the 'wet' printed surface and continue to feed the sheet 604 into the second Memjet™ print engine 603.

Referring to FIGS. 10 and 10*a*, the paper 604 passes from the duplexed print engines 602 and 603 into the binder assembly 605. The printed page passes between a powered spike wheel axle 670 with a fibrous support roller and another movable axle with spike wheels and a momentary action glue wheel. The movable axle/glue assembly 673 is mounted to a metal support bracket and it is transported forward to interface with the powered axle 670 via gears by action of a camshaft. A separate motor powers this camshaft.

The glue wheel assembly 673 consists of a partially hollow axle 679 with a rotating coupling for the glue supply hose 641 from the ink cartridge 627. This axle 679 connects to a glue wheel, which absorbs adhesive by capillary action through radial holes. A molded housing 682 surrounds the glue wheel, with an opening at the front. Pivoting side moldings and sprung outer doors are attached to the metal bracket and hinge out sideways when the rest of the assembly 673 is thrust forward. This action exposes the glue wheel through the front of the molded housing 682. Tension springs close the assembly and effectively cap the glue wheel during periods of inactivity.

As the sheet 604 passes into the glue wheel assembly 673, adhesive is applied to one vertical edge on the front side (apart from the first sheet of a document) as it is transported down into the binding assembly 605.

4 Product Tagging

Automatic identification refers to the use of technologies such as bar codes, magnetic stripe cards, smartcards, and RF transponders, to (semi-)automatically identify objects to data processing systems without manual keying.

For the purposes of automatic identification, a product item is commonly identified by a 12-digit Universal Product Code (UPC), encoded machine-readably in the form of a printed bar code. The most common UPC numbering system incorporates a 5-digit manufacturer number and a 5-digit item number. Because of its limited precision, a UPC is used to identify a class of product rather than an individual product item. The Uniform Code Council and EAN International define and administer the UPC and related codes as subsets of the 14-digit Global Trade Item Number (GTIN).

Within supply chain management, there is considerable interest in expanding or replacing the UPC scheme to allow individual product items to be uniquely identified and thereby tracked. Individual item tagging can reduce "shrinkage" due to lost, stolen or spoiled goods, improve the efficiency of demand-driven manufacturing and supply, facilitate the profiling of product usage, and improve the customer experience.

There are two main contenders for individual item tagging: optical tags in the form of so-called two-dimensional bar codes, and radio frequency identification (RFID) tags. For a detailed description of RFID tags, refer to Klaus Finkenzeller, *RFID Handbook*, John Wiley & Son (1999), the contents of which are herein incorporated by cross-reference. Optical tags have the advantage of being inexpensive, but require optical line-of-sight for reading. RFID tags have the advantage of supporting omnidirectional reading, but are comparatively expensive. The presence of metal or liquid can seriously interfere with RFID tag performance, undermining the omnidirectional reading advantage. Passive (reader-powered) RFID tags are projected to be priced at 10 cents each in multi-million quantities by the end of 2003, and at 5 cents each soon thereafter, but this still falls short of the sub-one-cent industry target for low-price items such as grocery. The read-only nature of most optical tags has also been cited as a disadvantage, since status changes cannot be written to a tag as an item progresses through the supply chain. However, this disadvantage is mitigated by the fact that a read-only tag can refer to information maintained dynamically on a network.

The Massachusetts Institute of Technology (MIT) Auto-ID Center has developed a standard for a 96-bit Electronic Product Code (EPC), coupled with an Internet-based Object Name Service (ONS) and a Product Markup Language (PML). Once an EPC is scanned or otherwise obtained, it is used to look up, possibly via the ONS, matching product information portably encoded in PML. The EPC consists of an 8-bit header, a 28-bit EPC manager, a 24-bit object class, and a 36-bit serial number. For a detailed description of the EPC, refer to Brock, D. L., *The Electronic Product Code* (*EPC*), MIT Auto-ID Center (January 2001), the contents of which are herein incorporated by cross-reference. The Auto-ID Center has defined a mapping of the GTIN onto the EPC to demonstrate compatibility between the EPC and current practices Brock, D. L., *Integrating the Electronic Product Code* (*EPC*) *and the Global Trade Item Number* (*GTIN*), MIT Auto-ID Center (November 2001), the contents of which are herein incorporated by cross-reference. The EPC is administered by EPCglobal, an EAN-UCC joint venture.

EPCs are technology-neutral and can be encoded and carried in many forms. The Auto-ID Center strongly advocates the use of low-cost passive RFID tags to carry EPCs, and has defined a 64-bit version of the EPC to allow the cost of RFID tags to be minimized in the short term. For detailed description of low-cost RFID tag characteristics, refer to Sarma, S., *Towards the* 5c *Tag*, MIT Auto-ID Center (November 2001), the contents of which are herein incorporated by cross-reference. For a description of a commercially-available low-cost passive RFID tag, refer to 915 *MHz RFID Tag*, Alien Technology (2002), the contents of which are herein incorporated by cross-reference. For detailed description of the 64-bit EPC, refer to Brock, D. L., *The Compact Electronic Product Code*, MIT Auto-ID Center (November 2001), the contents of which are herein incorporated by cross-reference.

EPCs are intended not just for unique item-level tagging and tracking, but also for case-level and pallet-level tagging, and for tagging of other logistic units of shipping and transportation such as containers and trucks. The distributed PML database records dynamic relationships between items and higher-level containers in the packaging, shipping and transportation hierarchy.

4.1 Hyperlabel™ Tagging in the Supply Chain

Using an invisible (e.g. infrared) tagging scheme to uniquely identify a product item has the significant advantage that it allows the entire surface of a product to be tagged, or a significant portion thereof, without impinging on the graphic design of the product's packaging or labelling. If the entire product surface is tagged, then the orientation of the product doesn't affect its ability to be scanned, i.e. a significant part of the line-of-sight disadvantage of a visible bar code is eliminated. Furthermore, since the tags are small and massively replicated, label damage no longer prevents scanning.

Hyperlabel tagging, then, consists of covering a large proportion of the surface of a product item with optically-readable invisible tags. Each Hyperlabel tag uniquely identifies the product item on which it appears. The Hyperlabel may directly encode the product code (e.g. EPC) of the item, or may encode a surrogate ID which in turn identifies the product code via a database lookup. Each Hyperlabel tag also optionally identifies its own position on the surface of the product item, to provide the downstream consumer benefits of netpage interactivity described earlier.

Hyperlabel tags are applied during product manufacture and/or packaging using digital printers. These may be add-on infrared printers which print the Hyperlabel tags after the text and graphics have been printed by other means, or integrated color and infrared printers which print the Hyperlabel tags, text and graphics simultaneously. Digitally-printed text and graphics may include everything on the label or packaging, or may consist only of the variable portions, with other portions still printed by other means.

4.2 Hyperlabel™ Tagging

Figure 13:
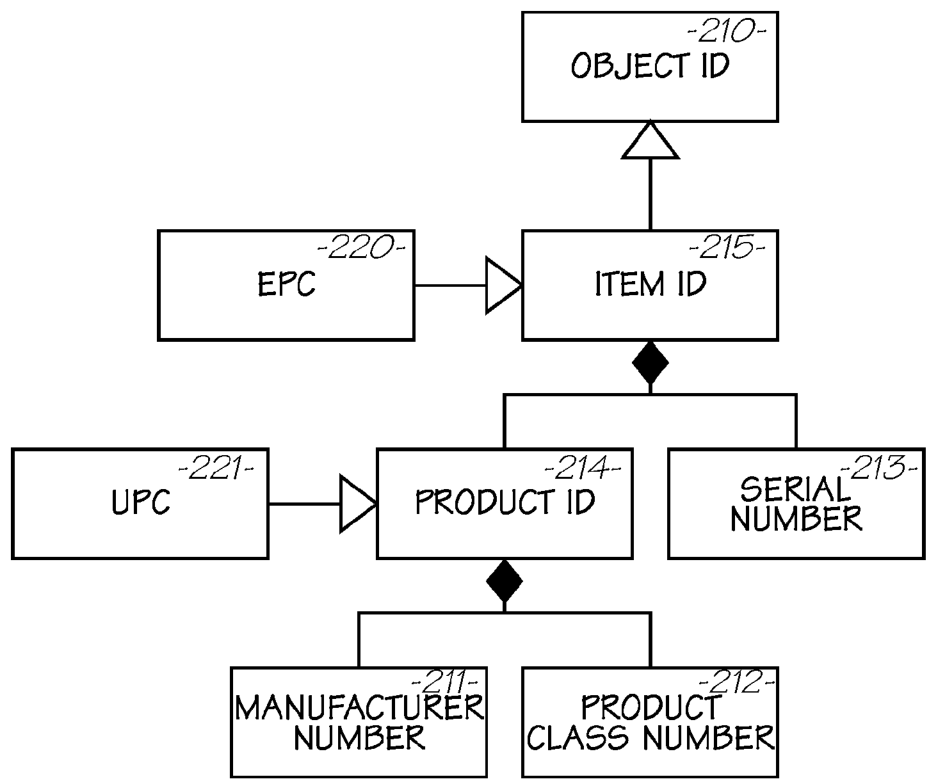
FIG. 13 is a schematic view of the structure of an item ID.

As shown in FIG. 13, a product's unique item ID 215 may be seen as a special kind of unique object ID 210. The Electronic Product Code (EPC) 220 is one emerging standard for an item ID. An item ID typically consists of a product ID 214 and a serial number 213. The product ID identifies a class of product, while the serial number identifies a particular instance of that class, i.e. an individual product item. The product ID in turn typically consists of a manufacturer number 211 and a product class number 212. The best-known product ID is the EAN.UCC Universal Product Code (UPC) 221 and its variants.

As shown in FIG. 14, a Hyperlabel tag 202 encodes a page ID (or region ID) 50 and a two-dimensional (2D) position 86. The region ID identifies the surface region containing the tag, and the position identifies the tag's position within the two-dimensional region. Since the surface in question is the surface of a physical product item 201, it is useful to define a one-to-one mapping between the region ID and the unique object ID 210, and more specifically the item ID 215, of the product item. Note, however, that the mapping can be many-to-one without compromising the utility of the Hyperlabel tag. For example, each panel of a product item's packaging could have a different region ID 50. Conversely, the Hyperlabel tag may directly encode the item ID, in which case the region ID contains the item ID, suitably prefixed to decouple item ID allocation from general netpage region ID allocation. Note that the region ID uniquely distinguishes the corresponding surface region from all other surface regions identified within the global netpage system.

The item ID 215 is preferably the EPC 220 proposed by the Auto-ID Center, since this provides direct compatibility between Hyperlabel tags and EPC-carrying RFID tags.

In FIG. 14 the position 86 is shown as optional. This is to indicate that much of the utility of the Hyperlabel tag in the supply chain derives from the region ID 50, and the position may be omitted if not desired for a particular product.

For interoperability with the netpage system, the Hyperlabel tag 202 is a netpage tag 4, i.e. it has the logical structure, physical layout and semantics of a netpage tag.

When a netpage sensing device such as the netpage pen 101 images and decodes a Hyperlabel tag, it uses the position and orientation of the tag in its field of view and combines this with the position encoded in the tag to compute its own position relative to the tag. As the sensing device is moved relative to a Hyperlabel tagged surface region, it is thereby able to track its own motion relative to the region and generate a set of timestamped position samples representative of its time-varying path. When the sensing device is a pen, then the path consists of a sequence of strokes, with each stroke starting when the pen makes contact with the surface, and ending when the pen breaks contact with the surface.

When a stroke is forwarded to the page server 10 responsible for the region ID, the server retrieves a description of the region keyed by region ID, and interprets the stroke in relation to the description. For example, if the description includes a hyperlink and the stroke intersects the zone of the hyperlink, then the server may interpret the stroke as a designation of the hyperlink and activate the hyperlink.

4.3 Hyperlabel Tag Printing

A Hyperlabel tag printer is a digital printer which prints Hyperlabel tags onto the label, packaging or actual surface of a product before, during or after product manufacture and/or assembly. It is a special case of a netpage printer 601. It is capable of printing a continuous pattern of Hyperlabel tags onto a surface, typically using a near-infrared-absorptive ink. In high-speed environments, the printer includes hardware which accelerates tag rendering. This typically includes real-time Reed-Solomon encoding of variable tag data such as tag position, and real-time template-based rendering of the actual tag pattern at the dot resolution of the printhead.

The printer may be an add-on infrared printer which prints the Hyperlabel tags after text and graphics have been printed by other means, or an integrated color and infrared printer which prints the Hyperlabel tags, text and graphics simultaneously. Digitally-printed text and graphics may include everything on the label or packaging, or may consist only of the variable portions, with other portions still printed by other means. Thus a Hyperlabel tag printer with an infrared and black printing capability can displace an existing digital printer used for variable data printing, such as a conventional thermal transfer or inkjet printer.

For the purposes of the following discussion, any reference to printing onto an item label is intended to include printing onto the item packaging in general, or directly onto the item surface. Furthermore, any reference to an item ID 215 is intended to include a region ID 50 (or collection of per-panel region ids), or a component thereof.

The printer is typically controlled by a host computer, which supplies the printer with fixed and/or variable text and graphics as well as item ids for inclusion in the Hyperlabel tags. The host may provide real-time control over the printer, whereby it provides the printer with data in real time as printing proceeds. As an optimisation, the host may provide the printer with fixed data before printing begins, and only provide variable data in real time. The printer may also be capable of generating per-item variable data based on parameters provided by the host. For example, the host may provide the printer with a base item ID prior to printing, and the printer may simply increment the base item ID to generate successive item ids. Alternatively, memory in the ink cartridge or other storage medium inserted into the printer may provide a source of unique item ids, in which case the printer reports the assignment of items ids to the host computer for recording by the host.

Alternatively still, the printer may be capable of reading a pre-existing item ID from the label onto which the Hyperlabel tags are being printed, assuming the unique ID has been applied in some form to the label during a previous manufacturing step. For example, the item ID may already be present in the form of a visible 2D bar code, or encoded in an RFID tag. In the former case the printer can include an optical bar code scanner. In the latter case it can include an RFID reader.

The printer may also be capable of rendering the item ID in other forms. For example, it may be capable of printing the item ID in the form of a 2D bar code, or of printing the product ID component of the item ID in the form of a ID bar code, or of writing the item ID to a writable or write-once RFID tag.

4.4 Hyperlabel™ Tag Scanning

Item information typically flows to the product server in response to situated scan events, e.g. when an item is scanned into inventory on delivery; when the item is placed on a retail shelf, and when the item is scanned at point of sale. Both fixed and hand-held scanners may be used to scan Hyperlabel tagged product items, using both laser-based 2D scanning and 2D image-sensor-based scanning, using similar or the same techniques as employed in the netpage pen.

Figure 16:
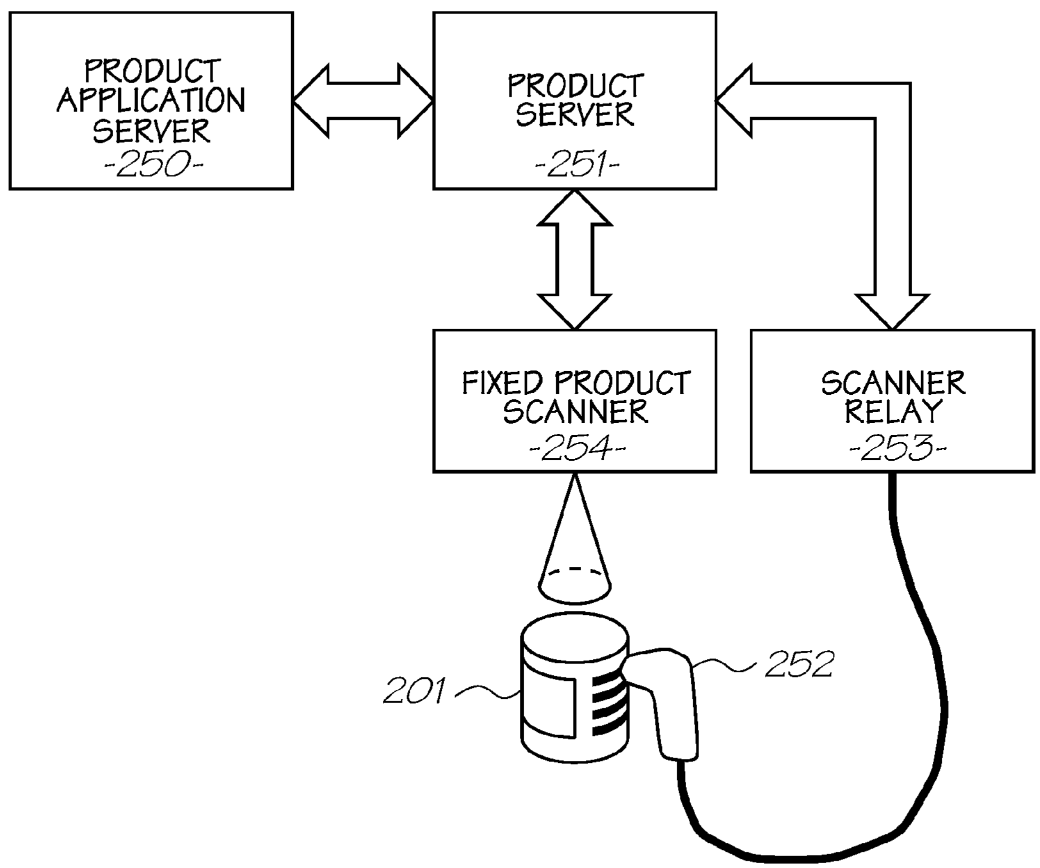
FIG. 16 is a schematic view of the interaction between a product item, a fixed product scanner, a hand-held product scanner, a scanner relay, a product server, and a product application server.

As shown in FIG. 16, both a fixed scanner 254 and a hand-held scanner 252 communicate scan data to the product server 251. The product server may in turn communicate product item event data to a peer product server (not shown), or to a product application server 250, which may implement sharing of data with related product servers. For example, stock movements within a retail store may be recorded locally on the retail store's product server, but the manufacturer's product server may be notified once a product item is sold.

4.5 Hyperlabel™ Tag-Based Netpage Interactions

A product item whose labelling, packaging or actual surface has been Hyperlabel tagged provides the same level of interactivity as any other netpage.

There is a strong case to be made for netpage-compatible product tagging. Netpage turns any printed surface into a finely differentiated graphical user interface akin to a Web page, and there are many applications which map nicely onto the surface of a product. These applications include obtaining product information of various kinds (nutritional information; cooking instructions; recipes; related products; use-by dates; servicing instructions; recall notices); playing games; entering competitions; managing ownership (registration; query, such as in the case of stolen goods; transfer); providing product feedback; messaging; and indirect device control. If, on the other hand, the product tagging is undifferentiated, such as in the case of an undifferentiated 2D barcode or RFID-carried item ID, then the burden of information navigation is transferred to the information delivery device, which may significantly increase the complexity of the user experience or the required sophistication of the delivery device user interface.

The invention will now be described with reference to the following examples. However, it will of course be appreciated that this invention may be embodied in many other forms without departing from the scope of the invention, as defined in the accompanying claims.

4.7 Hyperlabel™ Tags Encoding Layout Data

As described above, a Hyperlabel tagged surface carries a continuous array of Hyperlabel tags. These typically encode the product item's unique identifier (e.g. EPC) and digital signature(s), as well as a two-dimensional coordinate grid.

A range of analog printing processes are used to produce labels and packaging, including gravure, letterpress, offset, flexographic, and digital. Some packaging is produced using multiple processes in sequence. For example, package graphics may be printed on a web-fed flexographic press, while batch and expiry information is digitally printed onto each finished package using laser marking or inkjet.

Hyperlabel tags may be printed digitally using an add-on digital printer, placed either before or after the colour press. The Hyperlabel digital add-on printer can utilise a Memjet printhead as described earlier, or any of a range of commercially-available laser and inkjet printheads such as from HP Indigo, Xaar, Xeikon, Agfa.dotrix, VideoJet, Mark Andy, etc. The Hyperlabel digital printer can be web-fed or sheet-fed according to the line to which it is added.

The add-on digital printer must be synchronised with the colour press to ensure registration between printed graphics and Hyperlabel tags. This can be achieved by conventional means, for example by generating an electronic signal in the colour press synchronised with the printing of an impression, and feeding that signal to the Hyperlabel printer. Alternatively, the Hyperlabel printer can optically detect printed fiducials produced by the colour press, as is sometimes used to synchronise die cutters with a colour press.

The Hyperlabel printer can be merely approximately synchronised with the colour press, and fine synchronisation can be achieved by measuring the actual registration achieved and recording a corresponding offset in the Netpage server database, as described elsewhere in relation to pre-tagged Netpage blanks. The measurement can take place while the packaging is still in the form of web or sheet media, or after being folded or applied to the product item. In the former case detection of the registration of the product graphics is still required, for example via fiducials as mentioned above. In the latter case registration of the product graphics is determined by virtue of the individual package passing along the line. This may be intrinsic in the design of the line, or may involve a photodetector to detect passage of the item. Detection of the Hyperlabel tag pattern uses a Hyperlabel reader in both cases.

Web or sheet media can be pre-printed (or printed in-line by an upstream digital Hyperlabel printer) with Hyperlabel tags which encode a continuous and large two-dimensional coordinate space and no explicit item identifiers. After passing through the colour press, each item's packaging will have a different range of coordinates. These can be detected as described above and recorded in the Netpage server database (and/or a product database) as being associated with the item and its item identifier. When a Hyperlabel tag on a particular item is subsequently read, its coordinate can be translated into an item identifier by querying the Netpage server (or product server).

A digital printhead can be adapted to print both product graphics and Hyperlabel tags, as described earlier in relation to Memjet digital printheads. Other digital printheads can be similarly adapted through the provision for an extra, infrared, ink channel.

As an alternative to digitally printing Hyperlabel tags, Hyperlabel tags can be printed using an analog process such as gravure, letterpress, offset or flexographic, for example on the same colour press used to print product graphics. A colour press is adapted to print Hyperlabel tags through the provision of an extra, infrared, ink channel; i.e. through the provision of an extra plate which bears the image of the Hyperlabel tags. The Hyperlabel plate can be produced by conventional means, such as computer to film (CtF) or direct computer to plate (CtP). It will be appreciated that any of the Hyperlabel tags 202 described hereinafter may be printed with inks according to the present invention.

Note that although Hyperlabel tags are ideally printed using an invisible ink such as infrared ink, they can also be printed using a visible ink such as a coloured, black or gray ink. And although Hyperlabel tags are ideally printed over the entire product package, they can also be printed selectively in specific areas. And although Hyperlabel tags are ideally position-indicating, they can also be object-indicating, as described elsewhere.

Figure 20:
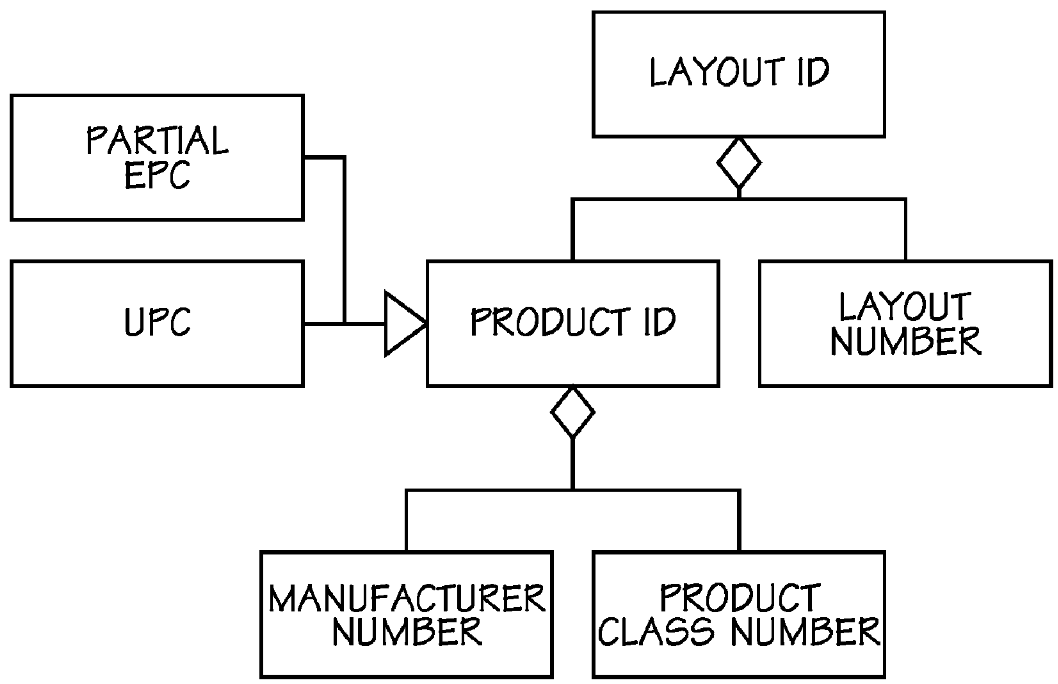
FIG. 20 is an example of a layout ID class diagram.

If Hyperlabel tags are printed using an analog press, then it is impractical to provide each product item package with a unique serial number. However, the Hyperlabel tags can still encode the product identifier portion of the item identifier and the usual two-dimensional coordinate grid. In addition, the tags must encode a unique layout number which identifies the particular graphic (and interactive) layout of the package. The Hyperlabel tags also encode a flag which allows any Hyperlabel reader to determine that the tags encode a layout number rather than a serial number. The layout number only needs to be unique for different layouts associated with the same product identifier. It forms a unique layout identifier when paired with a product identifier, as shown in FIG. 20. The layout number changes precisely when new plates are produced for a new graphic package design, such as for a particular promotion or a particular geographic region. CtP makes frequent layout changes particularly convenient.

Figure 21:
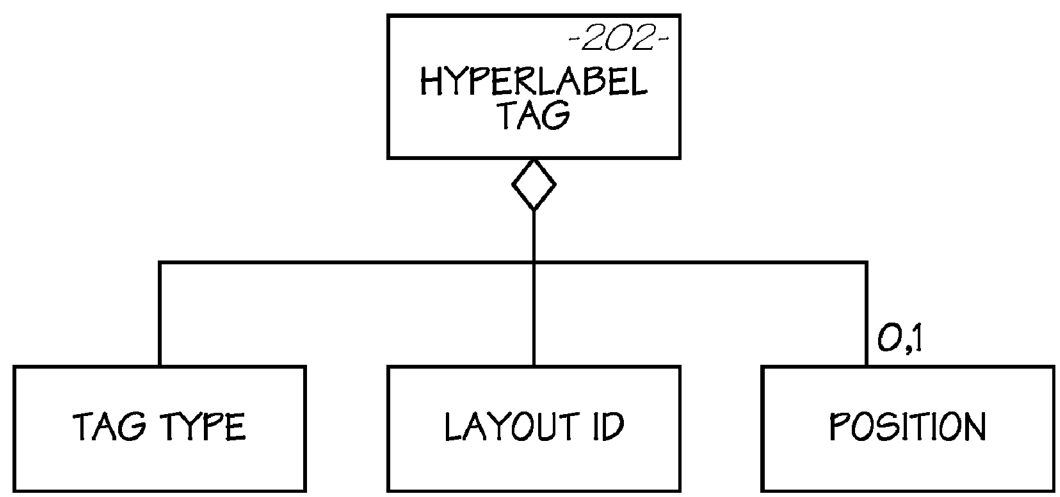
FIG. 21 is an alternative example of Hyperlabel tag class diagram.

Analog-printed Hyperlabel tags can thus encode a layout identifier rather than an item identifier, as shown in FIG. 21. During a subsequent interaction with a product item via a Hyperlabel reader, the layout identifier is used to retrieve the corresponding layout to allow the interaction to be interpreted in the usual way. For convenience we refer to such Hyperlabel tags as "layout-indicating" (to distinguish then from item-indicating Hyperlabel tags), and the data sent from the Hyperlabel reader to the Netpage server as "layout data".

It is convenient to encode a product identifier in the layout identifier, since it allows a Hyperlabel reader to identify the product. However, it is also possible to encode a pure layout identifier in Hyperlabel tags which identifies the layout but does not directly identify the product. Equivalently, it is possible to encode a pure coordinate grid in the Hyperlabel tags and use the range of the coordinates to identify the corresponding layout. Thus all product items sharing the same graphic package layout would share the same coordinate grid range, and a change in layout would result in a change in coordinate grid range. The equivalence of a pure coordinate grid and a coordinate grid coupled with an item or layout identifier is discussed in the cross-referenced applications.

Layout-indicating Hyperlabel tags can confer interactivity in the usual way via the layout identifier and the coordinate grid that they encode, and product identification (but not product item identification) via the product identifier they encode.

Identification of individual product items is still important. It confers the various supply chain benefits discussed at length elsewhere, and plays a role in various interactive scenarios. For example, some product promotions may ideally be single-use, such as entering a competition or redeeming a token.

In addition, item-level identification, coupled with a digital signature unique to the item, allows product item authentication. In the following discussion, item-indicating Hyperlabel tags typically carry the digital signature(s) of the item in the usual way.

4.8 Location-Indicating Tags in Conjunction with Alternative Item Identifiers

Item-level identification can be provided in a variety of ways in conjunction with location-indicating or layout-indicating Hyperlabel tags. For example, location- or layout-indicating tags can be printed over the whole package, while item-indicating tags can be printed in only a small area. This has the benefit that the corresponding digital Hyperlabel printer can be relatively small, since it is no longer required to print tags across the full width of a web or sheet, but only onto a small area of each package. Digital printers for printing batch and expiry information, as well as for printing item-level indicia such as two-dimensional barcodes, are already part of conventional packaging workflows. A small-area digital Hyperlabel printer can be incorporated in a similar place in such packaging workflows.

Figure 22:
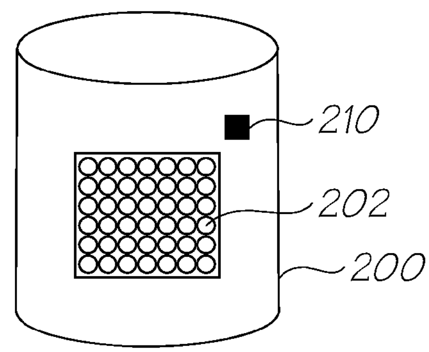
FIG. 22 shows a product item having Hyperlabel tags and a separate RFID tag.
Figure 23:
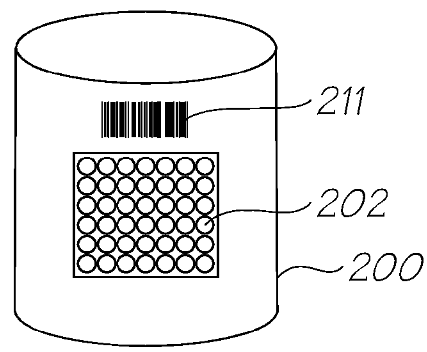
FIG. 23 shows a product item having Hyperlabel tags and a separate barcode identifier.

Item-level identification may be provided using a conventional radio-frequency identification (RFID) tag 210 or a linear or two-dimensional barcode 211 (FIGS. 22 and 23). Even if such carriers are present on a package, it can be convenient to also provide item-indicating Hyperlabel tags 202 in a small area, since these are readable by a standard Hyperlabel reader. Any Hyperlabel hyperlink which requires item-level identification, such as competition entry, token redemption or item authentication, can be implemented in the item-indicating Hyperlabel area. Alternatively, the user can be prompted to click in the item-indicating Hyperlabel area to identify the item, after invoking a single-use hyperlink elsewhere on the product where only layout-indicating tags are present.

If the item-level identification carrier is an RFID tag 210, then the Hyperlabel reader 101 can incorporate an RFID tag reader to allow it to obtain the item identifier from the RFID tag 210 at the same time as it reads location- or layout-indicating Hyperlabel tags 202. Having read the data contained in the Hyperlabel tag(s) 4 and the RFID tag 210, the Hyperlabel reader sends "indicating data", which identifies the item ID and the position of the reader, to the Netpage server. In the case that the Hyperlabel tags 202 are location-indicating tags, the Netpage server can identify the layout from the item ID contained in the indicating data. Thus a Hyperlabel hyperlink requiring item-level identification can be implemented via a combination of location- or layout-indicating Hyperlabel tags 202 and an RFID tag 210. Accordingly, the Hyperlabel reader 101 may comprises an optical sensor for sensing the Hyperlabel tags 202, an RFID transceiver for sensing the RFID tag, a processor for generating the indicating data and means for communicating with the Netpage server (e.g. by wireless or wired communication)

Equivalently, a device already enabled with an RFID reader to provide gross interactivity with an RFID-tagged object or surface can be augmented with a Hyperlabel reader to allow it to support much more fine-grained interactivity with an RFID- and Hyperlabel-tagged object or surface.

If the item-level identification carrier is a visible barcode 211, then invisible item-indicating Hyperlabel tags 202 can be provided in the same area as the barcode. This allows a user of a Hyperlabel reader 101 to click on the barcode to obtain the item identifier, even though the Hyperlabel reader 101 may be unable to read the (arbitrarily large) visible barcode. Alternatively or additionally, item-indicating tags can be printed adjacent to the barcode using the same visible ink as the barcode, to eliminate the need for a separate Hyperlabel ink channel. A Hyperlabel reader 101 can also be augmented to allow it to read conventional barcodes.

An RFID tag or barcode can encode the same item identifier and digital signature(s) as an item-indicating Hyperlabel tag.

Rather than encoding an item identifier explicitly in an RFID tag 210, barcode 211 or Hyperlabel tag 202, a random pattern can be printed and characterised to serve both as an item identifier and as a digital signature. The random pattern, or at least a portion thereof, serves as a "fingerprint" for the object.

In US Patent Application Number 20050045055 ("Security Printing Method" filed 28 Aug. 2003), the contents of which is incorporated herein by reference, Gelbart discusses the addition of powder taggants during printing for the purpose of subsequent authentication. As discussed elsewhere, both the presence of such a taggant and the exact random pattern formed by the taggant can be used as the basis for authentication and possibly identification.

When the random pattern formed by the taggant is used as the basis for authentication, the pattern is measured and recorded during product manufacture or packaging, and is measured and verified, with reference to the earlier recording, during subsequent authentication. The random pattern may cover the entire product surface or a subset thereof. The recorded reference data (reference fingerprints) derived from the pattern may cover the entire pattern or a subset thereof. The verification data (or fingerprint data) derived from the pattern during authentication typically relates to only a small area (e.g. one fingerprint) of the pattern. It is therefore necessary to know which area of the pattern is being verified, so that the verification data can be compared with the correct subset of the reference data. In some systems this relies on detecting other surface features, such as text or line art, and using such features as fiducials. Since such features are typically not unique, this approach may require guidance from a human operator.

Figure 24:
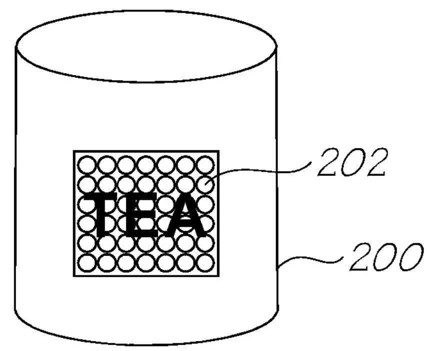
FIG. 24 shows a product item having Hyperlabel tags overprinted with an ink containing a randomly dispersed taggant.
Figure 25:
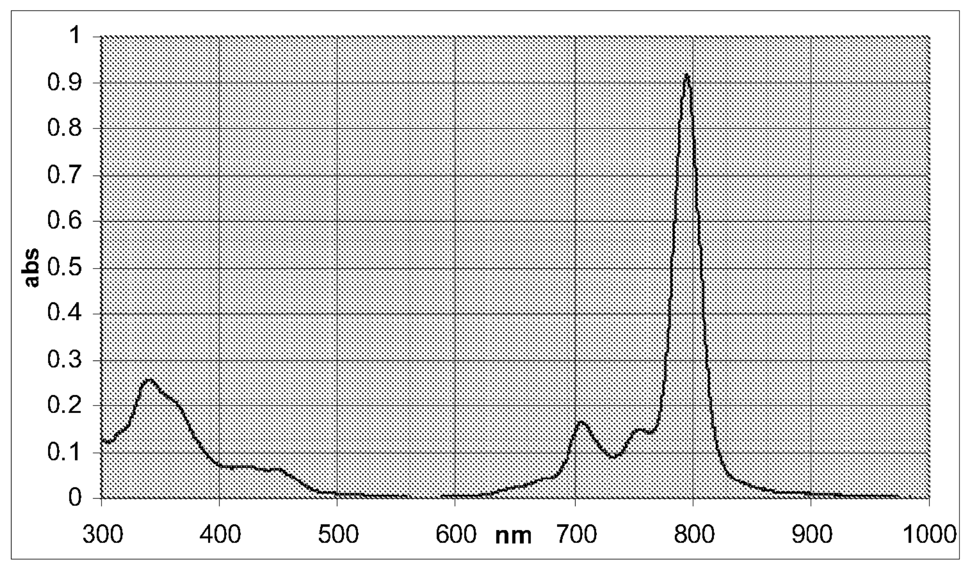
FIG. 25 shows a solution spectrum of the tetrakis(trihexyltetradecylphosphonium) salt 5 at 2.52×10-6 M in DMSO.

Hyperlabel tags 202, since they encode a two-dimensional coordinate grid, provide a unique set of fiducials against which both reference data and verification data can be registered. This increases the reliability of authentication, and eliminates the need for human guidance. The taggant may be mixed with either the infrared ink used to print the Hyperlabels, or it may be mixed with the colored inks used to print graphical user information. In FIG. 24, the ink used to print the word 'TEA' contains a randomly dispersed taggant. Alternatively, if the taggant is applied by mixing it with an infrared ink, then the high density and (typical) full coverage of the Hyperlabel tag pattern 4 ensures that the taggant is also densely present on the entire tagged surface.

Although the random pattern formed by the taggant can be measured across the entire tagged surface, at a minimum it can be measured within a defined region. This region can be graphically delineated to indicate to a user that this is where item-level identification and/or authentication is available.

The random pattern can be characterised for each product package as it passes through the packaging line, either while the packaging is still on the web or sheet, or after the individual package is folded or filled. At this stage the spatial nature of the random pattern is analysed and recorded, either as a set of spatial features or as a hash of such spatial features. For example, each detected feature in the random pattern can be assigned a quantised two-dimensional coordinate within the Hyperlabel coordinate system, and the set of quantised coordinates can be hashed to produce a single compact number. Verification then consists of generating the equivalent hash and comparing it with the reference hash.

A Hyperlabel reader 101 may incorporate a reader for reading the random pattern formed by the taggant. If the taggant is read optically, then the Hyperlabel reader's image sensor can be used to read the taggant pattern. If the taggant uses a different wavelength to the Hyperlabel tag pattern, then the Hyperlabel reader 101 can alternate between activating LEDs matched to the wavelength of the Hyperlabel tag pattern, and LEDs matched to the wavelength of the taggant. If the taggant needs to be imaged with a greater magnification than the Hyperlabel tag pattern, then the Hyperlabel reader can either always image at the greater magnification, and subsample when processing Hyperlabel tag images, or it can incorporate dual optical paths, optionally using a beam splitter to allow a single external aperture.

If no explicit item-level identifier is available (e.g. from an RFID tag 210, barcode 211 or Hyperlabel tag 202), then the reference data (e.g. hash) can also serve as an item identifier. The product item is assigned a standard item identifier at time of manufacture, the standard item identifier is stored in the product database keyed by the reference data, and the standard item identifier can subsequently be recovered using the verification data (e.g. hash) as a key to look up the database, either for identification or verification purposes.

In the presence of layout-indicating Hyperlabel tags which encode a product identifier, the random pattern only needs to map to a serial number, not an entire item identifier.

A serialised product item carries a unique item identifier which typically consists of a product identifier and a serial number. The item ID may be carried by the product item in a number of ways. For example, it may be carried in a linear or two-dimensional barcode 211, a RFID tag 210, or a Hyperlabel tag pattern 4. The product item may also carry a digital signature associated with the item ID which allows a reader to verify with a certain degree of certainty that the item is authentic.

It will be appreciated that any of the Hyperlabel tags 202 described above may be printed with inks according to the present invention.

EXAMPLES

In our previous applications IRB011US, IRB017US and IRB018US (the contents of which are herein incorporated by reference), we described the preparation of various salts of gallium naphthalocyanine tetrasulfonic acid. The skilled person will readily appreciate that the phosphonium salts of the present invention may be easily prepared from corresponding sulfonic acids by conventional methods.

Preparative Example 1

Preparation of Hydroxygallium Naphthalocyaninetetrasulfonic Acid 4

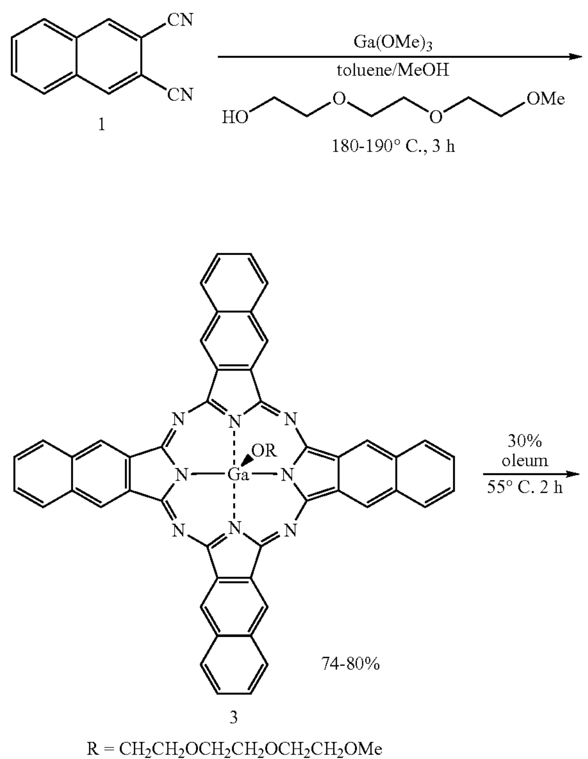

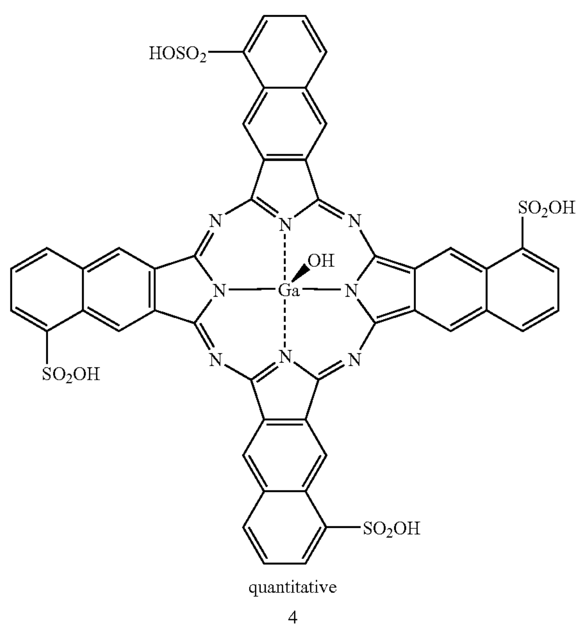

(i) Gallium(III) chloride (5.70 g; 0.032 mol) was dissolved in anhydrous toluene (68 mL) under a slow stream of nitrogen and then the resulting solution was cooled in ice/water. Sodium methoxide (25% in methanol; 23.4 mL) was added slowly with stirring causing a thick white precipitate to form. Upon completion of the addition, the mixture was stirred at room temperature for 1 h and then naphthalene-2,3-dicarbonitrile (22.8 g; 0.128 mol) was added portion-wise, followed by triethylene glycol monomethyl ether (65 mL). The thick slurry was distilled for 2 h to remove the methanol and toluene. Once the toluene had distilled off, the reaction mixture became homogeneous and less viscous and stirred readily. Heating was continued for 3 h at 190° C. (internal). The brown/black reaction mixture was cooled to 60° C., diluted with chloroform (150 mL), and filtered under gravity through a sintered glass funnel. The solid residue was washed with more chloroform (50 mL) and then a further portion (50 mL) with suction under reduced pressure. The resulting dark green solid was then sequentially washed under reduced pressure with acetone (2×50 mL), DMF (2×50 mL), water (2×50 mL), acetone (2×50 mL), and diethyl ether (2×50 mL). The moist solid was air-dried to a dry powder and then heated under high vacuum at ca. 100° C. for 1 h to complete the drying process. Naphthalocyaninatogallium methoxytriethyleneoxide 3 was obtained as a fine dark green powder (23.14 g; 80%), $\lambda_{max}$ (NMP) 770 nm.

(ii) Naphthalocyaninatogallium methoxytriethyleneoxide 3 (9.38 g; 0.010 mol) was treated with 30% oleum (47 mL) by slow addition via a dropping funnel while cooling in an ice/water bath under a nitrogen atmosphere. Upon completion of the addition, the reaction mixture was transferred to a preheated water bath at 55° C. and stirred at this temperature for 2 h during which time the mixture became a homogeneous viscous dark blue solution. The stirred reaction mixture was cooled in an ice/water bath and then 2-propanol (40 mL) was added slowly via a dropping funnel. This mixture was then poured into 2-propanol (100 mL) using more 2-propanol (160 mL) to wash out the residues from the reaction flask. Diethyl ether (100 mL) was then added to the mixture which was then transferred to a sintered glass funnel and filtered under gravity affording a moist dark brown solid and a yellow/brown filtrate. The solid was washed sequentially with ether (50 mL), acetone/ether (1:1, 100 mL), and ether (100 mL) with suction under reduced pressure. The resulting solid (13.4 g) after drying under high vacuum was then stirred in ethanol/ether (1:3, 100 mL) for 3 days and then filtered and dried to give the tetrasulfonic acid 4 as a fine red/brown solid (12.2 g; 105% of theoretical yield; 90% purity according to potentiometric titration). $^1H$ NMR ($d_6$-DMSO) δ 7.97, 8.00 (4H, dd, $J_{7,8}=J_{7,6}=7.2$ Hz, H7); 8.49 (4H, dd, $J_{8,7}=7.2$, $J_{8,1}=5.7$ Hz, H8); 8.84, 8.98 (4H, d, $J_{6,7}$=7.2 Hz, H6); 10.10, 10.19, 10.25 (4H, d, $J_{1,8}$=5.7 Hz, H1); 11.13, 11.16 (4H, s, H4).

Example 1

Preparation of the Tetrakis(trihexyltetradecylphosphonium) Salt 5

5

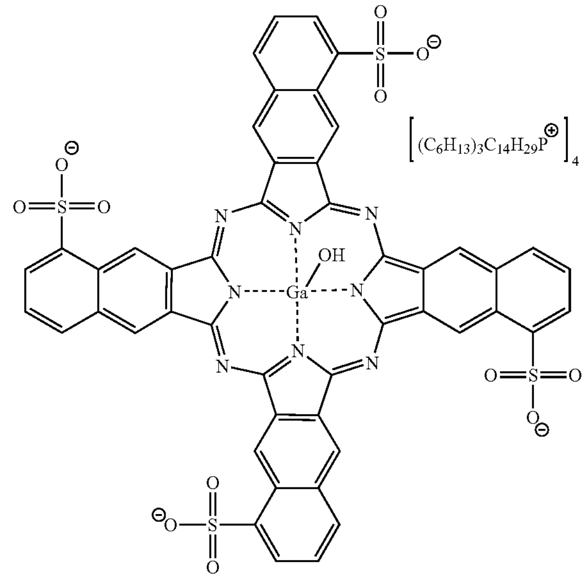

To a solution of hydroxy gallium(III) naphthalocyaninetetrasulfonic acid (29.1 g, 0.026 mol) in water (50 mL) and methanol (350 mL) was added a solution of trihexyltetradecylphosphonium chloride (50.0 g, 0.096 mol) in methanol (50 mL). The solution was concentrated to half volume and the concentrated solution was diluted with water (100 mL) to precipitate the product. The phosphonium salt was filtered off and washed with warm acetone/water (50:50, 2×300 mL) and warm water (2×300 mL) and air dried. The solid was then washed with boiling hexane (2×300 mL) and dried to give the product 5 as a dark green powder (63.1 g, 86%).

$^1$H NMR ($d_6$-DMSO): δ 0.85 (48H, m); 1.0-1.5 (192H, m); 1.90 (32H, m); 7.9-11.1 (20H, m).

UV-Vis-NIR (DMSO): $\lambda_{max}$ 795 nm (ε=365,000); 756 nm (ε=59,000); 706 nm (ε=65,000); 341 nm (ε=102,000).

UV-Vis-NIR($CHCl_3$): $\lambda_{max}$ 790 nm (ε=87,000); 333 nm (ε=85,000).

Comparative Example 1

Preparation of Hexadecyloxygallium(III) Naphthalocyanine 6

6

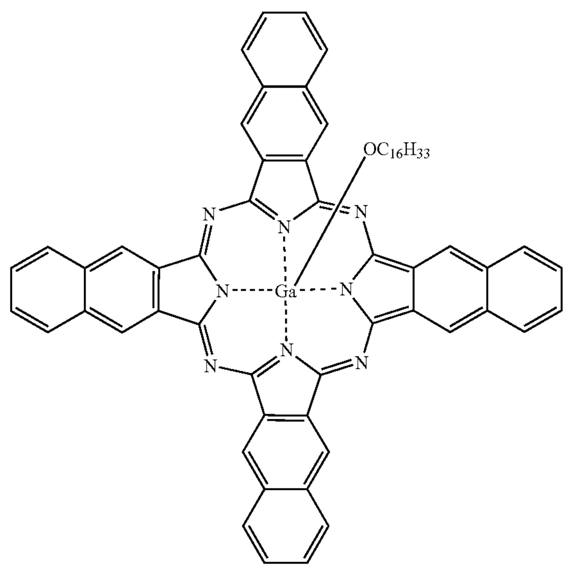

To a solution of gallium(III) chloride (3.68 g, 0.0206 mol) in anhydrous toluene (30 mL) was added dropwise a solution of sodium methoxide in methanol (25%, 14.5 mL=3.63 g, 0.067 mol) to give a colourless precipitate. 2,3-Naphthalenedinitrile (14.6 g, 0.0820 mol, 3.98 eq.), 1-hexadecanol (26.8 g, 0.11 mol) and 1,2-dichlorobenzene (75 mL) were added and the reaction mixture was heated in order to distill off the methanol and toluene. The internal temperature was raised to 170° C. and heating was continued overnight. The temperature was increased to distill about 20 mL of the dichlorobenzene. The reaction mixture was cooled, diluted with acetone (100 mL) and the product was collected by filtration. The solid was washed with acetone, water, and acetone, and air-dried to give the product 6 as a dark-green powder (17.85 g, 85%).

$^1$H NMR ($d_6$-DMSO): δ 0.86 (3H, m); 1.15-1.25 (29H, m); 8.05 (8H, m); 8.85 (8H, m); 10.15 (8H, m).

UV-Vis-NIR (NMP, $5.176\times10^{-6}$ M): $\lambda_{max}$ 770 nm (ε=277,000); 690 nm (ε=51,000); 338 nm(ε=95,000).

Example 2

Ink Formulation Comprising Phosphonium Salt 5

Figure 26:
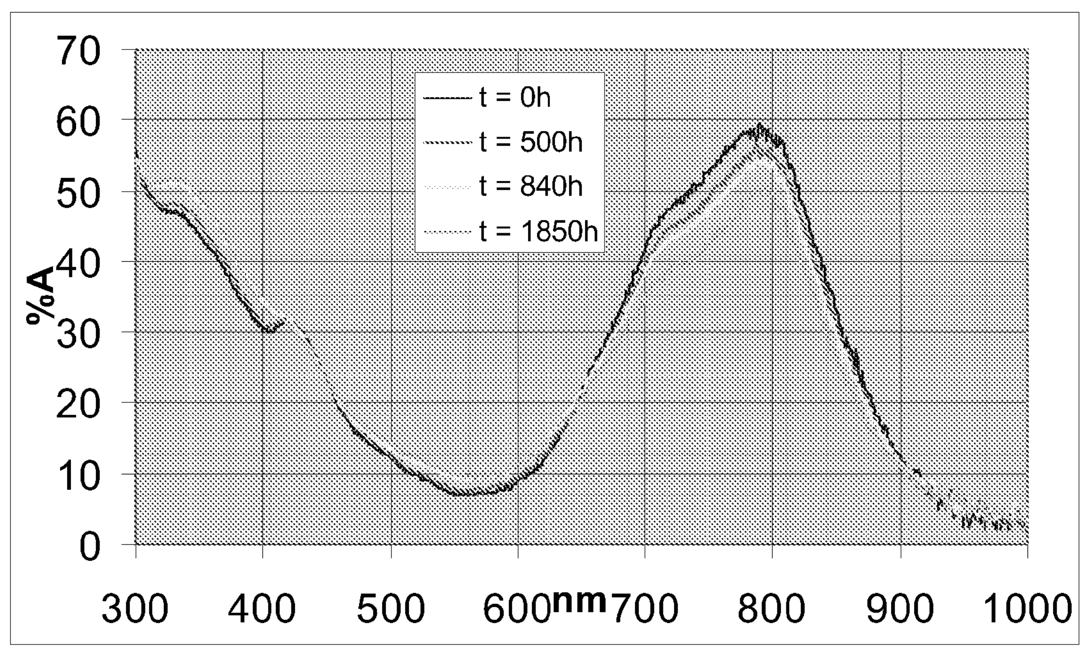
FIG. 26 shows reflectance spectra of an offset printed strip of the phosphonium salt 5 at 3% w/w exposed continuously to direct sunlight and office atmospheric pollutants.

The phosphonium salt 5 was formulated as 3% w/w in a commercially available offset ink vehicle, Matrix ECO PMS Trans White (DIC Colortron Pty Ltd, catalogue number MX 6010/1). The resultant ink was printed as a swatch onto plain paper and exposed to direct sunlight and office atmospheric pollutants. FIG. 26 shows reflectance spectra for the swatch at various times.

Comparative Example 2

Ink Formulation Comprising Hexadecvloxygallium (III) Naphthalocvanine 6

Figure 27:
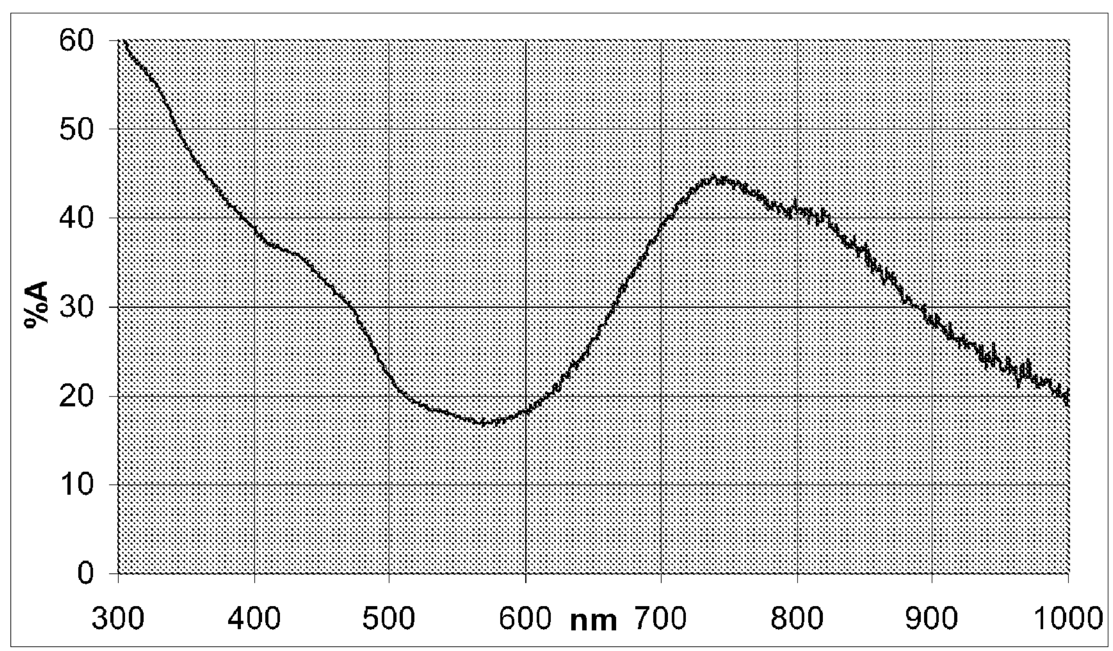
FIG. 27 shows a reflectance spectrum of an offset printed strip of hexadecyloxygallium naphthalocyanine 6 at 3% w/w.

For comparison, the naphthalocyanine 6 was formulated as 3% w/w in the same offset ink vehicle, Matrix ECO PMS Trans White (DIC Colortron Pty Ltd, catalogue number MX 6010/1). The resultant ink was printed as a swatch onto plain paper. FIG. 27 shows the reflectance spectrum for the swatch.

Comparing FIGS. 26 and 27, it can be seen that the phosphonium salt 5 exhibits a sharper and more red-shifted Q-band compared to the naphthalocyanine 6. The red-shift and sharper Q-band are believed to be due to a greater amount of monomer component being present in the phosphonium salt 5, as a result of the phosphonium cation interrupting π-π stacking. These spectra are consistent with the observation that the phosphonium salt 5 is significantly less visible than the naphthalocyanine 6 when printed on paper.

The invention claimed is:

1. A system for interacting with a coded substrate, said system comprising:

a substrate having human-readable information and machine-readable coded data disposed thereon or therein; and a sensing device for reading the machine-readable coded data, wherein said coded data comprises an IR-absorbing phthalocyanine dye comprising one or more sulfonate groups, wherein a counterion of at least one sulfonate group is a phosphonium cation, and wherein:

each phosphonium cation is of formula: $P^+(R^m)(R^n)(R^s)(R^t)$;

each of $R^m$, $R^n$, $R^s$ and $R^t$ is independently selected from the group consisting of: $C_{1-30}$ alkyl, $C_{5-12}$ aryl and $C_{5-30}$ arylalkyl; and at least one of $R^m$, $R^n$, $R^s$ and $R^t$ comprises more than 4 carbon atoms.

2. The system of claim 1, wherein said phthalocyanine dye is contained in a solvent-based or oil-based ink.

3. The system of claim 1, wherein said substrate is printed by an analog printing process.

4. The system of claim 1, wherein said substrate is a printed page.

5. The system of claim 1, wherein said substrate is a label or packaging for a product item.

6. The system of claim 1, wherein said phthalocyanine dye comprises a plurality of sulfonate groups.

7. The system of claim 6, wherein said phthalocyanine dye comprising a corresponding plurality of phosphonium counterions.

8. The system of claim 1, wherein said phthalocyanine dye is a naphthalocyanine dye.

9. The system of claim 1, wherein said phthalocyanine dye is of formula (I):

(I)

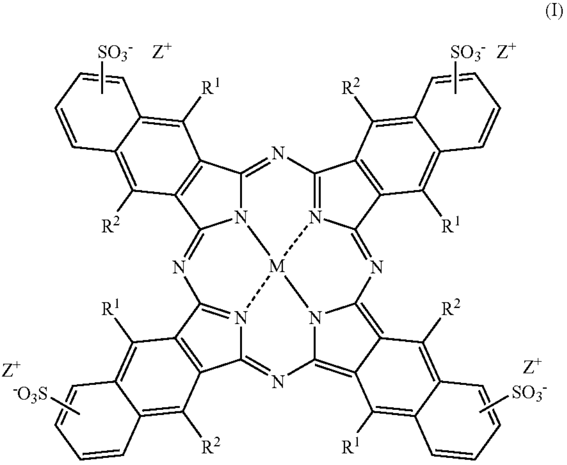

wherein

M is $Ga(A^1)$;

$A^1$ is an axial ligand selected from the group consisting of: —OH, halogen, —$OR^3$, —$OC(O)R^4$ and —$O(CH_2CH_2O)_eR^e$ wherein e is an integer from 2 to 10 and $R^e$ is H, $C_{1-8}$ alkyl or $C(O)C_{1-8}$ alkyl;

$R^1$ and $R^2$ may be the same or different and are selected from the group consisting of:

hydrogen and $C_{1-12}$ alkoxy;

$R^3$ is selected from the group consisting of: $C_{1-12}$ alkyl, $C_{5-12}$ aryl, $C_{5-12}$ arylalkyl and $Si(R^x)(R^y)(R^z)$;

$R^4$ is selected from the group consisting of: $C_{1-12}$ alkyl, $C_{5-12}$ aryl and $C_{5-12}$ arylalkyl;

$R^x$, $R^y$ and $R^z$ may be the same or different and are selected from the group consisting of:

$C_{1-12}$ alkyl, $C_{5-12}$ aryl, $C_{5-12}$ arylalkyl, $C_{1-12}$ alkoxy, $C_{5-12}$ aryloxy and $C_{5-12}$ arylalkoxy; and $Z^+$ is the phosphonium cation of formula: $P+(R^m)(R^n)(R^s)(R^t)$.

10. The system of claim 9, wherein at least three of $R^m$, $R^n$, $R^s$ and $R^t$ comprise more than 4 carbon atoms.

11. The system of claim 9, wherein at least three of $R^m$, $R^n$, $R^s$ and $R^t$ are independently selected from a $C_{6-30}$ alkyl group.

12. The system of claim 9, wherein $R^1$ and $R^2$ are both hydrogen.

13. The system of claim 9, wherein M is Ga(OH).

14. The system of claim 1, wherein said sensing device comprises an image sensor with an IR filter.

15. The system of claim 14, wherein said sensing device is an optically imaging pen.

16. The system of claim 15, wherein said pen has a nib for interacting with the substrate.

* * * * *